(12) United States Patent
Alonso-Soski et al.

(10) Patent No.: US 12,070,313 B2
(45) Date of Patent: Aug. 27, 2024

(54) SENSOR ASSEMBLY OF A MICRONEEDLE ARRAY-BASED CONTINUOUS ANALYTE MONITORING DEVICE

(71) Applicant: Biolinq Incorporated, San Diego, CA (US)

(72) Inventors: Daniel Alonso-Soski, San Diego, CA (US); Anderson Micu, San Diego, CA (US); Yan Li, San Diego, CA (US); Christopher Griffith, San Diego, CA (US); Jennifer Ruth Walters Fuchs, Carlsbad, CA (US)

(73) Assignee: Biolinq Incorporated, San Diego, CA (US)

( * ) Notice: Subject to any disclaimer, the term of this patent is extended or adjusted under 35 U.S.C. 154(b) by 0 days.

(21) Appl. No.: 18/347,522

(22) Filed: Jul. 5, 2023

(65) Prior Publication Data
US 2024/0008777 A1    Jan. 11, 2024

Related U.S. Application Data

(60) Provisional application No. 63/358,459, filed on Jul. 5, 2022.

(51) Int. Cl.
*A61B 5/1473* (2006.01)
*A61B 5/00* (2006.01)
*A61B 5/145* (2006.01)

(52) U.S. Cl.
CPC ............ *A61B 5/1473* (2013.01); *A61B 5/685* (2013.01); *A61B 5/14532* (2013.01); *A61B 2560/0219* (2013.01)

(58) Field of Classification Search
CPC .... A61B 2560/0204; A61B 2560/0209; A61B 2560/0214; A61B 2560/0219;
(Continued)

(56) References Cited

U.S. PATENT DOCUMENTS 7,715,893 B2    5/2010   Kamath et al.
7,811,231 B2    10/2010  Jin et al.
(Continued)

FOREIGN PATENT DOCUMENTS

WO    WO-2018071265 A1    4/2018
WO    WO-2020117918 A1    6/2020
(Continued)

OTHER PUBLICATIONS

Abbot press release (2020). "New late-breaking data show use of Abbott's Freestyle® Libre System significantly reduces HBA1C levels in people with type 2 diabetes using insulin or not," 3 pages.
(Continued)

*Primary Examiner* — Navin Natnithithadha
*Assistant Examiner* — Alice Ling Zou
(74) *Attorney, Agent, or Firm* — Cooley LLP

(57) ABSTRACT

Aspects of the current subject matter are directed to a sensor assembly of an analyte monitoring device including one or more microneedle arrays. Aspects are directed to components and architecture of a sensor assembly to implement power and processing aspects of a microneedle array-based continuous analyte monitoring device for the detection and measuring of an analyte. A source of a power-on event is determined, and the analyte monitoring device is transitioned to a mode that corresponds to the determined source. When a power-on event is determined to be a valid power-on event, the analyte monitoring device is transition to a mode that corresponds to a type of the valid power-on event.

21 Claims, 28 Drawing Sheets

(58) Field of Classification Search
CPC ....... A61B 2560/0266; A61B 55/1451–14514;
A61B 5/14532; A61B 5/1473–14735;
A61B 5/14865; H02J 50/001; H02J
50/05; H02J 50/10; H02J 50/20; H02J
50/80
USPC .......................... 700/90; 713/320, 323, 340
See application file for complete search history.

(56) References Cited

U.S. PATENT DOCUMENTS

| | | |
|---|---|---|
| 7,917,186 B2 | 3/2011 | Kamath et al. |
| 7,996,158 B2 | 8/2011 | Hayter et al. |
| 8,060,173 B2 | 11/2011 | Goode, Jr. et al. |
| 8,094,009 B2 | 1/2012 | Allen et al. |
| 8,103,471 B2 | 1/2012 | Hayter |
| 8,125,331 B2 | 2/2012 | Allen et al. |
| 8,130,095 B2 | 3/2012 | Allen et al. |
| 8,216,139 B2 | 7/2012 | Brauker et al. |
| 8,251,906 B2 | 8/2012 | Brauker et al. |
| 8,260,393 B2 | 9/2012 | Kamath et al. |
| 8,282,549 B2 | 10/2012 | Brauker et al. |
| 8,284,046 B2 | 10/2012 | Allen et al. |
| 8,287,453 B2 | 10/2012 | Li et al. |
| 8,290,559 B2 | 10/2012 | Shariati et al. |
| 8,352,196 B2 | 1/2013 | Vering et al. |
| 8,374,667 B2 | 2/2013 | Brauker et al. |
| 8,423,114 B2 | 4/2013 | Simpson et al. |
| 8,435,179 B2 | 5/2013 | Goode, Jr. et al. |
| 8,463,350 B2 | 6/2013 | Kamath et al. |
| 8,483,793 B2 | 7/2013 | Simpson et al. |
| 8,548,551 B2 | 10/2013 | Kamath et al. |
| 8,565,849 B2 | 10/2013 | Kamath et al. |
| 8,571,808 B2 | 10/2013 | Hayter |
| RE44,695 E | 1/2014 | Simpson et al. |
| 8,626,257 B2 | 1/2014 | Li et al. |
| 8,747,315 B2 | 6/2014 | Brauker et al. |
| 8,790,260 B2 | 7/2014 | Goode, Jr. et al. |
| 8,795,177 B2 | 8/2014 | Goode, Jr. et al. |
| 8,801,610 B2 | 8/2014 | Brauker et al. |
| 8,845,536 B2 | 9/2014 | Brauker et al. |
| 9,192,328 B2 | 11/2015 | Brauker et al. |
| 9,320,461 B2 | 4/2016 | Doniger et al. |
| 9,364,173 B2 | 6/2016 | Brauker et al. |
| 9,408,567 B2 | 8/2016 | Wang et al. |
| 9,700,253 B2 | 7/2017 | Estes et al. |
| 9,737,247 B2 | 8/2017 | Wang et al. |
| 9,743,870 B2 | 8/2017 | Wang et al. |
| 9,750,439 B2 | 9/2017 | Doniger et al. |
| 9,808,190 B2 | 11/2017 | Bohm et al. |
| 9,933,387 B1 | 4/2018 | McCanna et al. |
| 10,001,450 B2 | 6/2018 | Grosman et al. |
| 10,004,442 B2 | 6/2018 | Böhm et al. |
| 10,052,055 B2 | 8/2018 | Li et al. |
| 10,092,207 B1 | 10/2018 | Windmiller |
| 10,136,844 B2 | 11/2018 | Simpson et al. |
| 10,136,846 B2 | 11/2018 | Wang et al. |
| 10,165,968 B2 | 1/2019 | Choi et al. |
| 10,188,333 B2 | 1/2019 | Kamath et al. |
| 10,194,844 B2 | 2/2019 | Harper |
| 10,194,850 B2 | 2/2019 | Kovatchev et al. |
| 10,231,655 B2 | 3/2019 | Wedekind et al. |
| 10,238,323 B2 | 3/2019 | Vanslyke et al. |
| 10,251,588 B2 | 4/2019 | Liang et al. |
| 10,261,069 B2 | 4/2019 | Hayter et al. |
| 10,327,688 B2 | 6/2019 | Böhm et al. |
| 10,335,075 B2 | 7/2019 | Vanslyke et al. |
| 10,349,874 B2 | 7/2019 | Doniger et al. |
| 10,398,363 B2 | 9/2019 | Hayter et al. |
| 10,420,494 B2 | 9/2019 | Simpson et al. |
| 10,426,385 B2 | 10/2019 | Varsavsky et al. |
| 10,448,873 B2 | 10/2019 | Böhm et al. |
| 10,492,708 B1 | 12/2019 | Windmiller |
| D875,254 S | 2/2020 | Cooke et al. |
| 10,575,791 B2 | 3/2020 | Duke et al. |
| 10,610,103 B2 | 4/2020 | Brister et al. |
| 10,660,555 B2 | 5/2020 | Wang et al. |
| 10,667,759 B2 | 6/2020 | Duke et al. |
| 10,682,084 B2 | 6/2020 | Böhm et al. |
| 10,709,361 B2 | 7/2020 | Chen et al. |
| 10,709,362 B2 | 7/2020 | Simpson et al. |
| 10,729,388 B2 | 8/2020 | Reihman et al. |
| 10,771,607 B2 | 9/2020 | Mandapaka et al. |
| 10,786,185 B2 | 9/2020 | Goode, Jr. et al. |
| 10,827,954 B2 | 11/2020 | Hoss et al. |
| 10,881,334 B2 | 1/2021 | Facchinetti et al. |
| 10,932,700 B2 | 3/2021 | Simpson et al. |
| 10,945,630 B2 | 3/2021 | Varsavsky et al. |
| 10,945,644 B2 | 3/2021 | Raisoni et al. |
| 10,980,461 B2 | 4/2021 | Simpson et al. |
| 10,993,642 B2 | 5/2021 | Simpson et al. |
| 11,000,215 B1 | 5/2021 | Simpson et al. |
| 11,020,031 B1 | 6/2021 | Simpson et al. |
| 11,026,605 B1 | 6/2021 | Simpson et al. |
| 11,026,640 B1 | 6/2021 | Hampapuram et al. |
| 11,032,855 B2 | 6/2021 | Mandapaka et al. |
| 11,045,142 B1 | 6/2021 | Windmiller et al. |
| 11,045,147 B2 | 6/2021 | Fennell |
| 11,051,726 B2 | 7/2021 | Kamath et al. |
| 11,051,731 B2 | 7/2021 | Ma et al. |
| 11,055,198 B2 | 7/2021 | Salameh et al. |
| 11,058,358 B2 | 7/2021 | Lee et al. |
| 11,061,491 B2 | 7/2021 | Budiman |
| 11,064,917 B2 | 7/2021 | Simpson et al. |
| 11,064,951 B2 | 7/2021 | Zhong et al. |
| 11,069,443 B2 | 7/2021 | Vleugels et al. |
| 11,071,455 B2 | 7/2021 | Dehennis et al. |
| 11,089,980 B1 | 8/2021 | Biesinger et al. |
| 11,103,165 B2 | 8/2021 | Peyser et al. |
| 11,115,456 B2 | 9/2021 | Root et al. |
| 11,116,400 B2 | 9/2021 | Tankiewicz et al. |
| 11,116,402 B2 | 9/2021 | DeHennis |
| 11,116,431 B1 | 9/2021 | Harper |
| 11,116,898 B2 | 9/2021 | Hayter et al. |
| 11,119,090 B2 | 9/2021 | Hayter et al. |
| 11,145,410 B2 | 10/2021 | Greene et al. |
| 11,147,480 B2 | 10/2021 | Liu et al. |
| 11,147,483 B2 | 10/2021 | Boock et al. |
| 11,154,223 B2 | 10/2021 | Southerland, III et al. |
| 11,160,477 B2 | 11/2021 | Yang et al. |
| 11,179,069 B2 | 11/2021 | Bohm et al. |
| 11,185,264 B2 | 11/2021 | Chen et al. |
| 11,191,463 B2 | 12/2021 | Scott et al. |
| 11,193,924 B2 | 12/2021 | Bhavaraju et al. |
| 11,202,586 B2 | 12/2021 | Sloan et al. |
| 11,202,592 B2 | 12/2021 | Budiman et al. |
| 11,213,230 B2 | 1/2022 | Nishida et al. |
| 11,213,231 B2 | 1/2022 | Wang et al. |
| 11,213,622 B2 | 1/2022 | Sloan et al. |
| 11,229,406 B2 | 1/2022 | Zhong et al. |
| 11,234,624 B2 | 2/2022 | Yang et al. |
| 11,234,625 B2 | 2/2022 | Hayter et al. |
| 11,241,175 B2 | 2/2022 | Sloan et al. |
| 11,246,990 B2 | 2/2022 | Brauker et al. |
| 11,253,176 B2 | 2/2022 | Varsavsky et al. |
| 11,272,867 B2 | 3/2022 | Peyser et al. |
| 11,272,869 B2 | 3/2022 | Kamath et al. |
| 11,282,603 B2 | 3/2022 | Budiman |
| 11,295,860 B2 | 4/2022 | Wolf et al. |
| 11,298,056 B2 | 4/2022 | Harper |
| 11,300,561 B2 | 4/2022 | Hayter et al. |
| 11,304,664 B2 | 4/2022 | Budiman et al. |
| 11,311,213 B2 | 4/2022 | Booth et al. |
| 11,311,215 B2 | 4/2022 | Lin et al. |
| 11,311,217 B2 | 4/2022 | Ajemba et al. |
| 11,331,051 B2 | 5/2022 | Dunn et al. |
| 11,344,235 B2 | 5/2022 | Nogueira et al. |
| 11,357,428 B2 | 6/2022 | Feldman |
| 11,363,975 B2 | 6/2022 | Peyser et al. |
| 11,382,527 B2 | 7/2022 | Varsavsky et al. |
| 11,389,090 B2 | 7/2022 | Kamath et al. |
| 11,391,723 B2 | 7/2022 | Harper et al. |
| 11,399,746 B2 | 8/2022 | Choi et al. |
| 11,399,748 B2 | 8/2022 | Peyser et al. |
| 11,406,818 B2 | 8/2022 | Windmiller |

(56) References Cited

U.S. PATENT DOCUMENTS

| | | |
|---|---|---|
| 11,412,961 B2 | 8/2022 | Lee |
| 11,412,992 B2 | 8/2022 | Sparacino et al. |
| 11,424,015 B2 | 8/2022 | Doniger et al. |
| 11,426,102 B2 | 8/2022 | Frank et al. |
| 11,432,772 B2 | 9/2022 | Kamath et al. |
| 11,445,910 B2 | 9/2022 | Jennewine |
| 11,445,951 B2 | 9/2022 | Ajemba et al. |
| 11,450,421 B2 | 9/2022 | Davis et al. |
| 11,452,467 B2 | 9/2022 | Masciotti et al. |
| 11,464,430 B2 | 10/2022 | Budiman |
| 11,464,434 B2 | 10/2022 | Budiman et al. |
| 11,464,461 B1 | 10/2022 | Biesinger et al. |
| 11,471,082 B2 | 10/2022 | Varsavsky et al. |
| 11,478,173 B2 | 10/2022 | Taub et al. |
| 11,478,194 B2 | 10/2022 | Windmiller et al. |
| 11,484,232 B2 | 11/2022 | Harley-Trochimczyk et al. |
| 11,484,233 B2 | 11/2022 | Harley-Trochimczyk et al. |
| 11,484,234 B2 | 11/2022 | Budiman et al. |
| 11,497,420 B2 | 11/2022 | Wynbrandt et al. |
| 11,504,004 B2 | 11/2022 | Garcia et al. |
| 11,510,570 B2 | 11/2022 | Valdes et al. |
| 11,547,330 B2 | 1/2023 | Wu |
| 11,654,270 B2 | 5/2023 | Mansfield, III et al. |
| D988,160 S | 6/2023 | Morelock |
| 11,672,965 B2 | 6/2023 | Mansfield, III et al. |
| D996,999 S | 8/2023 | Morelock |
| D1,012,744 S | 1/2024 | Morelock |
| 11,857,344 B2 | 1/2024 | Windmiller et al. |
| 11,872,055 B2 | 1/2024 | Tangney et al. |
| D1,013,544 S | 2/2024 | Morelock |
| 11,904,127 B2 | 2/2024 | Mansfield et al. |
| 2007/0046372 A1* | 3/2007 | Kato .................. A61B 5/0245 330/254 |
| 2010/0056873 A1 | 3/2010 | Allen et al. |
| 2014/0266776 A1* | 9/2014 | Miller ................ A61B 5/0015 340/870.01 |
| 2015/0018643 A1* | 1/2015 | Cole .................. A61B 5/0015 600/316 |
| 2016/0198988 A1 | 7/2016 | Bhavaraju et al. |
| 2017/0173261 A1 | 6/2017 | O'Connor et al. |
| 2017/0281092 A1* | 10/2017 | Burnette ............. A61B 5/1473 |
| 2018/0182491 A1* | 6/2018 | Belliveau ............. A61M 5/142 |
| 2018/0344257 A1 | 12/2018 | Hayter et al. |
| 2019/0000358 A1 | 1/2019 | Patel |
| 2019/0029575 A1 | 1/2019 | Taub et al. |
| 2019/0035488 A1 | 1/2019 | Budiman |
| 2019/0035493 A1 | 1/2019 | Doniger et al. |
| 2019/0041345 A1 | 2/2019 | Nogueira et al. |
| 2019/0053743 A1 | 2/2019 | Simpson et al. |
| 2019/0069823 A1 | 3/2019 | Feldman et al. |
| 2019/0076066 A1 | 3/2019 | Ajemba et al. |
| 2019/0076068 A1 | 3/2019 | Yang et al. |
| 2019/0086385 A1 | 3/2019 | Ou et al. |
| 2019/0090789 A1 | 3/2019 | Kamath et al. |
| 2019/0104974 A1 | 4/2019 | Hayter et al. |
| 2019/0110724 A1 | 4/2019 | Kamath et al. |
| 2019/0125223 A1 | 5/2019 | Wang et al. |
| 2019/0150803 A1 | 5/2019 | Vanslyke et al. |
| 2019/0175080 A1 | 6/2019 | Varsavsky et al. |
| 2019/0223765 A1 | 7/2019 | Harley-Trochimczyk et al. |
| 2019/0261903 A1 | 8/2019 | Böhm et al. |
| 2019/0309433 A1 | 10/2019 | Sattayasamitsathit et al. |
| 2020/0077931 A1 | 3/2020 | Goldner et al. |
| 2020/0085341 A1 | 3/2020 | Windmiller |
| 2020/0101286 A1 | 4/2020 | Windmiller et al. |
| 2020/0214566 A1 | 7/2020 | Allen et al. |
| 2020/0254240 A1 | 8/2020 | Windmiller et al. |
| 2020/0297997 A1 | 9/2020 | Windmiller et al. |
| 2020/0323497 A1 | 10/2020 | Reihman et al. |
| 2020/0337607 A1 | 10/2020 | Vanslyke et al. |
| 2020/0375549 A1 | 12/2020 | Wexler et al. |
| 2020/0405202 A1 | 12/2020 | Goode, Jr. et al. |
| 2021/0161438 A1 | 6/2021 | Crouther et al. |
| 2021/0169380 A1 | 6/2021 | Brister et al. |
| 2021/0177318 A1 | 6/2021 | Lintereur |
| 2021/0183489 A1 | 6/2021 | Monirabbasi et al. |
| 2021/0187286 A1 | 6/2021 | Windmiller et al. |
| 2021/0193287 A1 | 6/2021 | Patek |
| 2021/0200787 A1 | 7/2021 | Wei et al. |
| 2021/0209497 A1 | 7/2021 | Wang et al. |
| 2021/0218481 A1 | 7/2021 | Breton et al. |
| 2021/0219879 A1 | 7/2021 | Bhattacharya |
| 2021/0225524 A1 | 7/2021 | Hayter et al. |
| 2021/0228114 A1 | 7/2021 | Rebec et al. |
| 2021/0231639 A1 | 7/2021 | Hayter et al. |
| 2021/0241916 A1 | 8/2021 | Wexler et al. |
| 2021/0251526 A1 | 8/2021 | Estes et al. |
| 2021/0251529 A1 | 8/2021 | Hayter et al. |
| 2021/0251576 A1 | 8/2021 | Budiman et al. |
| 2021/0257076 A1 | 8/2021 | Mastrototaro et al. |
| 2021/0275742 A1 | 9/2021 | Montero et al. |
| 2021/0294723 A1 | 9/2021 | Salameh et al. |
| 2021/0306031 A1 | 9/2021 | Miller et al. |
| 2021/0315525 A1 | 10/2021 | Mairs et al. |
| 2021/0321942 A1 | 10/2021 | Pushpala et al. |
| 2021/0321950 A1 | 10/2021 | Fennell |
| 2021/0322676 A1 | 10/2021 | Hayter et al. |
| 2021/0330219 A1 | 10/2021 | Ma et al. |
| 2021/0338116 A1 | 11/2021 | Acciaroli et al. |
| 2021/0343402 A1 | 11/2021 | Acciaroli et al. |
| 2021/0345880 A1 | 11/2021 | DeHennis et al. |
| 2021/0345915 A1 | 11/2021 | Shenar |
| 2021/0361196 A1 | 11/2021 | Hayter et al. |
| 2021/0361198 A1 | 11/2021 | Brister et al. |
| 2021/0366579 A1 | 11/2021 | Budiman |
| 2021/0366609 A1 | 11/2021 | Nabutovsky et al. |
| 2021/0369149 A1 | 12/2021 | Böhm et al. |
| 2021/0369151 A1 | 12/2021 | Derdzinski et al. |
| 2021/0375447 A1 | 12/2021 | Derdzinski et al. |
| 2021/0375448 A1 | 12/2021 | Derdzinski et al. |
| 2021/0378563 A1 | 12/2021 | Derdzinski et al. |
| 2021/0379370 A1 | 12/2021 | Windmiller et al. |
| 2021/0383925 A1 | 12/2021 | Wexler et al. |
| 2021/0386331 A1 | 12/2021 | Hossein Yazdi et al. |
| 2021/0386334 A1 | 12/2021 | Hoss et al. |
| 2021/0386335 A1 | 12/2021 | Varsavsky et al. |
| 2021/0391081 A1 | 12/2021 | Goldner et al. |
| 2021/0393130 A1 | 12/2021 | DeHennis et al. |
| 2021/0393201 A1 | 12/2021 | Morelock et al. |
| 2021/0398662 A1 | 12/2021 | Strom et al. |
| 2021/0407664 A1 | 12/2021 | Greene et al. |
| 2022/0000433 A1 | 1/2022 | Hayter et al. |
| 2022/0008017 A1 | 1/2022 | Ou et al. |
| 2022/0031209 A1 | 2/2022 | Windmiller et al. |
| 2022/0031244 A1 | 2/2022 | Windmiller et al. |
| 2022/0039700 A1 | 2/2022 | Wu et al. |
| 2022/0039701 A1 | 2/2022 | Wu et al. |
| 2022/0039702 A1 | 2/2022 | Wu et al. |
| 2022/0039703 A1 | 2/2022 | Wedekind et al. |
| 2022/0039704 A1 | 2/2022 | Southerland, III et al. |
| 2022/0039709 A1 | 2/2022 | Wu |
| 2022/0039755 A1 | 2/2022 | Mikhno et al. |
| 2022/0039756 A1 | 2/2022 | Mikhno et al. |
| 2022/0044808 A1 | 2/2022 | Jennings et al. |
| 2022/0047187 A1 | 2/2022 | Yang et al. |
| 2022/0061707 A1 | 3/2022 | Southerland, III et al. |
| 2022/0061710 A1 | 3/2022 | Hadley et al. |
| 2022/0061711 A1 | 3/2022 | Nakatsugawa et al. |
| 2022/0061712 A1 | 3/2022 | Jepson et al. |
| 2022/0061774 A1 | 3/2022 | Jepson et al. |
| 2022/0061775 A1 | 3/2022 | Jepson et al. |
| 2022/0068473 A1 | 3/2022 | Miller et al. |
| 2022/0071519 A1 | 3/2022 | Sparacino et al. |
| 2022/0071522 A1 | 3/2022 | Hirata et al. |
| 2022/0071530 A1 | 3/2022 | Boock et al. |
| 2022/0084649 A1 | 3/2022 | Anderson et al. |
| 2022/0087576 A1 | 3/2022 | Scott et al. |
| 2022/0095964 A1 | 3/2022 | Nishida et al. |
| 2022/0095965 A1 | 3/2022 | Wang et al. |
| 2022/0095968 A1 | 3/2022 | Wang et al. |
| 2022/0096021 A1 | 3/2022 | Zhong et al. |
| 2022/0104761 A1 | 4/2022 | Zhong et al. |
| 2022/0105269 A1 | 4/2022 | Zhong et al. |
| 2022/0117523 A1 | 4/2022 | Feldman et al. |

(56) References Cited

U.S. PATENT DOCUMENTS

| | | |
|---|---|---|
| 2022/0118180 A1 | 4/2022 | Sloan et al. |
| 2022/0125348 A1 | 4/2022 | Jacks et al. |
| 2022/0125352 A1 | 4/2022 | Varsavsky et al. |
| 2022/0125355 A1 | 4/2022 | Kamath et al. |
| 2022/0125357 A1 | 4/2022 | Kamath et al. |
| 2022/0133179 A1 | 5/2022 | Yang et al. |
| 2022/0133998 A1 | 5/2022 | Chattaraj et al. |
| 2022/0142519 A1 | 5/2022 | Hayter et al. |
| 2022/0142521 A1 | 5/2022 | Russo |
| 2022/0142522 A1 | 5/2022 | Russo |
| 2022/0142523 A1 | 5/2022 | Love et al. |
| 2022/0151516 A1 | 5/2022 | Wang et al. |
| 2022/0160265 A1 | 5/2022 | Sankhala et al. |
| 2022/0165432 A1 | 5/2022 | Pickus et al. |
| 2022/0167891 A1 | 6/2022 | Simpson et al. |
| 2022/0175278 A1 | 6/2022 | Campbell et al. |
| 2022/0189630 A1 | 6/2022 | Gee et al. |
| 2022/0189631 A1 | 6/2022 | Gee et al. |
| 2022/0192610 A1 | 6/2022 | McGarraugh |
| 2022/0197628 A1 | 6/2022 | Kiaie et al. |
| 2022/0202290 A1 | 6/2022 | Hua et al. |
| 2022/0208371 A1 | 6/2022 | Budiman |
| 2022/0211302 A1 | 7/2022 | Ajemba et al. |
| 2022/0211303 A1 | 7/2022 | Hayter et al. |
| 2022/0211307 A1 | 7/2022 | Budiman et al. |
| 2022/0225901 A1 | 7/2022 | Chapman et al. |
| 2022/0225907 A1 | 7/2022 | Peyser et al. |
| 2022/0233108 A1 | 7/2022 | Ajemba et al. |
| 2022/0233109 A1 | 7/2022 | Ajemba et al. |
| 2022/0233110 A1 | 7/2022 | Harper et al. |
| 2022/0233111 A1 | 7/2022 | Harper et al. |
| 2022/0233152 A1 | 7/2022 | Cappon et al. |
| 2022/0236252 A1 | 7/2022 | Hayter et al. |
| 2022/0240818 A1 | 8/2022 | Ajemba et al. |
| 2022/0240821 A1 | 8/2022 | Harper et al. |
| 2022/0240867 A1 | 8/2022 | Huhta et al. |
| 2022/0245306 A1 | 8/2022 | Ajemba et al. |
| 2022/0248988 A1 | 8/2022 | Kumar et al. |
| 2022/0249002 A1 | 8/2022 | Chapman et al. |
| 2022/0249779 A1 | 8/2022 | Hayter et al. |
| 2022/0257151 A1 | 8/2022 | Lee et al. |
| 2022/0262475 A1 | 8/2022 | Nogueira et al. |
| 2022/0265179 A1 | 8/2022 | Liu et al. |
| 2022/0265181 A1 | 8/2022 | Feldman |
| 2022/0273197 A1 | 9/2022 | Lee |
| 2022/0273198 A1 | 9/2022 | Nogueira et al. |
| 2022/0273204 A1 | 9/2022 | Kamath et al. |
| 2022/0280122 A1 | 9/2022 | Dunn et al. |
| 2022/0287601 A1 | 9/2022 | Harper |
| 2022/0287652 A1 | 9/2022 | Budiman et al. |
| 2022/0313173 A1 | 10/2022 | Sparacino et al. |
| 2022/0322976 A1 | 10/2022 | Edla et al. |
| 2022/0354392 A1 | 11/2022 | Davies |
| 2022/0354395 A1 | 11/2022 | Frank et al. |
| 2022/0359074 A1 | 11/2022 | Bernstein et al. |
| 2022/0361778 A1 | 11/2022 | Jepson et al. |
| 2022/0361779 A1 | 11/2022 | Parker et al. |
| 2022/0361780 A1 | 11/2022 | Erraguntla et al. |
| 2022/0361781 A1 | 11/2022 | Masciotti et al. |
| 2022/0361823 A1 | 11/2022 | Goldner et al. |
| 2022/0369961 A1 | 11/2022 | Mothilal et al. |
| 2022/0370011 A1 | 11/2022 | Windmiller et al. |
| 2022/0378315 A1 | 12/2022 | Varsavsky et al. |
| 2022/0378659 A1 | 12/2022 | Vleugels |
| 2022/0386903 A1 | 12/2022 | Scott et al. |
| 2022/0395199 A1 | 12/2022 | Garai et al. |
| 2022/0400985 A1 | 12/2022 | Gonzales et al. |
| 2022/0400986 A1 | 12/2022 | Khanal et al. |
| 2022/0401041 A1 | 12/2022 | Harper et al. |
| 2022/0409102 A1 | 12/2022 | Taub et al. |
| 2023/0000402 A1 | 1/2023 | Ajemba et al. |
| 2023/0000447 A1 | 1/2023 | Mikhno et al. |
| 2023/0001090 A1 | 1/2023 | Sloan et al. |
| 2023/0004815 A1 | 1/2023 | Gee et al. |
| 2023/0005589 A1 | 1/2023 | Monirabbasi et al. |
| 2023/0074798 A1 | 3/2023 | Tangney et al. |
| 2023/0094419 A1 | 3/2023 | Mansfield, III et al. |
| 2023/0099617 A1 | 3/2023 | Mansfield, III et al. |
| 2023/0137258 A1 | 5/2023 | Windmiller |
| 2023/0190147 A1 | 6/2023 | Campbell et al. |
| 2023/0256220 A1 | 8/2023 | Mansfield, III et al. |
| 2023/0301552 A1 | 9/2023 | Mallires et al. |
| 2023/0310823 A1 | 10/2023 | Mansfield et al. |
| 2023/0414102 A1 | 12/2023 | Allen et al. |

FOREIGN PATENT DOCUMENTS

| | | |
|---|---|---|
| WO | WO-2020197968 A1 | 10/2020 |
| WO | WO-2020257069 A1 | 12/2020 |
| WO | WO-2021086690 A1 | 5/2021 |
| WO | WO-2021119546 A1 | 6/2021 |
| WO | WO-2021165946 A1 | 8/2021 |
| WO | WO-2021257624 A1 | 12/2021 |
| WO | WO-2022010812 A1 | 1/2022 |
| WO | WO-2022025411 A1 | 2/2022 |
| WO | WO-2022026764 A1 | 2/2022 |
| WO | WO-2022029164 A1 | 2/2022 |
| WO | WO-2022053764 A1 | 3/2022 |
| WO | WO-2022120239 A1 | 6/2022 |
| WO | WO-2022131467 A1 | 6/2022 |
| WO | WO-2022131472 A1 | 6/2022 |
| WO | WO-2022146496 A1 | 7/2022 |
| WO | WO-2022180130 A1 | 9/2022 |
| WO | WO-2022192827 A1 | 9/2022 |
| WO | WO-2022235556 A1 | 11/2022 |
| WO | WO-2022240700 A1 | 11/2022 |
| WO | WO-2022244963 A1 | 11/2022 |
| WO | WO-2022245804 A1 | 11/2022 |
| WO | WO-2023055755 A1 | 4/2023 |
| WO | WO-2023064877 A1 | 4/2023 |
| WO | WO-2023133468 A1 | 7/2023 |
| WO | WO-2023229662 A2 | 11/2023 |
| WO | WO-2024010827 A1 | 1/2024 |

OTHER PUBLICATIONS

Al Hayek et al., "Patient Satisfaction and Clinical Efficacy of Novel Blood Glucose Meters Featuring Color Range Indicators in Patients With Type 2 Diabetes: A Prospective Study" Cureus Oct. 27, 2020; 12(10):e11195. doi: 10.7759/cureus.11195.

Allen et al., "Continuous glucose monitoring counseling improves physical activity behaviors of individuals with type 2 diabetes: A randomized clinical trial" Diabetes Res Clin Pract. Jun. 2008; 80(3): 371-379. doi:10.1016/j.diabres.2008.01.006.

American Diabetes Association® Press Release (2020). "American Diabetes Association ® Applauds policymakers' Focus on Addressing High Costs of Insulin for Seven Million Americans," 4 pages.

Bantle, J.P. et al. (1997). "Glucose measurement in patients with diabetes mellitus with dermal interstitial fluid," J. Lab. Clin. Med. 130:436-441.

Barrett et al., "Risk for Newly Diagnosed Diabetes 30 Days After SARS-CoV-2 Infection Among Persons Aged 18 Years—United States, Mar. 1, 2020-Jun. 28, 2021" MMWR Morb Mortal Wkly Rep. Jan. 14, 2022; 71(2):59-65. doi: 10.15585/mmwr.mm7102e2.

Beckles, G.L. et al. (2016). "Disparities in the prevalence of diagnosed diabetes—United States, 1999-2002 and 2011-2014," MMWR 65:1265-1269.

Cao, J. et al. (2017). "Validation of capillary blood analysis and capillary testing mode on the epoc Point of Care system," Pract. Lab. Med. 9:24-27.

Castle, J.R. et al. (2012). "The accuracy benefit of multiple amperometric glucose sensors in people with type 1 diabetes," Diabetes Care 35:706-710.

Centers for Disease Control, "National Diabetes Statistics Report 2020 Estimates of Diabetes and Its Burden in the United States" (2020) 32 pages.

DEXCOM (2020). Analyst Day Presentation, 19 total pages.

DEXCOM (2020). Analyst Day Presentation, 27 total pages.

Diabetes Care (2021). "7. Diabetes Technology: Standards of Medical Care in Diabetes—2021," Diabetes Care 44(Supplement 1):S85-S99.

(56) References Cited

OTHER PUBLICATIONS

Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.

Ehrhardt et al., "Behavior Modification in Prediabetes and Diabetes: Potential Use of Real-Time Continuous Glucose Monitoring" Journal of Diabetes Science and Technology Mar. 2019; 13(2):271-275.

Ehrhardt et al., "Continuous Glucose Monitoring As a Behavior Modification Tool" Clin Diabetes. Apr. 2020; 38(2):126-131. doi: 10.2337/cd19-0037.

Ehrhardt et al, "The Effect of Real-Time Continuous Glucose Monitoring on Glycemic Control in Patients with Type 2 Diabetes Mellitus" Journal of Diabetes Science and Technology May 2011; 5(3):668-675.

Fang, M. et al. (2021). "Trends in Diabetes Treatment and Control in U.S. Adults, 1999-2018," N. Engl. Med. 384:2219-2228.

Fonda et al., "The Cost-Effectiveness of Real-Time Continuous Glucose Monitoring (RT-CGM) in Type 2 Diabetes" Journal of Diabetes Science and Technology (2016) 10(4):898-904.

French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.

Grady, M. et al. (2017). "Examining the Impact of a Novel Blood Glucose Monitor with Color Range Indicator on Decision-Making in Patients With Type 1 and Type 2 Diabetes and its Association With Patient Numeracy Level," JMIR Diabetes 2:e24. 11 pages.

Grady, M. et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.

Groenendaal, W. et al. (2008). "Modeling Glucose and Water Dynamics in Human Skin," Diab. Tech. Therap. 10:283-293.

Han et al., "The End of the Road for the YSI 2300 Analyzer: Where Do We Go Now?" Journal of Diabetes Science and Technology (2020) 14(3):595-600.

Han et al., "The YSI 2300 Analyzer Replacement Meeting Report" Journal of Diabetes Science and Technology (2020) 14(3):679-686.

Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.

Karter, A.J. et al. (2021). "Association of Real-time Continuous Glucose Monitoring With Glycemic Control and Acute Metabolic Events Among Patients With Insulin-Treated Diabetes," JAMA 325:2273-2284.

Martens, T. et al. (2021). "Effect of Continuous Glucose Monitoring on Glycemic Control in Patients with Type 2 Diabetes Treated with Basal Insulin a Randomized Clinical Trial," JAMA 325:2262-2272.

McClatchey, P.M. et al. (2019). "Fibrotic Encapsulation Is the Dominant Source of Continuous Glucose Monitor Delays," Diabetes 68:1892-1901.

Neerken, S. et al. (2004). "Characterization of age-related effects in human skin: A comparative study that applies confocal laser scanning microscopy and optical coherence tomography," J. Biomed. Optics 9:274-281.

Polonsky, W.H. et al. (2011). "A survey of blood glucose monitoring in patients with type 2 diabetes: Are recommendations from health care professionals being followed?" Curr. Med. Res. & Opinion 27:31-37.

Rigla, M. et al. (2018). "Human Subcutaneous Tissue Response to Glucose Sensors: Macrophages Accumulation Impact on Sensor Accuracy," Diabetes Technology & Therapeutics 20:296-302.

Sharifi et al., "Redundancy in Glucose Sensing: Enhanced Accuracy and Reliability of an Electrochemical Redundant Sensor for Continuous Glucose Monitoring" Journal of Diabetes Science and Technology (2016) 10(3):669-678.

Sheikh, Z. et al. (2015). "Macrophages, Foreign Body Giant Cells and Their Response to Implantable Biomaterials," Materials 8:5671-5701.

Shi, T. et al. (2016). "Modeling and Measurement of Correlation between Blood and Interstitial Glucose Changes," J. Diab. Res. vol. 2016, 9 pages.

Turner et al., "Intensive blood-glucose control with sulphonylureas or insulin compared with conventional treatment and risk of complications in patients with type 2 diabetes (UKPDS 33)" The Lancet Sep. 1998; 352(9131):837-853.

Vigersky et al., "Short- and Long-Term Effects of Real-Time Continuous Glucose Monitoring in Patients with Type 2 Diabetes" Diabetes Care Jan. 2012; 35:32-38.

Wolicki et al., "Epidemiology and Prevention of Vaccine-Preventable Diseases: Chapter 6: Vaccine Administration" Centers for Disease Control and Prevention (2021) 17 pages.

World Health Organization, "Diabetes", Sep. 16, 2022, 5 pages.

Young et al., "Glucose Self-monitoring in Non-Insulin-Treated Patients With Type 2 Diabetes in Primary Care Settings: A Randomized Trial" JAMA Intern Med. Jul. 2017; 177(7):920-929.

Invitation to Pay Additional Fees and, Where Applicable, Protest Fee mailed on Oct. 24, 2023, for PCT Application No. PCT/US2023/026957, filed on Jul. 5, 2023, 19 pages.

International Search Report and Written Opinion mailed on Dec. 15, 2023, for PCT Application No. PCT/US2023/026957, 23 pages.

\* cited by examiner

SENSOR ASSEMBLY OF A MICRONEEDLE ARRAY-BASED CONTINUOUS ANALYTE MONITORING DEVICE

CROSS-REFERENCE TO RELATED APPLICATIONS

This application claims priority to U.S. Provisional Patent Application No. 63/358,459, filed Jul. 5, 2022, the contents of which are hereby incorporated in their entirety by this reference.

TECHNICAL FIELD

This invention relates generally to the field of analyte monitoring, such as continuous glucose monitoring.

BACKGROUND

Diabetes is a chronic disease in which the body does not produce or properly utilize insulin, a hormone that regulates blood glucose. Insulin may be administered to a diabetic patient to help regulate blood glucose levels, though blood glucose levels must nevertheless be carefully monitored to help ensure that timing and dosage are appropriate. Without proper management of their condition, diabetic patients may suffer from a variety of complications resulting from hyperglycemia (high blood sugar levels) or hypoglycemia (low blood sugar levels).

Blood glucose monitors help diabetic patients manage their condition by measuring blood glucose levels from a sample of blood. For example, a diabetic patient may obtain a blood sample through a fingerstick sampling mechanism, transfer the blood sample to a test strip with suitable reagent(s) that react with the blood sample, and use a blood glucose monitor to analyze the test strip to measure glucose level in that blood sample. However, a patient using this process can typically only measure his or her glucose levels at discrete instances in time, which may fail to capture a hyperglycemia or hypoglycemia condition in a timely manner. Yet a more recent variety of glucose monitor is a continuous glucose monitor (CGM) device, which includes implantable transdermal electrochemical sensors that are used to continuously detect and quantify blood glucose levels by proxy measurement of glucose levels in the subcutaneous interstitial fluid. However, conventional CGM devices also have weaknesses including tissue trauma from insertion and signal latency (e.g., due to the time required for the glucose analyte to diffuse from capillary sources to the sensor). These weaknesses also lead to a number of drawbacks, such as pain experienced by the patient when electrochemical sensors are inserted, and limited accuracy in glucose measurements, particularly when blood glucose levels are changing rapidly. Accordingly, there is a need for a new and improved analyte monitoring system.

SUMMARY

In some variations, a method of operating an analyte monitoring device configured to be inserted into skin of a user includes determining, by a controller of the analyte monitoring device, a source of a power-on event, the source of the power-on event being a connection with a battery or power received from an energy harvesting module and transitioning the analyte monitoring device to a mode of operation corresponding to the determined source of the power-on event. When the determined source of the power-on event is the connection with the battery, the corresponding mode of operation includes a start-up mode, and when the source of the power-on event is the power received from the energy harvesting module, the corresponding mode of operation includes a reset mode.

In some variations, an analyte monitoring device includes a microneedle array configured to be inserted into skin of a user and obtain analog current measurements, a battery, an energy harvesting module, and a controller configured to determine a source of a power-on event, the source of the power-on event being a connection with the battery or power received from the energy harvesting module, and transition the analyte monitoring device to a mode of operation corresponding to the determined source of the power-on event. When the determined source of the power-on event is the connection with the battery, the corresponding mode of operation includes a start-up mode, and when the source of the power-on event is the power received from the energy harvesting module, the corresponding mode of operation includes a reset mode.

In some variations, a method of operating an analyte monitoring device configured to be inserted into skin of a user includes determining, by a controller of the analyte monitoring device, that a power-on event is a valid power-on event, where the valid power-on event includes a transition of the analyte monitoring device to a usable state or an intentional positioning of the analyte monitoring device in a communication field, and after determining the power-on event is the valid power-on event, transitioning the analyte monitoring device to a mode corresponding to the respective valid power-on event.

In some variations, an analyte monitoring device includes a microneedle array configured to be inserted into skin of a user and obtain analog current measurements, and a controller configured to determine that a power-on event is a valid power-on event, where the valid power-on event includes a transition of the analyte monitoring device to a usable state or an intentional positioning of the analyte monitoring device in a communication field, and after determining the power-on event is the valid power-on event, transition the analyte monitoring device to a mode corresponding to the respective valid power-on event.

In some variations, a method of operating an analyte monitoring device configured to be inserted into skin of a user includes determining, by a controller of the analyte monitoring device, that a power-on event is a valid power-on event by identifying if the analyte monitoring device is in a usable state, and responsive to determining the power-on event is the valid power-on event, transitioning the analyte monitoring device to an idle mode.

In some variations, an analyte monitoring device includes a microneedle array configured to be inserted into skin of a user and obtain analog current measurements, and a controller configured to determine that a power-on event is a valid power-on event by identifying if the analyte monitoring device is in a usable state, and responsive to determining the power-on event is the valid power-on event, transition the analyte monitoring device to an idle mode.

In some variations, a sensor assembly of an analyte monitoring device includes a microneedle array assembly and an electronics assembly. The microneedle array assembly may include a microneedle array configured to obtain analog current measurements indicative of a concentration of an analyte. The electronics assembly may include a power source, an analog front end configured to convert the analog current measurements to digital values, a microcontroller configured to process the digital values, a power connect circuit including a switch configured to couple the power source to the microcontroller and to the analog front end, and a photo detect circuit configured to generate, in response to a triggering event, a signal to the power connect circuit, the signal including an instruction to close the switch thereby establishing a connection between the power source and the microcontroller and between the power source and the analog front end. Connection between the photo detect circuit and the power connect circuit may be established upon a connection between the microneedle array assembly and the electronics assembly.

In some variations, a method may include establishing, in an analyte monitoring device including a microneedle array, a connection between a power connect circuit and a photo detect circuit, the power connect circuit including a switch configured to establish a connection between a power source and a microcontroller and the power source and an analog front end, establishing, in response to a triggering event, a connection between the power source and the microcontroller and a connection between the power source and the analog front end, the triggering event detected by the photo detect circuit, confirming insertion of the microneedle array into skin of a user, and transitioning, in response to insertion of the microneedle array, the analog front end to active sensing.

In some variations, a method of operating an analyte monitoring device configured to be inserted into skin of a user includes applying by an analog front end of the analyte monitoring device a first bias potential, the first bias potential applied between a first working electrode and a reference point, measuring a first resulting current at the first working electrode, applying, by the analog front end, a second bias potential, the second bias potential applied between a second working electrode and the reference point, measuring a second resulting current at the second working electrode, and responsive to a determination that at least one of the first resulting current and the second resulting current is within a predetermined threshold, transitioning the analyte monitoring device to an operational mode during which an operating bias potential is applied. The analyte monitoring device includes a microneedle array including at least two working electrodes, a reference electrode, and a counter electrode, each positioned on respective microneedles of the microneedle array.

In some variations, a method of operating an analyte monitoring device configured to be inserted into skin of a user includes applying by an analog front end of the analyte monitoring device a first bias potential, the first bias potential applied between a first working electrode and a reference point, measuring a first resulting current at the first working electrode, responsive to a determination that the first resulting current is within a predetermined threshold, transitioning the analyte monitoring device to an operational mode during which an operating bias potential is applied, and in the operational mode, applying the operating bias potential to at least a second working electrode. The analyte monitoring device includes a microneedle array including at least two working electrodes, a reference electrode, and a counter electrode, each positioned on respective microneedles of the microneedle array.

DETAILED DESCRIPTION

Non-limiting examples of various aspects and variations of the invention are described herein and illustrated in the accompanying drawings.

Aspects of the current subject matter are directed to a sensor assembly including one or more microneedle arrays of an analyte monitoring device. More particularly, aspects are directed to components and architecture of a sensor assembly to implement power and processing aspects of a microneedle array-based continuous analyte monitoring device for the detection and measuring of an analyte.

As generally described herein, an analyte monitoring system may include an analyte monitoring device that is worn by a user and includes one or more sensors for monitoring at least one analyte of a user. The sensors may, for example, include one or more electrodes configured to perform electrochemical detection of at least one analyte. The analyte monitoring device may communicate sensor data to an external computing device for storage, display, and/or analysis of sensor data.

Figure 1:
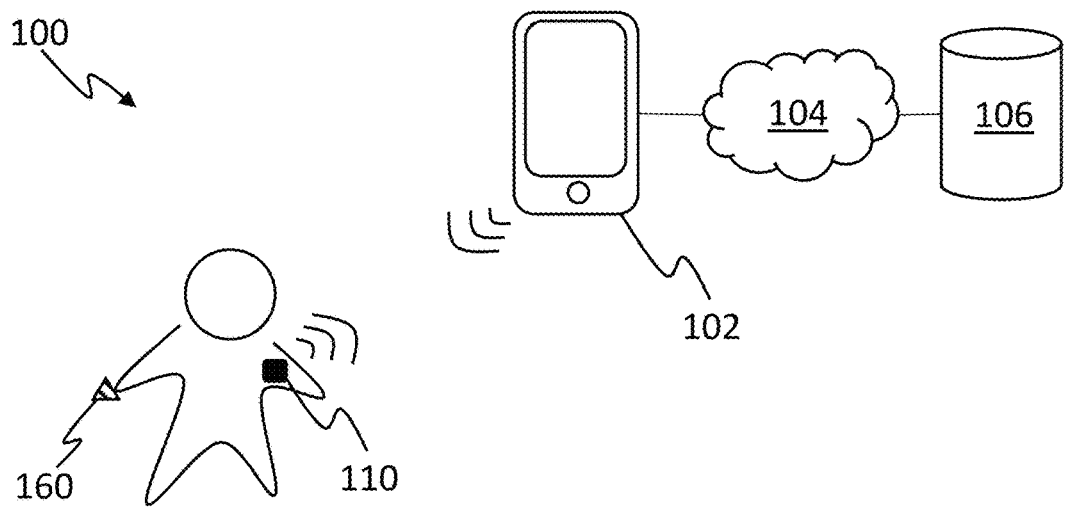
FIG. 1 depicts an illustrative schematic of an analyte monitoring system with a microneedle array.

For example, as shown in FIG. 1, an analyte monitoring system 100 may include an analyte monitoring device 110 that is worn by a user. The analyte monitoring device 110 may be a continuous analyte monitoring device (e.g., continuous glucose monitoring device). The analyte monitoring device 110 may include, for example, a microneedle array comprising at least one electrochemical sensor for detecting and/or measuring one or more analytes in body fluid of a user. In some variations, the analyte monitoring device 110 may be applied to the user using suitable applicator 160, or, in some variations, the analyte monitoring device 110 may be applied manually. The analyte monitoring device 110 may include one or more processors for performing analysis on sensor data, and/or a communication module (e.g., wireless communication module) configured to communicate sensor data to a mobile computing device 102 (e.g., smartphone) or other suitable computing device. In some variations, the mobile computing device 102 may include one or more processors executing a mobile application to handle sensor data (e.g., displaying data, analyzing data for trends, etc.) and/or provide suitable alerts or other notifications related to the sensor data and/or analysis thereof. While in some variations the mobile computing device 102 may perform sensor data analysis locally, other computing device(s) may alternatively or additionally remotely analyze sensor data and/or communicate information related to such analysis with the mobile computing device 102 (or other suitable user interface) for display to the user. Furthermore, in some variations the mobile computing device 102 may be configured to communicate sensor data and/or analysis of the sensor data over a network 104 to one or more storage devices 106 (e.g., server) for archiving data and/or other suitable information related to the user of the analyte monitoring device 110.

The analyte monitoring devices described herein have characteristics that improve a number of properties that are advantageous for a continuous analyte monitoring device such as a continuous glucose monitoring (CGM) device. For example, the analyte monitoring device described herein have improved sensitivity (amount of sensor signal produced per given concentration of target analyte), improved selectivity (rejection of endogenous and exogenous circulating compounds that can interfere with the detection of the target analyte), and improved stability to help minimize change in sensor response over time through storage and operation of the analyte monitoring device. Additionally, compared to conventional continuous analyte monitoring devices, the analyte monitoring devices described herein have a shorter warm-up time that enables the sensor(s) to quickly provide a stable sensor signal following implantation, as well as a short response time that enables the sensors(s) to quickly provide a stable sensor signal following a change in analyte concentration in the user. Furthermore, as described in further detail below, the analyte monitoring devices described herein may be applied to and function in a variety of wear sites and provide for pain-free sensor insertion for the user. Other properties such as biocompatibility, sterilizability, and mechanical integrity are also optimized in the analyte monitoring devices described herein.

Although the analyte monitoring systems described herein may be described with reference to monitoring of glucose (e.g., in users with Type 2 diabetes, Type 1 diabetes), such systems may additionally or alternatively be configured to sense and monitor other suitable analytes. As described in further detail below, suitable target analytes for detection may, for example, include glucose, ketones, lactate, and cortisol. One target analyte may be monitored, or multiple target analytes may be simultaneously monitored (e.g., in the same analyte monitoring device). For example, monitoring of other target analytes may enable the monitoring of other indications such as stress (e.g., through detection of rising cortisol and glucose) and ketoacidosis (e.g., through detection of rising ketones).

Various aspects of example variations of the analyte monitoring device, the analyte monitoring system, and methods of use thereof, are described in further detail below.

Figure 2A:
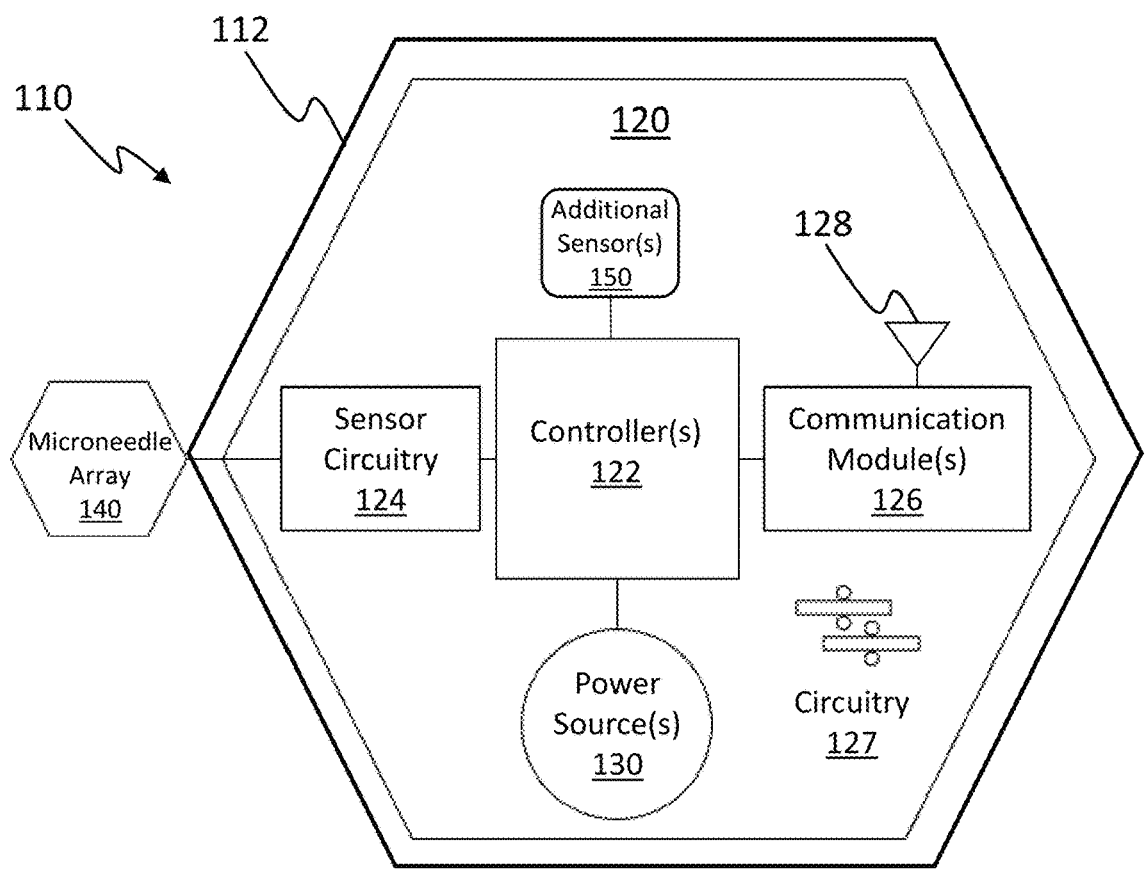
FIG. 2A depicts an illustrative schematic of an analyte monitoring device.

As shown in FIG. 2A, in some variations, an analyte monitoring device 110 may generally include a housing 112 and a microneedle array 140 extending outwardly from the housing 112. The housing 112, may, for example, be a wearable housing configured to be worn on the skin of a user such that the microneedle array 140 extends at least partially into the skin of the user. For example, the housing 112 may include an adhesive such that the analyte monitoring device 110 is a skin-adhered patch that is simple and straightforward for application to a user. The microneedle array 140 may be configured to puncture the skin of the user and include one or more electrochemical sensors (e.g., electrodes) configured for measuring one or more target analytes that are accessible after the microneedle array 140 punctures the skin of the user. In some variations, the analyte monitoring device 110 may be integrated or self-contained as a single unit, and the unit may be disposable (e.g., used for a period of time and replaced with another instance of the analyte monitoring device 110).

An electronics system 120 may be at least partially arranged in the housing 112 and include various electronic components, such as sensor circuitry 124 configured to perform signal processing (e.g., biasing and readout of electrochemical sensors, converting the analog signals from the electrochemical sensors to digital signals, etc.). The electronics system 120 may also include at least one microcontroller 122 for controlling the analyte monitoring device 110, at least one communication module 126, at least one power source 130, and/or other various suitable passive circuitry 127. The microcontroller 122 may, for example, be configured to interpret digital signals output from the sensor circuitry 124 (e.g., by executing a programmed routine in firmware), perform various suitable algorithms or mathematical transformations (e.g., calibration, etc.), and/or route processed data to and/or from the communication module 124. In some variations, the communication module 126 may include a suitable wireless transceiver (e.g., a Bluetooth transceiver, a near field communication antenna, or the like) for communicating data with an external computing device 102 via one or more antennas 128. For example, the communication module 126 may be configured to provide uni-directional and/or bi-directional communication of data with an external computing device 102 that is paired with the analyte monitoring device 110. The power source 130 may provide power for the analyte monitoring device 110, such as for the electronics system. The power source 130 may include a battery or other suitable source, and may, in some variations, be rechargeable and/or replaceable. Passive circuitry 127 may include various non-powered electrical circuitry (e.g., resistors, capacitors, inductors, etc.) providing interconnections between other electronic components, etc. The passive circuitry 127 may be configured to perform noise reduction, biasing and/or other purposes, for example. In some variations, the electronic components in the electronics system 120 may be arranged on one or more printed circuit boards (PCB), which may be rigid, semi-rigid, or flexible, for example. Additional details of the electronics system 120 are described further below.

In some variations, the analyte monitoring device 110 may further include one or more additional sensors 150 to provide additional information that may be relevant for user monitoring. For example, the analyte monitoring device 110 may further include at least one temperature sensor (e.g., a thermistor) configured to measure skin temperature, thereby enabling temperature compensation for the sensor measurements obtained by the microneedle array electrochemical sensors.

As shown in the schematic of FIG. 2A of an analyte monitoring device 110, the electronics system 120 may be integrated within the housing 112, such that the electronics system 120 may be combined with sensing elements (e.g., the microneedle array 140) as part of a single unit, in contrast to traditional CGM systems, which typically incorporate components in multiple physically distinct units.

Figure 2B:
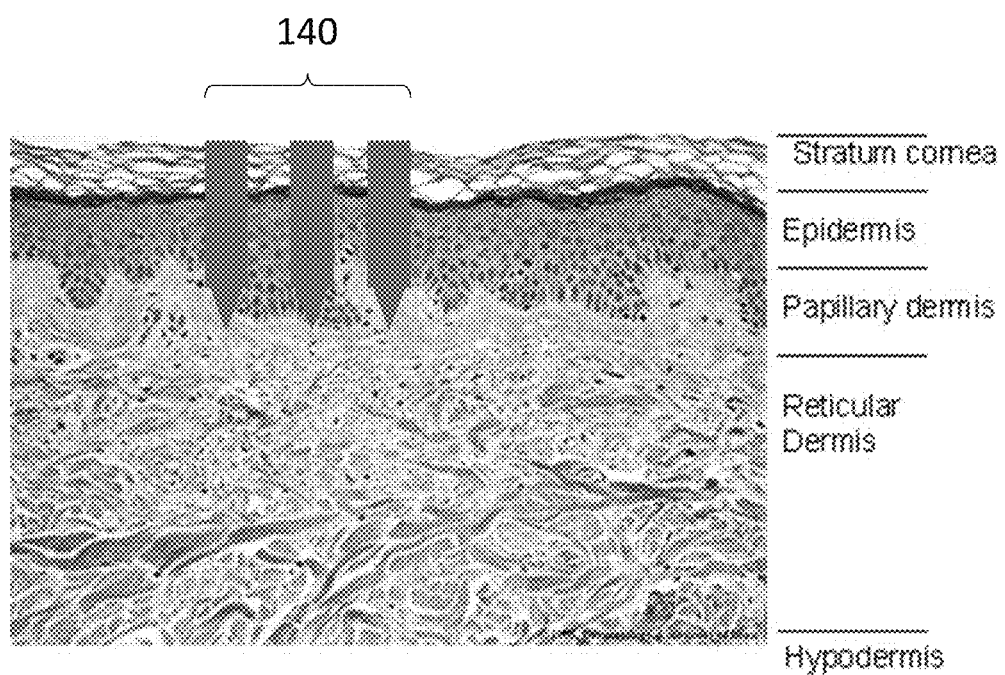
FIG. 2B depicts an illustrative schematic of microneedle insertion depth in an analyte monitoring device.

In some variations, the microneedle array 140 in the analyte monitoring device 110 may be configured to puncture skin of a user. As shown in FIG. 2B, when the device 110 is worn by the user, the microneedle array 140 may extend into the skin of the user such that electrodes on distal regions of the microneedles rest in the dermis. Specifically, in some variations, the microneedles may be designed to penetrate the skin and access the upper dermal region (e.g., papillary dermis and upper reticular dermis layers) of the skin, in order to enable the electrodes to access interstitial fluid that surrounds the cells in these layers. For example, in some variations, the microneedles may have a height generally ranging between at least 350 μm and about 515 μm. In some variations, one or more microneedles may extend from the housing such that a distal end of the electrode on the microneedle is located less than about 5 mm from a skin-interfacing surface of the housing, less than about 4 mm from the housing, less than about 3 mm from the housing, less than about 2 mm from the housing, or less than about 1 mm from the housing.

In contrast to traditional continuous analyte monitoring devices (e.g., CGM devices), which include sensors typically implanted between about 8 mm and about 10 mm beneath the skin surface in the subcutis or adipose layer of the skin, the analyte monitoring device 110 has a shallower microneedle insertion depth of about 0.25 mm (such that electrodes are implanted in the upper dermal region of the skin) that provides numerous benefits. These benefits include access to dermal interstitial fluid including one or more target analytes for detection, which is advantageous at least because at least some types of analyte measurements of dermal interstitial fluid have been found to closely correlate to those of blood. For example, it has been discovered that glucose measurements performed using electrochemical sensors accessing dermal interstitial fluid are advantageously highly linearly correlated with blood glucose measurements. Accordingly, glucose measurements based on dermal interstitial fluid are highly representative of blood glucose measurements.

Additionally, because of the shallower microneedle insertion depth of the analyte monitoring device 110, a reduced time delay in analyte detection is obtained compared to traditional continuous analyte monitoring devices. Such a shallower insertion depth positions the sensor surfaces in close proximity (e.g., within a few hundred micrometers or less) to the dense and well-perfused capillary bed of the reticular dermis, resulting in a negligible diffusional lag from the capillaries to the sensor surface. Diffusion time is related to diffusion distance according to $t=x^2/(2D)$ where t is the diffusion time, x is the diffusion distance, and D is the mass diffusivity of the analyte of interest. Therefore, positioning an analyte sensing element twice as far away from the source of an analyte in a capillary will result in a quadrupling of the diffusional delay time. Accordingly, conventional analyte sensors, which reside in the very poorly vascularized adipose tissue beneath the dermis, result in a significantly greater diffusion distance from the vasculature in the dermis and thus a substantial diffusional latency (e.g., typically 5-20 minutes). In contrast, the shallower microneedle insertion depth of the analyte monitoring device 110 benefits from low diffusional latency from capillaries to the sensor, thereby reducing time delay in analyte detection and providing more accurate results in real-time or near real-time. For example, in some embodiments, diffusional latency may be less than 10 minutes, less than 5 minutes, or less than 3 minutes.

Furthermore, when the microneedle array rests in the upper dermal region, the lower dermis beneath the microneedle array includes very high levels of vascularization and perfusion to support the dermal metabolism, which enables thermoregulation (via vasoconstriction and/or vasodilation) and provides a barrier function to help stabilize the sensing environment around the microneedles. Yet another advantage of the shallower insertion depth is that the upper dermal layers lack pain receptors, thus resulting in a reduced pain sensation when the microneedle array punctures the skin of the user, and providing for a more comfortable, minimally-invasive user experience.

Thus, the analyte monitoring devices and methods described herein enable improved continuous monitoring of one or more target analytes of a user. For example, as described above, the analyte monitoring device may be simple and straightforward to apply, which improves ease-of-use and user compliance. Additionally, analyte measurements of dermal interstitial fluid may provide for highly accurate analyte detection. Furthermore, compared to traditional continuous analyte monitoring devices, insertion of the microneedle array and its sensors may be less invasive and involve less pain for the user. Additional advantages of other aspects of the analyte monitoring devices and methods are further described below.

FIG. 3A-FIG. 3D depict aspects of the analyte monitoring device 110. FIG. 3A-FIG. 3D depict an upper perspective view, a side view, a bottom view, and an exploded view, respectively, of the analyte monitoring device 110.

The analyte monitoring device 110 may include a housing that at least partially surrounds or encloses other components (e.g., electronic components) of the analyte monitoring device 110, such as for protection of such components. For example, the housing may be configured to help prevent dust and moisture from entering the analyte monitoring device 110. In some variations, an adhesive layer may attach the housing to a surface (e.g., skin) of a user, while permitting the microneedle array 140 to extend outwardly from the housing and into the skin of the user. Furthermore, in some variations, the housing may generally include rounded edges or corners and/or be low-profile to reduce interference with clothing, etc. worn by the user.

For example, as shown in FIGS. 3A-3D, an example variation of the analyte monitoring device 110 may include a housing cover 320 and a base plate 330, configured to at least partially surround internal components of the analyte monitoring device 110. For example, the housing cover 320 and the base plate 330 may provide an enclosure for a sensor assembly 350 including the microneedle array 140 and electronic components. Once assembled, the microneedle array 140 extends outwardly from a portion of the base plate 330 in a skin-facing direction (e.g., an underside) of the analyte monitoring device 110.

The housing cover 320 and the base plate 330 may, for example, include one or more rigid or semi-rigid protective shell components that may couple together via suitable fasteners (e.g., mechanical fasteners), mechanically interlocking or mating features, and/or an engineering fit. The housing cover 320 and the base plate 330 may include radiused edges and corners and/or other atraumatic features. When coupled together, the housing cover 320 and the base plate 330 may form an internal volume that houses internal components, such as the sensor assembly 350. For example, the internal components arranged in the internal volume may be arranged in a compact, low-profile stack-up as the sensor assembly 350.

The analyte monitoring device 110 may include one or more adhesive layers to attach the analyte monitoring device 110 (e.g., the coupled together housing cover 320 and the base plate 330) to a surface (e.g., the skin) of a user. As shown in FIG. 3D, the one or more adhesive layers may include an inner adhesive layer 342 and an outer adhesive layer 344. The inner adhesive layer 342 may adhere to the base plate 330, and the outer adhesive layer 344 may adhere to the inner adhesive layer 342 and, on its outward facing side, provide an adhesive for adhering (e.g., temporarily) to the skin of the user. The inner adhesive layer 342 and the outer adhesive layer 344 together act as a double-sided adhesive for adhering the analyte monitoring device 110 to the skin of the user. The outer adhesive layer 344 may be protected by a release liner that the user removes to expose the adhesive prior to skin application. In some variations, a single adhesive layer is provided. In some variations, the outer adhesive layer 344 and/or the inner adhesive layer 342 may have a perimeter that extends farther than the perimeter or periphery of the housing cover 320 and the base plate 330. This may increase surface area for attachment and increase stability of retention or attachment to the skin of the user. The inner adhesive layer 342 and the outer adhesive layer 344 each have an opening that permits passage of the outwardly extending microneedle array 140, as further described below. The openings of the inner adhesive layer 342 and the outer adhesive layer 344 may generally align with one another but may, in some variations, differ in size such that one opening is smaller than the other opening. In some variations, the openings are substantially the same size.

The base plate 330 has a first surface (e.g., outwardly exposed surface) opposite a second surface and serves as a support and/or connection structure and as a protective cover for the sensor assembly 350. The base plate 330 is sized and shaped to attach to the housing cover 320. The base plate 330 may be shaped to securely fit within the housing cover 320 such that outer edges of the base plate 330 align with corresponding edges of an opening of the housing 320. The alignment may be such that there is no gap between the outer edges of the base plate 330 and the corresponding edges of the opening of the housing cover 320.

A connection member 332 may be formed in a central or near central region of the first surface of the base plate 330. The connection member 332 has a first surface substantially parallel to the first surface of the base plate 330. Sidewalls extend from edges of the first surface of the connection member 332 to the first surface of the base plate 330. A remaining portion of the first surface of the base plate 330 surrounding the connection member 332 may be flat or substantially flat. One or more connector features may extend outwardly from the sidewalls of the connection member 332 to releasably engage with corresponding connectors of a microneedle enclosure. The first surface and the sidewalls of the connection member 332 define, in part, a cavity. The cavity may be further defined through a portion of the base plate 330 adjacent (e.g., below) the connection member 332. The cavity has an opening, and is accessible, on the second surface of the base plate 330. An aperture 334 is formed through the first surface of the connection member 332. The aperture 334 may be sized and shaped such that the microneedle array 140 fits securely within and extends through the aperture 334. For example, sidewalls of the microneedle array 140 may align with corresponding sidewalls of the aperture 334. In some variations, the aperture 334 may be sized and shaped to correspond with an area surrounding the microneedle array 140. The openings in the inner adhesive layer 342 and the outer adhesive layer 344 are sized such that the connection member 332 extends through the openings without interfering with the inner adhesive layer 342 and the outer adhesive layer 344. For example, the diameter of the opening of the inner adhesive layer 342 and the diameter of the opening of the outer adhesive layer 344 is larger than that of the connection member 332.

Although the housing cover 320 and the base plate 330 depicted in FIGS. 3A-3D are substantially circular with the housing cover 320 having a dome shape, in other variations, the housing cover 320 and the base plate 330 may have any suitable shape. For example, in other variations the housing cover 320 and the base plate 330 may be generally prismatic and have an elliptical, triangular, rectangular, pentagonal, hexagonal, or other suitable shape. The outer adhesive layer 344 may extend outwardly from the housing cover 320 and the base plate 330 to extend beyond the perimeter of the housing cover 320. The outer adhesive layer 344 may be circular, as shown in FIGS. 3A-3D or may have an elliptical, triangular, rectangular, pentagonal, hexagonal, or other suitable shape and need not be the same shape as the housing cover 320 and/or the base plate 330.

In some variations, the analyte monitoring device 110 may provide user status, analyte monitoring device status, and/or other suitable information directly via a user interface (e.g., display, indicator lights, etc. as described below) on the analyte monitoring device 110. Thus, in contrast to analyte monitoring devices that may solely communicate information to a separate peripheral device (e.g., mobile phone, etc.) that in turn communicates the information to a user, in some variations such information may be directly provided by the analyte monitoring device 110.

Accordingly, in some variations, the housing cover 320 may include a user interface, such as an interface to provide information in a visual, audible, and/or tactile manner to provide information regarding user status and/or status of the analyte monitoring device, and/or other suitable information. Examples of user status that may be communicated via the user interface include information representative of analyte measurement in the user (e.g., below a predetermined target analyte measurement threshold or range, within a predetermined target analyte measurement range, above a predetermined target analyte measurement threshold or range, increase or decrease of analyte measurement over time, rate of change of analyte measurement, other information relating to trend of analyte measurements, other suitable alerts associated with analyte measurement, etc.). Examples of analyte monitoring device status that may be communicated via the user interface include device operation mode (e.g., associated with device warm-up state, analyte monitoring state, battery power status such as low battery, etc.), a device error state (e.g., operational error, pressure-induced sensing attenuation, fault, failure mode, etc.), device power status, device life status (e.g., anticipated sensor end-of-life), status of connectivity between device and a mobile computing device, and/or the like.

In some variations, the user interface may by default be in an enabled or "on" state to communicate such information at least whenever the analyte monitoring device 110 is performing analyte measurements or whenever the analyte monitoring device 110 is powered on, thereby helping to ensure that information is continuously available to the user. For example, user interface elements may communicate through a display or indicator light(s) (e.g., as described below) not only alerts to flag user attention or recommend remedial action, but also when user status and/or device status are normal. Accordingly, in some variations, a user is not required to perform an action to initiate a scan to learn their current analyte measurement level(s), and such information may always readily be available to the user. In some variations, however, a user may perform an action to disable the user interface temporarily (e.g., similar to a "snooze" button) such as for a predetermined amount of time (e.g., 30 minutes, 1 hour, 2 hours, etc.) after which the user interface is automatically reenabled, or until a second action is performed to reenable the user interface.

In some variations, the user interface of the housing cover 320 may include a display configured to visually communicate information. The display may, for example, include a display screen (e.g., LCD screen, OLED display, electrophoretic display, electrochromic display, etc.) configured to display alphanumeric text (e.g., numbers, letters, etc.), symbols, and/or suitable graphics to communicate information to the user. For example, the display screen may include a numerical information, textual information, and/or a graphics (e.g., sloped line, arrows, etc.) of information such as user status and/or status of the analyte monitoring device. For example, the display screen may include text or graphical representations of analyte measurement levels, trends, and/or recommendations (e.g., physical activity, reduced dietary intake, etc.).

Indicator light(s) on the display may be illuminated in one or more various manners to communicate different kinds of information. For example, an indicator light may be selectively illuminated on or off to communicate information (e.g., illumination "on" indicates one status, while illumination "off" indicates another status). An indicator light may be illuminated in a selected color or intensity to communicate information (e.g., illumination in a first color or intensity indicates a first status, while illumination in a second color or intensity indicates a second status). An indicator light may be illuminated in a selected temporal pattern to communicate information (e.g., illumination in a first temporal pattern indicates a first status, while illumination in a second temporal pattern indicates a second status). For example, an indicator light may be selectively illuminated in one of a plurality of predetermined temporal patterns that differ in illumination frequency (e.g., repeated illumination at a rapid or slow frequency), regularity (e.g., periodic repeated illumination vs. intermittent illumination), duration of illumination "on" time, duration of illumination "off" time, rate of change in illumination intensity, duty cycle (e.g., ratio of illumination "on" time to illumination "off" time), and/or the like, where each predetermined temporal pattern may indicate a respective status.

In some variations, a display may include multiple indicator lights that may be collectively illuminated in one or more predetermined illumination modes or sequences in accordance with one or more predetermined spatial and/or temporal patterns. For example, in some variations, some or all the indicator lights arranged on a display may be illuminated in synchrony or in sequence to indicate a particular status. Accordingly, the selected subset of indicator lights (e.g., the spatial arrangement of the indicator lights that are illuminated) and/or the manner in which they are illuminated (e.g., illumination order, illumination rate, etc.) may indicate a particular status. In some variations, a plurality of indicator lights may illuminate simultaneously or in sequence to increase the diversity of the color palette. For example, in some variations, red, green, and blue LEDs may be illuminated in rapid succession to create the impression of white light to a user.

In some variations, one or more of the above-described illumination modes may be combined in any suitable manner (e.g., combination of varying color, intensity, brightness, luminosity, contrast, timing, location, etc.) to communicate information.

FIGS. 4A-4E depict aspects of the sensor assembly 350 of the analyte monitoring device 110 in a perspective exploded view, a side exploded view, a distal perspective view, a side view, and a proximal perspective view, respectively.

The sensor assembly 350 includes microneedle array components and electronic components to implement analyte detection and processing aspects of the microneedle array-based continuous analyte monitoring device 110 for the detection and measuring of an analyte. In some variations, the sensor assembly 350 is a compact, low-profile stack-up that is at least partially contained within the internal volume defined by the housing cover 320 and the base plate 330.

In some variations, the sensor assembly 350 includes a microneedle array assembly 360 and an electronics assembly 370 that connect to one another to implement the microneedle array analyte detection and processing aspects further described herein. In some variations, the electronics assembly 370 includes a first printed circuit board (PCB) 450 on which electronic components are connected, and the microneedle array assembly 360 includes a second printed circuit board (PCB) 420 on which the microneedle array 140 is connected.

In some variations, the microneedle array assembly 360 includes, in addition to the second PCB 420 and the microneedle array 140, an epoxy skirt 410 and a second PCB connector 430. The microneedle array 140 is coupled to a top side (e.g., outer facing or distal side) of the second PCB 420 so that the individual microneedles of the microneedle array 140 are exposed as described with reference to FIG. 3A-FIG. 3D. The second PCB connector 430 is coupled to a back or proximal side, opposite the top side, of the second PCB 420. The second PCB connector 430 may be an electromechanical connector and may communicatively couple to the first PCB 450 through a first PCB connector 470 on a top side (e.g., outer facing or distal side) of the first PCB 450 to allow for signal communication between the second PCB 420 and the first PCB 450. For example, signals from the microneedle array 140 may be communicated to the first PCB 450 through the second PCB 420, the second PCB connector 430, and the first PCB connector 470.

The second PCB 420 may in part determine the distance to which the microneedle array 140 protrudes from the back plate 330 of the housing. Accordingly, the height of the second PCB 420 may be selected to help ensure that the microneedle array 140 is inserted properly into a user's skin. During microneedle insertion, the first surface (e.g., outer facing surface) of the connection member 332 of the back plate 330 may act as a stop for microneedle insertion. If the second PCB 420 has a reduced height and its top surface is flush or nearly flush with the first surface of the connection member 332, then the connection member 332 may prevent the microneedle array 140 from being fully inserted into the skin.

In some variations, other components (e.g., electronic components such as sensors or other components) may also be connected to the second PCB 420. For example, the second PCB 420 may be sized and shaped to accommodate electronic components on the top side or the back side of the second PCB 420.

Figure 3A:
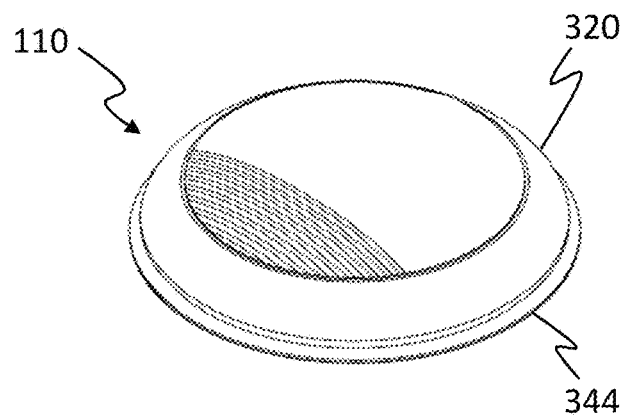
FIGS. 3A-3D depict an upper perspective view, a side view, a bottom view, and an exploded view, respectively, of an analyte monitoring device.
Figure 3B:
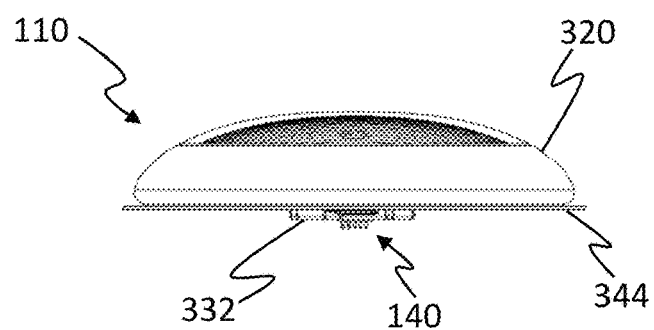
Figure 3C:
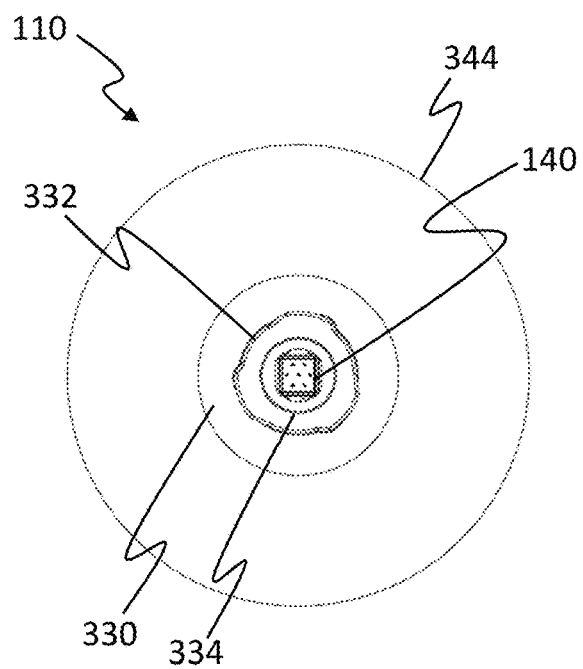
Figure 3D:
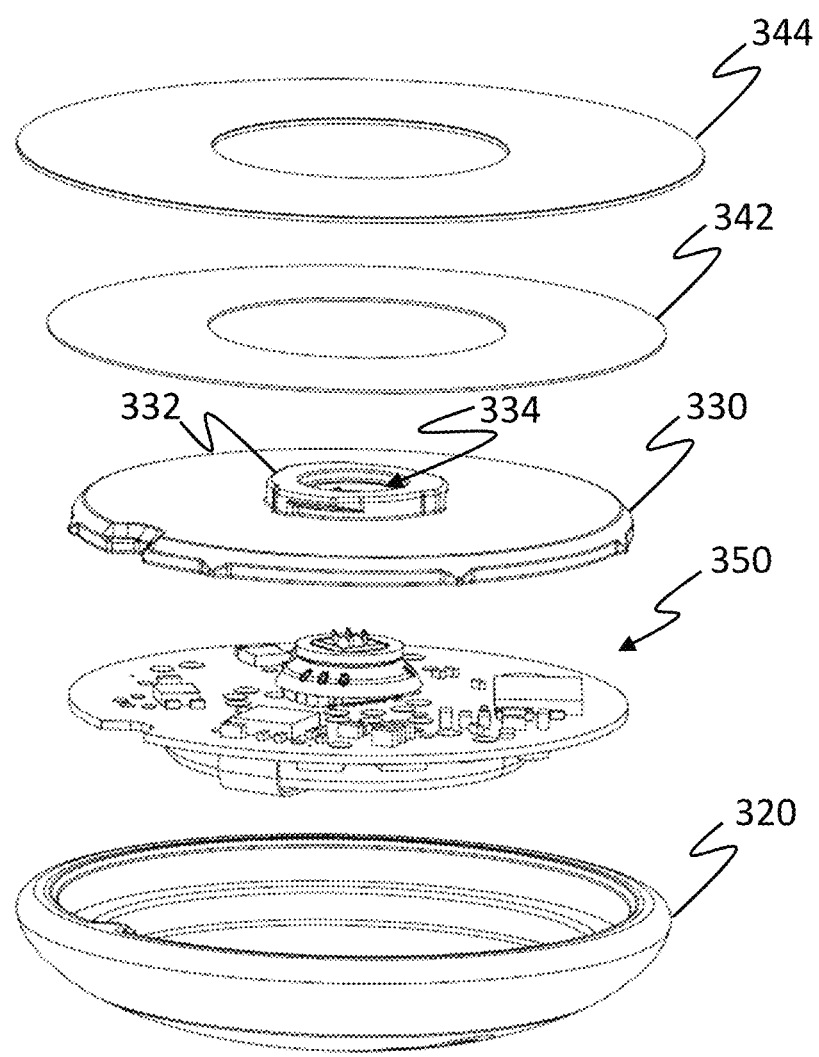

In some variations, the epoxy skirt 410 may be deposited along the edges (e.g., the outer perimeter) of the microneedle array 140 to provide a secure fit of the microneedle array 140 within the aperture 334 formed in the connection member 332 of the base plate 330 and/or to relieve the sharp edges along the microneedle array 140, as shown in FIG. 3B and FIG. 3C. For example, the epoxy skirt 410 may occupy portions of the aperture 334 not filled by the microneedle array 140 and/or portions of the cavity defined in the base plate 330 not filled by the second PCB 420. The epoxy skirt 410 may also provide a transition from the edges of the microneedle array 140 to the edge of the second PCB 420. In some variations, the epoxy skirt 410 may be replaced or supplemented by a gasket (e.g., a rubber gasket) or the like.

The electronics assembly 370, having the first PCB 450, includes a battery 460 coupled to a back side of the first PCB 450, opposite the top side on which the first PCB connector 470 is coupled. In some variations, the battery 460 may be coupled on the top side of the first PCB 450 and/or in other arrangements. Additional details of the electronics assembly 370 are described with reference to FIG. 5.

Figure 4A:
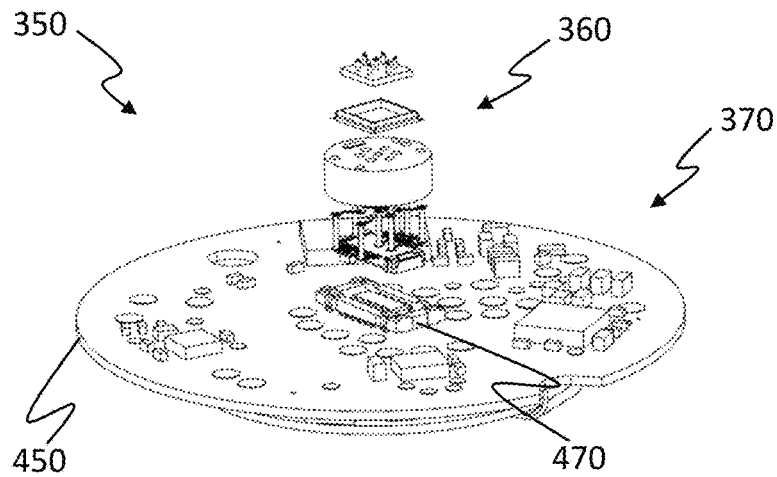
FIGS. 4A-4E depict a perspective exploded view, a side exploded view, a lower perspective view, a side view, and an upper perspective view, respectively, of a sensor assembly in an analyte monitoring device.
Figure 4B:
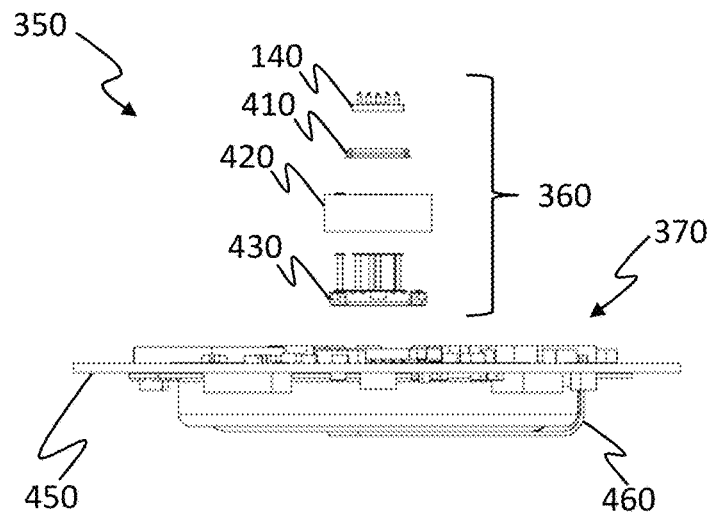
Figure 4C:
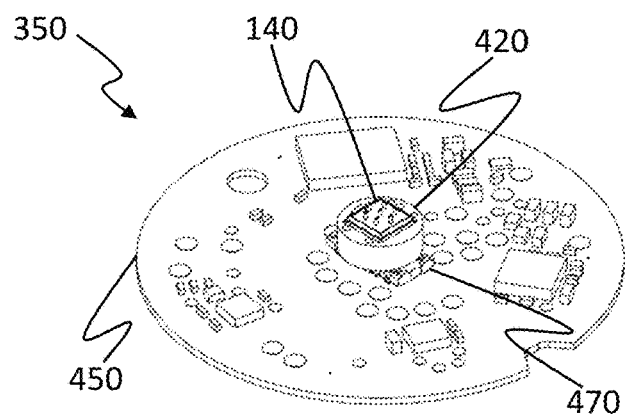
Figure 4D:
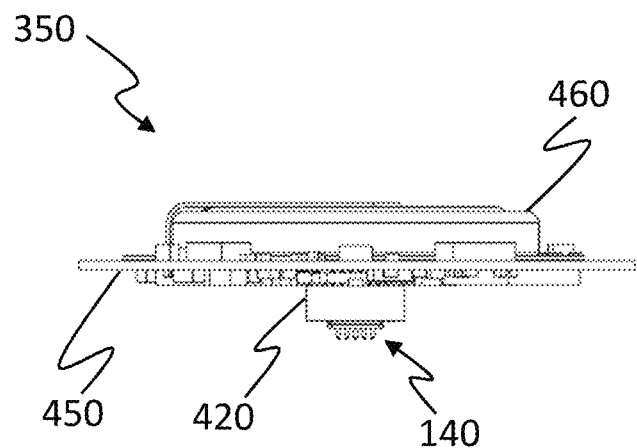
Figure 4E:
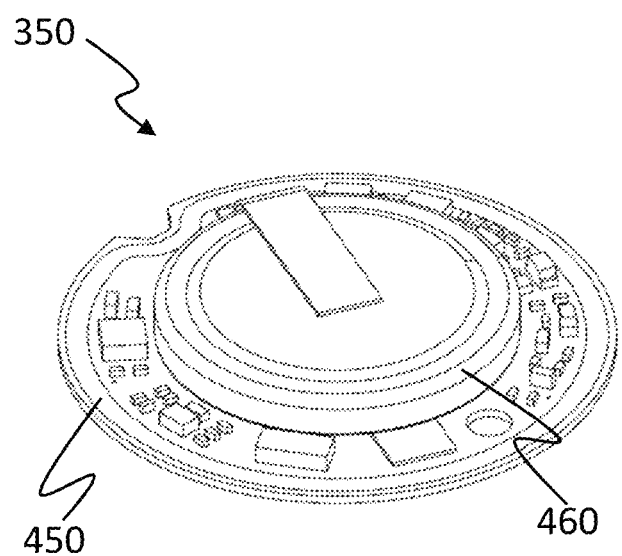
Figure 4F:
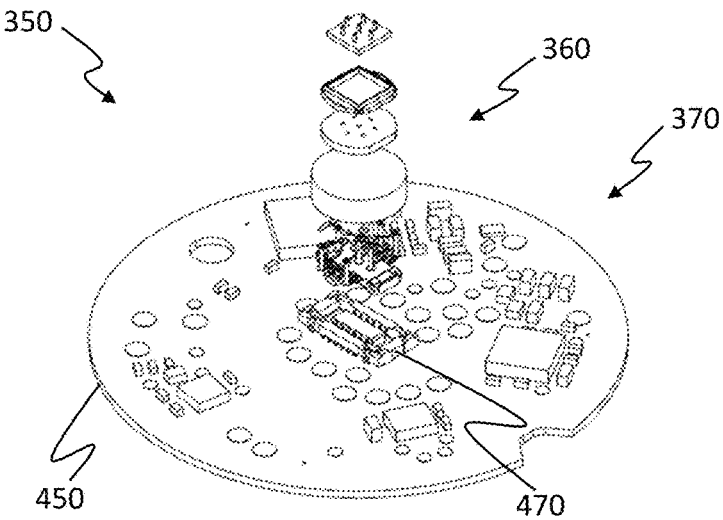
FIGS. 4F-4H depict a perspective exploded view, a side exploded view, and a side view, respectively, of a sensor assembly in an analyte monitoring device.
Figure 4G:
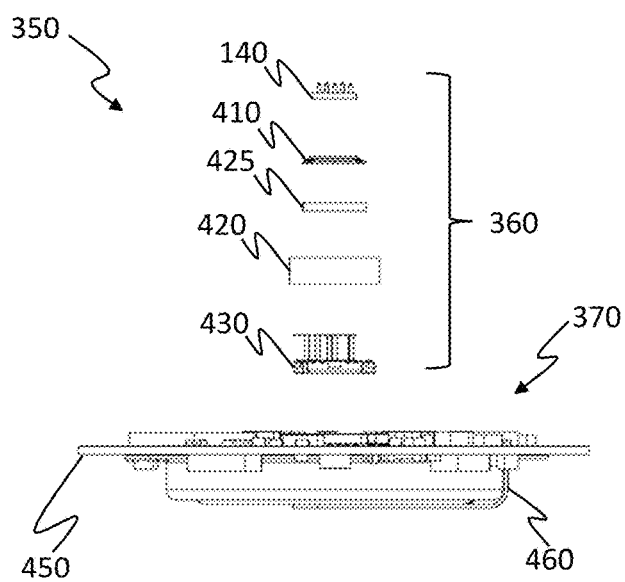
Figure 4H:
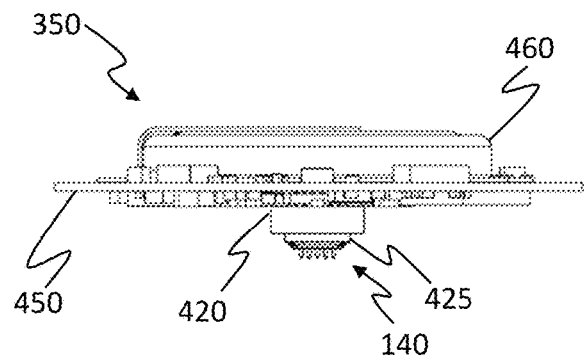

FIGS. 4F-4H depict aspects of an alternate variation of the sensor assembly 350 of the analyte monitoring device 110. A perspective exploded view, a side exploded view, and a side view of the sensor assembly 350 are provided, respectively, in FIGS. 4F-4H.

As shown, in the sensor assembly 350, an additional PCB component, an intermediate PCB 425, is incorporated. In some variations, the intermediate PCB 425 is part of the microneedle array assembly 360 and is positioned between and connected to the second PCB 420 and the microneedle array 140. The intermediate PCB 425 may be added to increase the height of the microneedle array assembly 360 such that the microneedle array 140 extends at a further distance from the base plate 330, which may aid in insertion of the microneedle array 140 into the skin of a user. The microneedle array 140 is coupled to a top side (e.g., outer facing side) of the intermediate PCB 425 so that the individual microneedles of the microneedle array 140 are exposed as described with reference to FIG. 3A-FIG. 3D. The second PCB 420 is coupled to a back side, opposite the top side, of the intermediate PCB 425, and the second PCB connector 430 is coupled to a back side, opposite the top side, of the second PCB 420. The epoxy skirt 410 (which may be replaced or supplemented by a gasket of the like) provides a transition from the edges of the microneedle array 140 to the edge of the intermediate PCB 425.

The intermediate PCB 425 with the second PCB 420 in part determine the distance to which the microneedle array 140 protrudes through the aperture 334 of the back plate 330. The incorporation of the intermediate PCB 425 provides an additional height to help ensure that the microneedle array 140 is properly inserted into a user's skin. In some variations, the top side (e.g., outer facing side) of the intermediate PCB 425 extends through and out of the aperture 334 so that the first surface (e.g., top, exposed surface) of the connection member 332 surrounding the aperture 334 does not prevent the microneedle array from being fully inserted into the skin. In some variations, the top side (e.g., outer facing side) of the intermediate PCB 425 does not extend out of the aperture 334 but the increased height (by virtue of incorporating the intermediate PCB 425) ensures that the microneedle array 140 protrudes at a sufficient distance from the back plate 330 of the housing.

Figure 5:
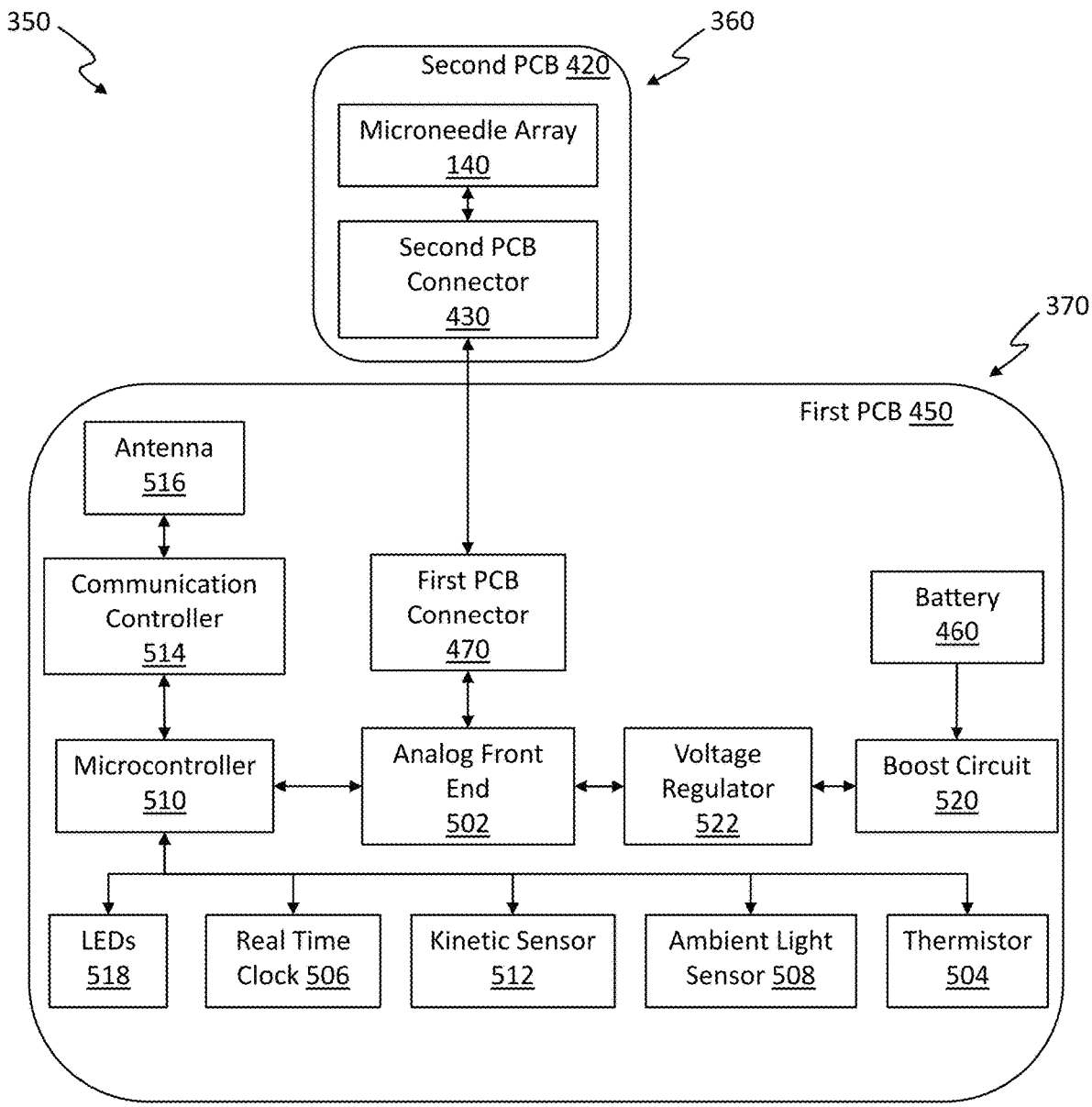
FIG. 5 depicts a system block diagram of a sensor assembly in an analyte monitoring device.

FIG. 5 depicts a block diagram representation of the sensor assembly 350 of the analyte monitoring device 110. The sensor assembly 350 includes aspects of the microneedle array assembly 360 and the electronics assembly 370, which may include aspects of the electronics system 120 shown in and described with reference to FIG. 2A.

The sensor assembly 350 includes the first PCB 450 for the electronics assembly 370 and the second PCB 420 (and optionally the intermediate PCB 425) for the microneedle array assembly 360. The first PCB 450 and the second PCB 420 may be connected, thereby establishing a connection between the microneedle array assembly 360 and the electronics assembly 370, by way of connectors. For example, the second PCB connector 430 on the back side of the second PCB 420 connects to the first PCB connector 470 on the top side of the first PCB 450.

The second PCB connector 430 and the first PCB connector 470 may be electromechanical connectors that provide for communicative coupling between the second PCB 420 and the first PCB 450 to allow for signal communication between the second PCB 420 and the first PCB 450. For example, signals from the microneedle array 140 may be communicated to the first PCB 450 through the second PCB 420, the second PCB connector 430, and the first PCB connector 470.

The first PCB 450 may include various electronic components to receive and process the electrochemical signals received from the microneedle array 140, and some electronic components may be included for additional functionality. As shown in FIG. 5, the first PCB 450 may include coupled thereto an analog front end 502, a thermistor 504, a real time clock 506, an ambient light sensor 508, a microcontroller 510 (or a controller), a kinetic sensor 512, a communication controller 514, an antenna 516, the battery 460, a voltage regulator 522, and a boost circuit 520. In some variations, the second PCB 420 or the intermediate PCB 425 may include, in addition to the microneedle array 140 and the second PCB connector 430, the thermistor 504. In some variations, the thermistor 504 is positioned to minimize its distance to the skin of a user. In some variations, the thermistor 504 is not included and temperature measurements may be obtained from a temperature sensor that is incorporated in the analog front end 502. In some variations, fewer, additional, and/or alternative components may be included in the sensor assembly 350, as described further herein.

The analog front end 502 is part of the sensor assembly 350 (e.g., part of the electronics assembly 370) of the analyte monitoring device 110. The analog front end 502 may include sensor circuitry (e.g., sensor circuitry 124 as shown in FIG. 2A) that converts analog current measurements to digital values that can be processed by the microcontroller 510. The analog front end 502 may, for example, include a programmable analog front end that is suitable for use with electrochemical sensors. In some variations, the analog front end 502 may be an ultra-low power programmable analog front end for use with electrochemical sensors. In some variations, the analog front end 502 may be a high precision, impedance, and electrochemical front end. In some variations, the analog front end 502 may be a configurable analog front end potentiostat for low-power chemical sensing applications. The analog front end 502 may provide biasing and a complete measurement path, including the analog to digital converters (ADCs). Ultra-low power may allow for the continuous biasing of the microneedle array 140 to maintain accuracy and fast response.

In some variations, the analog front end 502 may be compatible with both two and three terminal electrochemical sensors, such as to enable both DC current measurement, AC current measurement, and electrochemical impedance spectroscopy (EIS) measurement capabilities. Furthermore, the analog front end 502 may include an internal temperature sensor and programmable voltage reference, support external temperature monitoring, provide an external reference source, and integrate voltage monitoring of bias and supply voltages for safety and compliance.

In some variations, the analog front end 502 may include a multi-channel potentiostat to multiplex sensor inputs and handle multiple signal channels. For example, the analog front end may include a multi-channel potentiostat such as that described in U.S. Pat. No. 9,933,387, which is incorporated herein in its entirety by this reference.

In some variations, the analog front end 502 and peripheral electronics may be integrated into an application-specific integrated circuit (ASIC). In some variations, this integrated solution may include the microcontroller 510 described below.

In some variations, the sensor assembly 350 of the analyte monitoring device 110 may include at least one microcontroller 510 (e.g., the controller 122 shown in FIG. 2A) incorporated in the electronics assembly 370. The microcontroller 510 may include, for example, a processor with integrated flash memory. In some variations, the microcontroller 510 in the analyte monitoring device 110 may be configured to perform analysis to correlate sensor signals to an analyte measurement (e.g., glucose measurement). For example, the microcontroller 510 may execute a programmed routine in firmware to interpret the digital signal (e.g., from the analog front end 502), perform any relevant algorithms and/or other analysis, and route processed data to and/or from a communication module (e.g., the communication module 126 shown in FIG. 2A). Keeping the analysis on-board the analyte monitoring device 110 may, for example, enable the analyte monitoring device 110 to broadcast analyte measurement(s) to multiple devices (e.g., mobile computing devices such as a smartphone or smartwatch, therapeutic delivery systems such as insulin pens or pumps, etc.) in parallel, while ensuring that each connected device has the same information.

In some variations, the microcontroller 510 may be configured to activate and/or inactivate the analyte monitoring device 110 in response to one or more detected conditions or states of one or more of the environment (e.g., surrounding area of the analyte monitoring device 110) or components of the analyte monitoring device 110. For example, the microcontroller 510 may be configured to power on the analyte monitoring device 110 in response to one or more conditions, such as insertion of the microneedle array 140 into skin, removal of the analyte monitoring device 110 from an applicator device, transition of the analyte monitoring device 110 from an unusable state to a usable state, and a command from an external device, as further described herein. The microcontroller 510 may be configured to power on the analyte monitoring device 110 in response to a determination of a valid power-on event. Based on the type of valid power-on event, the microcontroller 510 may transition the analyte monitoring device 110 to a corresponding mode of operation. In some variations, the microcontroller 510 may be configured to determine a source of a power-on event and transition the analyte monitoring device 110 to a mode of operation corresponding to the source of the power-on event. Additional details related to power-on are further described below.

In some variations, the microcontroller 510 may utilize an 8-bit, 16-bit, 32-bit, or 64-bit data structure. Suitable microcontroller architectures include Reduced Instruction Set Computer (RISC) architectures or Complex Instruction Set Computer (CISC) architectures, and flash memory may be embedded or external to the microcontroller 510 for suitable data storage. In some variations, the microcontroller 510 may be a single core microcontroller, while in some variations the microcontroller 510 may be a multi-core (e.g., dual core) microcontroller which may enable flexible architectures for optimizing power and/or performance within the analyte monitoring device 110. For example, the cores in the microcontroller 510 may include similar or differing architectures. For example, in an example variation, the microcontroller 510 may be a dual core microcontroller including a first core with a high performance and high-power architecture, and a second core with a low performance and low power architecture. The first core may function as a "workhorse" in that it may be used to process higher performance functions (e.g., sensor measurements, algorithmic calculations, etc.), while the second core may be used to perform lower performance functions (e.g., background routines, data transmission, etc.). Accordingly, the different cores of the microcontroller 510 may be run at different duty cycles (e.g., the second core for lower performance functions may be run at a higher duty cycles) optimized for their respective functions, thereby improving overall power efficiency. In some variations, the microcontroller 510 may include embedded analog circuitry, such as for interfacing with additional sensors and/or the microneedle array 140. In some variations, the microcontroller 510 may be configured to operate using a 0.8V to 5V power source, such as a 1.2V to 3V power source.

In some variations, the sensor assembly 350 of the analyte monitoring device 110 may include at least one communication module (e.g., communication module 126 as shown in FIG. 2A), such as a wireless communication module to communicate with one or more devices. For example, the communication module may include a wireless transceiver that is integrated into the microcontroller 510. However, the electronics assembly 370 may additionally or alternatively include a communication module that is separate from the microcontroller 510. In some variations, the communication module may communicate via wireless network (e.g., through Bluetooth, NFC, WiFi, RFID, Thread, 6LoWPAN, LoRa, or any type of data transmission that is not connected by cables). For example, devices may directly communicate with each other in pairwise connection (1:1 relationship, e.g., unicasting) or in a hub-spoke or broadcasting connection ("one to many" or 1:m relationship, e.g., multicasting). As another example, the devices may communicate with each other through mesh networking connections (e.g., "many to many", or m:m relationships, or ad-hoc), such as through Bluetooth mesh networking. Wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), or any other suitable communication protocol. Some wireless network deployments may combine networks from multiple cellular networks or use a mix of cellular, Wi-Fi, and satellite communication. In an example variation, the communication module may include a wireless transceiver integrated into the microcontroller and including a Bluetooth Low Energy compatible radio that complies with the Bluetooth Special Interest Group 5.0 specification.

The communication module may further include or be coupled to one or more antennas (e.g., antenna 128 as shown in FIG. 2A). For example, the sensor assembly 350 may include a chip antenna mounted on the first PCB 450 or an antenna implemented directly onto the first PCB 450, which may provide better range while reducing cost and complexity. In some variations, as shown in FIG. 5, a communication controller 514 may be part of the sensor assembly 350 on the first PCB 450 and may be coupled to an antenna 516 for wireless communication according to various wireless protocols as described above. In a variation, the communication controller 514 is an NFC tag IC or NFC module. In some variations, rather than occupy space on the first PCB 450, the antenna may be contained in or etched on the housing, such as on an underside area or topside area of the housing cover 320. For example, a portion of the housing cover 320 may be metallicized and metal may be deposited to form the antenna, with contacts between the metal and the first PCB 450 incorporated. In other variations, a flexible PCB may be incorporated for the antenna and fitted, for example, within the housing cover 320, and contacts between the flexible PCB and the main PCB may be incorporated. By incorporating the antenna into a space separate from the first PCB 450, additional space is made available on the first PCB 450 and increased performance may be achieved by optimizing the placement of the antenna (e.g., at a point closest to or on the housing cover 320).

In some variations, remote devices can come in and out of range from the communication controller 514 (or other communication module) to connect and reconnect so that the user is able to seamlessly connect and transfer information between devices (e.g., between the analyte monitoring device 110 and one or more remote devices). In some variations, the microcontroller 510 on the analyte monitoring device 110 may have a unique serial number, enabling tracking of the analyte monitoring device 110 during production and/or field use.

As described above, in some variations, the analyte monitoring device 110 may include one or more sensors in addition to the microneedle array 140. For example, the analyte monitoring device 110 may include one or more temperature sensors configured to measure skin temperature, which may be used to enable temperature compensation for the microneedle array 140. For example, in some variations, a thermistor 504 (or other temperature sensor such as a resistance temperature detector, a semiconductor junction, a bimetallic sensor, and a thermopile sensor) may be coupled to the first PCB 450 or the second PCB 420. The thermistor 504 may be arranged near a skin-facing portion or outer facing side of the sensor assembly, such as on the second PCB 420 or on the top side of the first PCB 450 (e.g., near or adjacent to the back plate 330). The back plate 330 may be of a suitable thickness to reduce thermal resistance and improve heat transfer and measurement accuracy.

A sensor may be incorporated in the sensor assembly 350 to enable dynamic adjustment of light levels in indicator lights, such as light emitting diodes (LEDs) 518, to compensate for environmental light conditions and to help conserve power. The ambient light sensor 508 may, in some variations, be coupled to the first PCB 450 to sense the level of ambient light in the surrounding environment of the analyte monitoring device 110. Additional details related to utilization of the ambient light sensor 508 are provided below.

The LEDs 518 may be coupled to the first PCB 450 of the sensor assembly 350 as part of the electronics assembly 370. The LEDs 518 may be controlled in one or more predetermined illumination patterns or modes to communicate different statuses and/or other suitable information. An indicator light may be controlled to illuminate with multiple colors (e.g., red, orange, yellow, green, blue, and/or purple, etc.) or in only one color. For example, an indicator light may include a multi-colored LED. As another example, an indicator light may include a transparent or semi-transparent material (e.g., acrylic) positioned over one or more different-colored light sources (e.g., LED) such that different-colored light sources may be selectively activated to illuminate the indicator light in a selected color. The activation of light sources can either occur simultaneously or in sequence. An indicator light may have any suitable form (e.g., raised, flush, recessed, etc. from housing body) and/or shape (e.g., circle or other polygon, ring, elongated strip, etc.). In some variations, an indicator light may have a pinhole size and/or shape to present the same intensity of the light as a larger light source, but with significantly less power requirements, which may help conserve onboard power in the analyte monitoring device 110.

Although LEDs are shown in FIG. 5, in some variations, other types of indicator lights may be incorporated in the sensor assembly 350. For example, the indicator lights may include LEDs, OLEDs, lasers, electroluminescent material, or other suitable light sources or waveguides. In some variations, rather than include LEDs or indicator lights, the dome surface may be a liquid crystal display (LCD) or an E-ink display.

In some variations, additional sensors may be incorporated in the sensor assembly 350. For example, a kinetic sensor 512 (e.g., as described in further detail below) may be incorporated in the electronics assembly 370 and coupled to the first PCB 450. The kinetic sensor 512 may be used to further determine appropriate periods for the analyte monitoring device 110 to transition to a power saving mode or a reduced power state. For example, detection of darkness via the ambient light sensor 508 and no motion of the analyte monitoring device 110 via the kinetic sensor 512 may indicate that the wearer of the analyte monitoring device 110 is asleep or in a relaxed state, which may trigger the analyte monitoring device 110 to transition to a power saving mode or a reduced power state. In some variations, the kinetic sensor 512 may be used to track movement of the user of the analyte monitoring device 110 for other purposes. The kinetic sensor 512 may, for example, include an accelerometer, a gyroscope, and/or an inertial measurement unit to capture positional, displacement, trajectory, velocity, acceleration, and/or device orientation values. For example, such measurements may be used to infer the wearer's physical activity (e.g., steps, intense exercise) over a finite duration. In some variations, the kinetic sensor 512 may be employed to enable detection of wearer interactions with the analyte monitoring device 110, such as touch or tapping. For example, touch or tap detection can be employed to silence or snooze notifications, alerts, and alarms, control a wirelessly connected mobile computing device, or to activate and/or deactivate a user interface on the analyte monitoring device 110 (e.g., an embedded display or indicator light such as the LEDs 518). Touching or tapping may be performed in a defined sequence and/or for a predetermined duration (e.g., at least 3 seconds, at least 5 seconds) to elicit certain actions (e.g., display or indicator light deactivation and/or activation). In some variations, the analyte monitoring device 110 may transition to a power saving mode upon detection of limited motion or activity (e.g., absence of significant acceleration) for at least a predetermined period of time (e.g., 15 minutes, 30 minutes, 45 minutes, 1 hour, or other suitable of time), as measured by the kinetic sensor 512 and/or other sensors.

In some variations, the analyte monitoring device 110 may include at least one real-time clock (RTC) 506. For example, the real-time clock 506 may be part of the electronics assembly 370 coupled to the first PCB 450. In some variations, the real-time clock 506 has an embedded quartz crystal or the like for maintaining an accurate tracking of time. The real-time clock 506 may be employed to track absolute time (e.g., Coordinated Universal Time, UTC, or local time) when the analyte monitoring device 110 is in storage or during use. In some variations, synchronization to absolute time may be performed following manufacturing of the analyte monitoring device 110. During operation, the real-time clock 506 may output a clocking signal to the microcontroller 510 to drive and/or adjust internal clocks of the microcontroller 510 to ensure that the microcontroller 510, which may have lower timing accuracy than the real-time clock 506, is properly tracking time. In some variations, the clocking signal from the real-time clock 506 to the microcontroller 510 is a constant signal. In some variations, the clocking signal is sent periodically at predefined intervals.

The real-time clock 506 may be employed to time-stamp analyte measurements (e.g., glucose measurements) during operation of the analyte monitoring device 110 to create a time-series data set that is communicated to a connected peripheral device (e.g., mobile computing device), cloud storage, or other suitable data storage device, such as for later review by the user (e.g., wearer of the analyte monitoring device), a support network, a healthcare provider, etc. In some variations, the microcontroller 510 performs the time-stamping operations.

As shown in FIG. 2A, the analyte monitoring device may include one or more power sources 130 configured to provide power to other components. For example, the analyte monitoring device 110 may include a battery 460. The battery 460 may be any suitable type of battery able to provide power to the various components of the sensor assembly 350. The battery 460 may be a silver-oxide battery, which has a high energy density and is more environmentally friendly than lithium batteries. In some variations, a primary (e.g., non-rechargeable) battery may be used. Furthermore, in some variations, a secondary (e.g., rechargeable) battery may be used. However, any suitable power source may be used, including a lithium-based battery.

In some variations, as further described below, the battery 460 may be coupled to a boost circuit 520. The boost circuit 520 may be part of the electronics assembly 370 coupled to the first PCB 450. The boost circuit 520 may be incorporated to provide appropriate power levels to certain electronic components. For example, the boost circuit 520 may boost or increase the voltage provided by the battery 460 to provide sufficient power to one or more of the components of the sensor assembly 350, as further described herein. In some variations, a voltage regulator 522 may be coupled to an output of the boost circuit 520 to reduce the noise generated by the boost circuit 520.

In some variations, the analyte monitoring device 110 may be paired to at least one peripheral device such that the peripheral device receives broadcasted or otherwise transmitted data from the analyte monitoring device 110, including measurement data. Suitable peripheral devices include, for example a mobile computing device (e.g., smartphone, smartwatch) which may be executing a mobile application.

As described above, the pairing may be accomplished through suitable wireless communication modules (e.g., NFC and/or Bluetooth). In some variations, the pairing may occur after the analyte monitoring device 110 is applied and inserted into the skin of a user (e.g., after the analyte monitoring device 110 is activated). The pairing may occur prior to the analyte monitoring device 110 being applied and inserted into the skin of a user.

Thus, the paired mobile or other device may receive the broadcasted or transmitted data from the analyte monitoring device 110. The peripheral device 110 may display, store, and/or transmit the measurement data to the user and/or a healthcare provider and/or a support network. Furthermore, in some variations, the paired mobile or wearable device may perform algorithmic treatment to the data to improve the signal fidelity, accuracy, and/or calibration, etc. In some variations, measurement data and/or other user information may additionally or alternatively be communicated and/or stored via a network (e.g., a cloud network).

By way of illustration, in some variations, a mobile computing device or other computing device (e.g., smartphones, smartwatches, tablets, etc.) may be configured to execute a mobile application that provides an interface to display estimated glucose values, trend information, and historical data, etc. Although the below description refers specifically to glucose as a target analyte, the features and processes described below with respect to glucose may be similarly applied to applications relating to other kinds of analytes.

In some variations, the mobile application may use the mobile computing device's wireless communication framework to scan for the analyte monitoring device 110. The analyte monitoring device 110 may power on or initialize once it is applied to the skin, and the analyte monitoring device 110 may begin an advertising process. The mobile application may then connect to the analyte monitoring device 110 and begin priming the microneedle array 140 for measurement. In case the mobile application detects multiple analyte monitoring devices, the mobile application may detect the analyte monitoring device 110 that is closest in proximity to itself, may request the user (e.g., via the user interface on the mobile device) to confirm disambiguation, and/or may request a confirmation via a physical interaction with the analyte monitoring device 110 that is intended for use (e.g., tapping or other prescribed action with the analyte monitoring device 110 by the user). In some variations, the mobile application may also be capable of connecting to multiple analyte monitoring devices simultaneously. This may be useful, for example, to replace sensors that are reaching the end of their lifetime.

In some variations, the Bluetooth® Low Energy™ (BLE) protocol may be used for connectivity. For example, the sensor implements a custom BLE peripheral profile for the analyte monitoring system. Data may be exchanged after establishing a standard secure BLE connection between the analyte monitoring device and the smartphone, smartwatch, or tablet running the mobile application. The BLE connection may be maintained permanently for the life of the sensor. If the connection is broken due to any reasons (e.g., weak signal) the analyte monitoring device may start advertising itself again and the mobile application may re-establish the connection at the earliest opportunity (e.g., when in range/physical proximity).

In some variations, there may be one or more additional layers of security implemented on top of the BLE connection to ensure authorized access consisting of a combination of one or more techniques such as passcode-protection, shared-secrets, encryption, and multi-factor authentication.

The mobile application may guide the user through initiating a new analyte monitoring device. Once this process completes, the mobile application is not be required for the analyte monitoring device 110 to operate and record measurements. In some variations, a smart insulin delivery device that is connected to the analyte monitoring device 110 can be authorized from the mobile application to receive glucose readings from the sensor directly. In some variations, a secondary display device like a smartwatch can be authorized from the mobile application to receive glucose readings from the sensor directly.

Furthermore, in some variations the mobile application may additionally or alternatively help calibrate the analyte monitoring device 110. For example, the analyte monitoring device 110 may indicate a request for calibration to the mobile application, and the mobile application may request calibration input from the user to calibrate the sensor.

Figure 6:
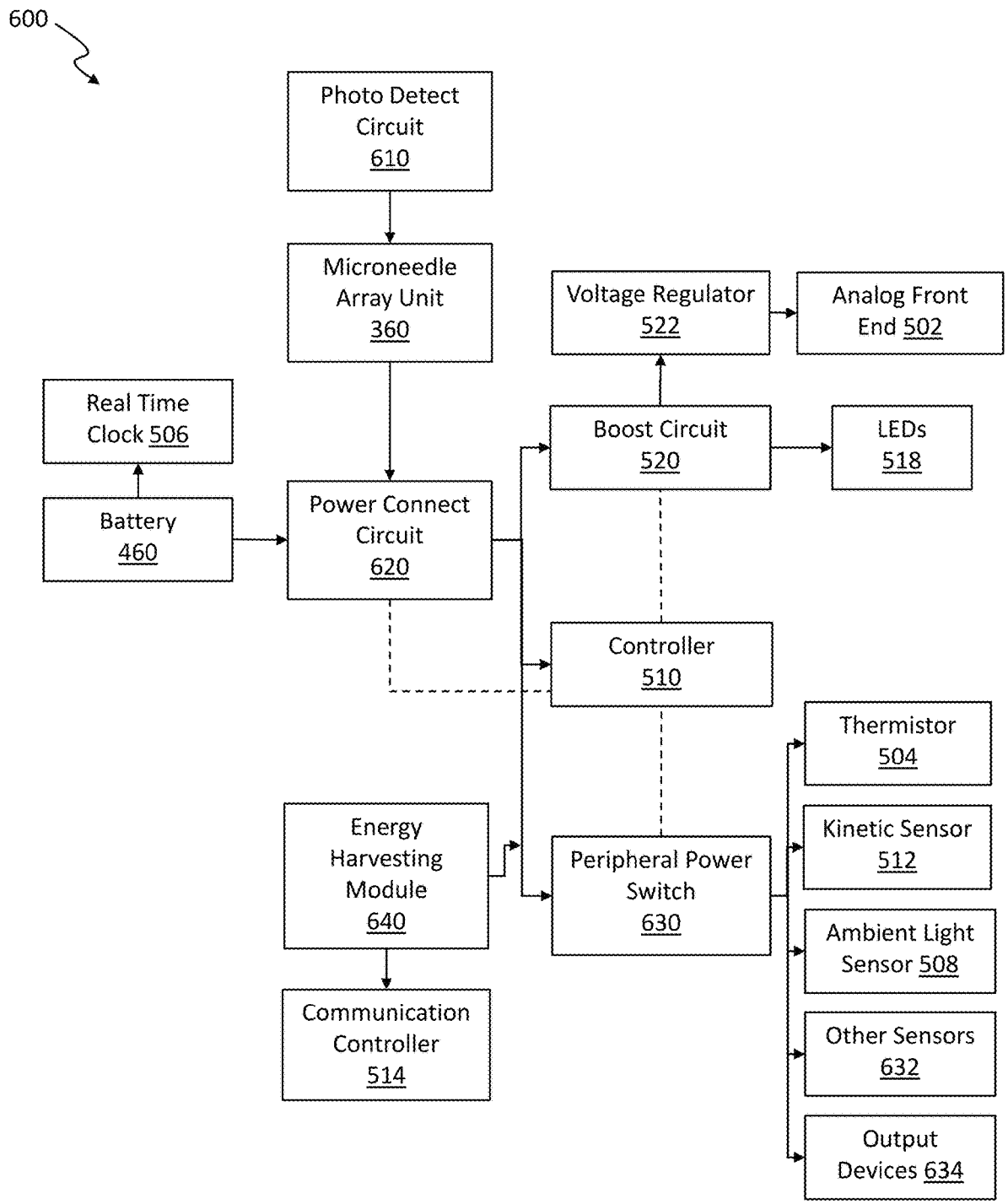
FIG. 6 depicts a system block diagram of a power architecture of a sensor assembly in an analyte monitoring device.

FIG. 6 depicts a system block diagram of a power architecture 600 of the sensor assembly 350 of the analyte monitoring device 110 according to some implementations. The power architecture 600 defines how power may be distributed through the sensor assembly 350. The power architecture 600 executes power management processes to aid in providing multiple days of use of the analyte monitoring device 110. For example, in some variations utilizing the power architecture 600 that implements power management aspects described herein, the analyte monitoring device 110 may continuously operate (e.g., the battery 460 lasts) for up to 10 days. In some variations, the analyte monitoring device 110 may continuously operate for up to five, six, seven, eight, or nine days. In some variations, depending on the power source and the components of the sensor assembly 350, the analyte monitoring device 110 may continuously operate for more than 10 days.

As shown in FIG. 6, the battery 460 provides power to the real time clock 506 and to a power connect circuit 620, which may in some variations be coupled to the first PCB 450. The power connect circuit 620 connects the battery 460 to additional electronic components of the sensor assembly 350, allowing for the battery 460 to power the additional electronic components. For example, the power connect circuit 620 includes a switch that connects the battery 460 to the boost circuit 520, the microcontroller 510, and a peripheral power switch 630. In other variations, the power connect circuit 620 may connect the battery 460 to fewer, additional, or alternative components. By incorporating the power connect circuit 620 in the power architecture 600 of the sensor assembly 350, power from the battery 460 to additional components is controlled. For example, the power connect circuit 620 may maintain an open position (e.g., the switch is open, thus connection between the battery 460 and the boost circuit 520, the microcontroller 510, and the peripheral power switch 630 is not established) until occurrence of a triggering event. The triggering event signals the power connect circuit 620 to establish the connection between the battery 460 and the additional electronic components, thereby ensuring that the battery 460 does not unnecessarily drain. The triggering event may be, for example, an event that is indicative of beginning use of the analyte monitoring device 110 for active detection and measuring of an analyte.

In some variations, the triggering event may be detection of light. For example, the analyte monitoring device 110 may be maintained in a dark or darkened environment until the user is ready to apply and use the analyte monitoring device 110. When the analyte monitoring device 110 is removed from the dark or the darkened environment, light may be detected by virtue of the removal of the analyte monitoring device 110 from the dark or the darkened environment. For example, the analyte monitoring device 110 may be contained, for storage, in a container that provides the dark or the darkened environment. The container may be a packaging unit or an applicator device, for example. Once the analyte monitoring device 110 is removed from the container (e.g., dispensed from the packaging unit or applied to the user by the applicator device) or the container is at least partially opened, light from the new environment (e.g., the triggering event) may be detected. In some variations, a seal, a sticker, a protective cover, or the like may be applied to one or more portions of the analyte monitoring device 110. Removal of the seal, the sticker, or the protective cover exposes the analyte monitoring device 110 to light, resulting in the triggering event.

The power connect circuit 620 may receive (e.g., from another component) a signal or an instruction indicative of the triggering event. As described, the triggering event may be detection of light (e.g., environmental light surrounding the sensor assembly 350). For example, in some variations, a photo detect circuit 610 is incorporated to detect environmental light. The photo detect circuit 610 may be a photo transistor that responds to light. When light is incident on the photo transistor, the photo transistor is triggered and sends a signal to the power connect circuit 620. Thus, in response to detection of light (e.g., the triggering event), the photo detect circuit 610 signals the power connect circuit 620, which responds by closing the switch, resulting in connection being established between the battery 460 and the boost circuit 520, the microcontroller 510, and the peripheral power switch 630. The battery 460, at this point, begins discharging and providing power to the boost circuit 520, the microcontroller 510, and the peripheral power switch 630. As described, in some variations, the power connect circuit 620 may provide a connection between the battery 460 and fewer, additional, or alternative electronic components.

In some variations, the photo detect circuit 610 is not connected until the microneedle array assembly 360 is connected to the electronics assembly 370. For example, the photo detect circuit 610 may be coupled to the first PCB 450 and may have a signal line piped through the second PCB 420. When the first PCB 450 and the second PCB 420 are not connected (e.g., the microneedle array assembly 360 is not connected to the electronics assembly 370), the photo detect circuit 610 is disabled due to the signal line that is piped through the second PCB 420 being open, resulting in the circuitry of the electronics assembly 370 being disconnected. In this disconnected state, the power connect circuit 620 is not connected to the photo detect circuit 610, and the switch of the power connect circuit 620 remains opened. When the first PCB 450 and the second PCB 420 are connected, the signal piped through the second PCB 420 from the photo detect circuit 610 is completed, enabling the photo detect circuit 610. In this connected state, the photo detect circuit 610 is connected to the power connect circuit 620, and the power connect circuit 620 may respond to a signal or an instruction from the photo detect circuit 610.

The microneedle array assembly 360 thus causes the photo detect circuit 610 to be connected to the power connect circuit 620 of the electronics assembly 370. This ensures that the battery 460 cannot be depleted (e.g., by being discharged through the power connect circuit 620 to the electronic components connected to the power connect circuit 620) until the second PCB 420 is connected via the second PCB connector 430 to the first PCB 450 via the first PCB connector 470. In some variations, this eliminates or reduces possible battery depletion during certain stages of manufacturing (e.g., until the microneedle array assembly 360 is connected to the electronics assembly 370).

The power connect circuit 620 may further include a latch circuit that functions to maintain the connection (e.g., keep the switch closed) between the battery 460 and the boost circuit 520, the microcontroller 510, and the peripheral power switch 630 after the switch in the power connect circuit 620 is moved to the closed position. The latch circuit ensures that the photo detect circuit 610 will not interfere with the power connect circuit 620 after the triggering event. In some variations, the power connect circuit 620 may include an ideal diode to control one way charge and prevent back powering of the battery 460.

By incorporating the power connect circuit 620 in the power architecture 600 of the sensor assembly 350, power from the battery 460 to additional components is controlled. For example, the power connect circuit 620 may maintain an open position (e.g., the switch is open, thus connection between the battery 460 and the boost circuit 520, the microcontroller 510, and the peripheral power switch 630 is not established) until occurrence of a triggering event. The triggering event signals the power connect circuit 620 to establish the connection between the battery 460 and the additional electronic components, thereby ensuring that the battery 460 does not unnecessarily drain. The triggering event may be, for example, an event that is indicative of beginning use of the analyte monitoring device 110 for active detection and measuring of an analyte.

As shown in FIG. 6 and described above, the microcontroller 510 is powered by the battery 460 through the power connect circuit 620. The microcontroller 510 is tied to the boost circuit 520 and to the peripheral power switch 630 through respective enable pins. In response to the microcontroller 510 booting or initiating a booting sequence, a main power latch in the microcontroller 510 is asserted. The microcontroller 510 may remove and/or apply power to peripheral units through the peripheral power switch 630, as further described herein. The microcontroller 510 may remove and/or apply power to the boost circuit 520. In some variations, for example, the microcontroller 510 may remove and/or apply power to the LEDs 518.

As shown in FIG. 6, the boost circuit 520 powers the LEDs 518 and the analog front end 502. In some variations, the LEDs 518 and the analog front end 502 require a stable voltage throughout operation that exceeds the voltage of the battery 460. In some variations, the voltage of the battery 460 drops over time as its capacity is used. For example, the battery 460 may be a 3V battery but may drop to a lower level as capacity is used. The voltage required by the LEDs 518 and/or the analog front end 502 may exceed the maximum voltage of the battery 460, or the voltage required by the LEDs 518 and/or the analog front end may exceed a voltage value of the battery 460 as its capacity is used. The boost circuit 520 is, in some variations, incorporated to provide the stable voltage required by the LEDs 518 and the analog front end 502. In some variations, the boost circuit 520 boosts the voltage to other or additional components of the sensor assembly 350. In some variations, and as shown in FIG. 6, the voltage regulator 522 is connected between the boost circuit 520 and the analog front end 502 to reduce the noise generated by the boost circuit 520 and provide a more stable signal to the analog front end 502.

In some variations, the LEDs 518 may require a stable, higher voltage than the voltage of the battery 460, and the boost circuit 520 operates to boost the battery voltage to a level required by the LEDs 518. In some variations, by applying a higher voltage than required to the LEDs 518, the LEDs 518 may output an illumination having consistent brightness throughout use of the analyte monitoring device 110. As described herein, the battery voltage may drift downward during the lifetime of the battery 460 as the battery 460 is being discharged. In some variations, the voltage required by the analog front end 502 may be higher than the voltage of the battery 460 as battery voltage drifts downward. To compensate for this difference, the boost circuit 520 operates to boost the battery voltage to a level required by the analog front end 502. In some variations, the boost circuit 520 provides the same voltage to the LEDs 518 and to the analog front end 502. In other variations, a different, customized voltage is provided to the LEDs 518 and to the analog front end 502.

As shown in FIG. 6 and described above, the peripheral power switch 630 is powered by the battery 460 through the power connect circuit 620. The peripheral power switch 630, upon connection to the battery 460 through the power connect circuit 620, supplies power to various peripheral devices. For example, the peripheral power switch 630 supplies power to the kinetic sensor 512, the ambient light sensor 508, the thermistor 504, other sensors 632, and output devices 634 (e.g., a linear resonant actuator (LRA) and/or an eccentric rotating mass (ERM) for output of haptics, a speaker). In some variations, the peripheral power switch 630 may disable the communication controller 514.

In some variations, the microcontroller 510 may determine that the life of the battery 460 is nearing its end. For example, the microcontroller 510 may determine that the voltage level of the battery 460 is low and/or may determine that an expected end of life is approaching. An end-of-life determination may be made through a measurement of the voltage of the battery 460 under load. Over time, as the capacity of the battery 460 is reduced, the voltage decreases, which may be used as an indicator of the life of the battery 460. In some variations, in response to a determination that the voltage level of the battery 460 is low and/or that an expected end of life is approaching, the microcontroller 510 may enter a reduced power state. In the reduced power state, the microcontroller 510 may cut power to one or more electronic components. In some variations, the microcontroller 510 may cut power to one or more electronic components that are not involved in the analyte detection and measuring (e.g., the kinetic sensor 512, the ambient light sensor 508, the other sensors 632, the output devices 634, the LEDs 518). In some variations, in the reduced power state, the microcontroller 510 may adjust usage of one or more electronic components. For example, the microcontroller may adjust the brightness of the LEDs 518 and/or the illumination sequence of the LEDs 518 such that the LEDs 518 emit less light and/or are illuminated for shorter periods of time or less frequently, thereby conserving power. For example, in the reduced power state, the brightness of the LEDs 518 may be adjusted such that the LEDs 518 are about 50% dimmer than during normal operation. In some variations, other levels of brightness (e.g., between about 20% and about 80% of normal operation brightness) may be used. The illumination sequence of the LEDs 518 may be adjusted such that the LEDs 518 are illuminated less frequently than during normal operation. For example, in the reduced power state, the time between illumination of the LEDs 518 may be increased by about one to about ten times that of normal operation.

The power architecture 600 of the sensor assembly 350 of the analyte monitoring device 110, as shown in FIG. 6, may also include an energy harvesting module 640. Power from the energy harvesting module 640 may be used to download data when the battery 460 has reached end of life or before the battery 460 is connected to the microcontroller 510. In some variations, data (e.g., sensor data and/or operation data related to operation of the analyte monitoring device 110) is stored on the microcontroller 510 (e.g., memory of the microcontroller 510) and may be sent to the communication controller 514. For example, the data may be sent in chunks over a link (e.g., an NFC link) between the microcontroller 510 and the communication controller 514. Using the energy harvesting module 640, the data may then be downloaded to an external device (e.g., a user's device, a remote server) using, for example, an NFC reader. This solution ensures that data (e.g., sensor data and/or operation data related to operation of the analyte monitoring device 110) is not lost upon the battery 460 being depleted. In some alternate variations, the energy harvesting module 640 may be used as a backup, alternate, or temporary power supply in lieu of the battery 460 (e.g., if the battery 460 is depleted or before connection of the battery 460). The energy harvesting module 640 may provide power to the boost circuit 520, the microcontroller 510, and the peripheral power switch 630 to continue operation of the analyte monitoring device 110. In some variations, the energy harvesting module 640 may power all the components of the sensor assembly 350. In some variations, the real time clock 506 is not powered. In some variations in which a secondary battery is incorporated, the energy harvesting module 640 may be used to recharge the primary battery (e.g., the battery 460), during which time the secondary battery may be used. When the battery 460 is recharged, the energy harvesting module 640 may be used to recharge the secondary battery.

Figure 7:
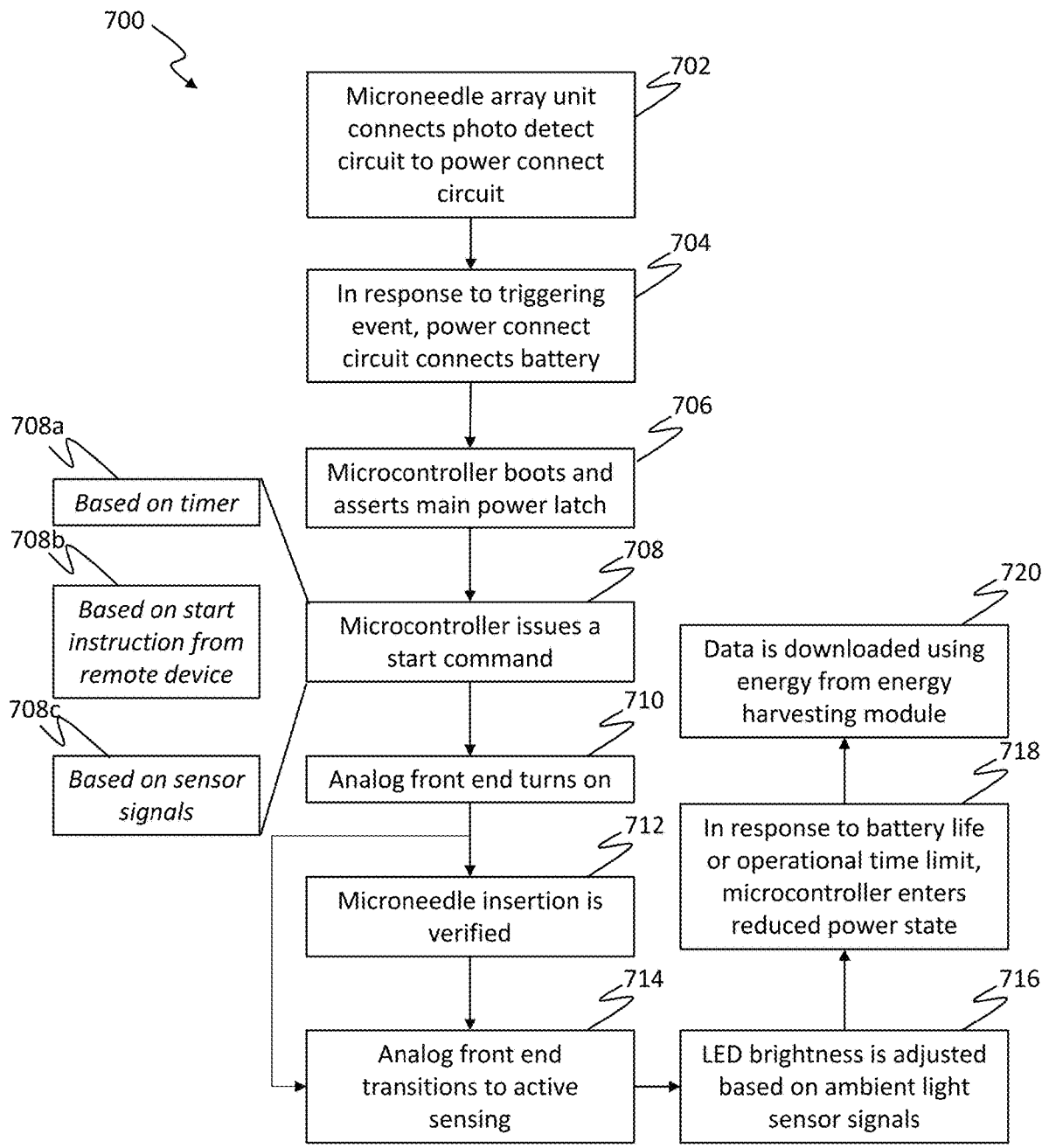
FIG. 7 depicts a flow chart of a power-up process of a sensor assembly in an analyte monitoring device.

FIG. 7 depicts an exemplary process flow chart 700 implemented by the power architecture 600 of the sensor assembly 350 of the analyte monitoring device 110.

At 702, the microneedle array assembly 360 connects the photo detect circuit 610 to the power connect circuit 620. For example, in some variations, the photo detect circuit 610 is not connected to the electronics assembly 370 until the microneedle array assembly 360 is connected to the electronics assembly 370. This ensures that the battery 460 cannot be unnecessarily or inadvertently depleted during, for example, certain stages of manufacturing (e.g., until the microneedle array assembly 360 is connected to the electronics assembly 370 through connection of the respective connectors, the second PCB connector 430 and the first PCB connector 470).

At 704, in response to a triggering event, the power connect circuit 620 establishes a connection between the battery 460 and one or more electronic components of the sensor assembly 350. In some variations, the one or more electronic components may include the boost circuit 520, the microcontroller 510, and/or the peripheral power switch 630. The triggering event may be detection of light by the photo detect circuit 610. Upon detection of light, the photo detect circuit 610 may send a signal to the power connect circuit 620, instructing the power connect circuit 620 to close its switch to connect the battery 460 to the rest of the sensor assembly 350.

At 706, the microcontroller 510 initiates a boot sequence and asserts the main power latch. For example, when the battery 460 and the microcontroller 510 are connected (e.g., the battery 460 is supplying power to the microcontroller 510), the microcontroller 510 may implement a boot sequence and/or assert a main power latch so that the microcontroller 510 can begin operating.

At 708, the microcontroller 510 issues a start command. For example, the microcontroller 510 may issue a start command to the boost circuit 520 and the peripheral power switch 630. As indicated by 708a, 708b, and 708c, one or more factors may contribute to the issuance of the start command. In some variations and as indicated at 708a, once the microcontroller 510 is turned on (e.g., at 706), the microcontroller 510 may start a timer using the real-time clock 506. Once a predetermined period has elapsed, the microcontroller 510 may issue the start command. The predetermined period may be used as a safety to ensure that sufficient time has passed once the triggering event has occurred. In some variations and as indicated at 708b, the issuance of the start command may be based on a start instruction from a remote device (e.g., transmitted over a communication link). In some variations and as indicated at 708c, the issuance of the start command may be based on one or more sensor signals. For example, signals from the kinetic sensor 512 and/or the ambient light sensor 508 may be used to determine if the microcontroller 510 should issue the start command.

At 710, in response to the start command from the microcontroller 510, the analog front end 502 may be turned on.

At 712, a microneedle insertion verification process may be implemented. For example, the analog front end 502 may apply a bias potential between one or more electrodes to determine if the microneedles of the microneedle array 140 are inserted to a sufficient depth in the skin of the user. The bias may be applied between a working electrode and a reference electrode/counter electrode. The resulting current or resistance between the electrodes may be compared to a threshold value that may indicate a range of values that are indicative of insertion. If the resulting current or resistance falls within the range, this serves as an indication that the microneedle array 140 is inserted to a sufficient depth. If the resulting current is not within the range, it may be determined that the microneedle array 140 is not at a sufficient depth for sensing of the analyte. Additional details related to microneedle insertion verification are provided with reference to FIG. 9A-FIG. 9B. In some variations, the microneedle insertion verification process at 712 is not implemented.

At 714, the analog front end 502 transitions to active sensing. The transition to active sensing may be in response to verification of the microneedle insertion at 712. If at 712 the verification process indicates that the microneedles are not properly inserted, the process may end. If, however, the verification process indicates that the microneedles of the microneedle array 140 are properly inserted, the transition to active sensing occurs, including the application of a bias potential higher than that applied during the verification of microneedle insertion. The bias potential is applied between a working electrode and a reference electrode of the analyte monitoring device 110, as further described herein.

At 716, the brightness of the LEDs 518 is controlled based on ambient light. In some variations, in the active sensing mode, the light conditions in and/or around the environment of the analyte monitoring device 110 are monitored to control the brightness of the LEDs. For example, signals from the ambient light sensor 508 are monitored and correlated to one of a plurality of brightness levels. The brightness levels may define the brightness of the LEDs (e.g., brightest, dimmer, dimmest, off). Additional details related to the ambient light sensor are provided below.

At 718, in response to a determination of battery life of the battery 460 nearing its end or based on an operational time limit, the microcontroller 510 may enter a reduced power state. For example, the microcontroller 510 may determine that the voltage level of the battery 460 is low and/or may determine that an expected end of life of the battery 460 is approaching and may accordingly enter a reduced power state to accommodate the battery 460. In some variations, the microcontroller 510 may determine that the operational time limit, which be a predefined and stored value, is met. The reduced power state may be entered to further extend the life of the battery 460. In the reduced power state, the microcontroller 510 may cut power to one or more electronic components such as those that are not involved in the analyte detection and measuring (e.g., the kinetic sensor 512, the ambient light sensor 508, the other sensors 632, the output devices 634, the LEDs 518). In some variations, in the reduced power state, the microcontroller 510 may adjust usage of one or more electronic components.

At 720, in some variations, data from the communication controller 514 is downloaded from the analyte monitoring device 110. When the battery 460 is depleted, the energy harvesting module 640 may be used to extract and/or download data such as the analyte measurements and operational data related to operation of the analyte monitoring device 110.

In some variations, it may be desirable to power-on the microcontroller 510 for updates, such as firmware updates. Further, it may be desirable to do so when the analyte monitoring device 110 is contained in packaging or an applicator device and is not yet ready for use. In such a situation (e.g., where an update is desirable and the analyte monitoring device 110 is not yet ready for use, and moreover there is an unknown period of time until when the analyte monitoring device 110 will be ready for use), if the battery 460 is connected to the microcontroller 510, the battery 460 will be at least partially depleted when the analyte monitoring device 110 is applied to a user and should begin the sensing operations it is intended for. Implementations of the current subject matter incorporate the energy harvesting module 640 to provide power to the microcontroller 510 to allow for the updates to be applied. In the presence of a communication field, the communication field provides energy to the energy harvesting module 640. The energy harvesting module 640 is connected to the microcontroller 510, thus is able to power-on the microcontroller 510 for the update that is provided over the communication field. When the communication field is removed from the analyte monitoring device 110, the microcontroller 510 returns to a shut-down mode until again powered-on by the energy harvesting module 640 or the battery 460.

In some instances, the analyte monitoring device 110 may encounter a spurious communication field (e.g., a communication field that is not intended to provide a firmware update). For example, in manufacturing, transit, or distribution environments, the analyte monitoring device 110 may come into the presence of communication fields. Because of the energy harvesting module 640, the microcontroller 510 may be powered on in unintended circumstances (e.g., when there is no need to power-on the microcontroller 510). Variations provide for the microcontroller 510, in response to being powered on or receiving a power-on signal, to determine if a power-on event that caused the microcontroller 510 to be powered-on is a valid power-on event. In some variations, the microcontroller 510 determines if a valid source caused the power-on event. By determining if the power-on event is a valid power-on event and/or by determining the source of the power-on event, the microcontroller 510 responds to the power-on event by entering a mode that corresponds to the power-on event and/or the power-on source.

A valid power-on event is, in some variations, defined as a transition of the analyte monitoring device 110 to a usable state or an intentional positioning of the analyte monitoring device 110 in a communication field. In particular, if the analyte monitoring device 110 is transitioned to a usable state, the determination or confirmation of this transition allows the microcontroller 110 to respond accordingly by transitioning the analyte monitoring device 110 to a start-up sequence. If the analyte monitoring device 110 is intentionally positioned in a communication field, the determination or confirmation of this intentional positioning allows the microcontroller 110 to respond by performing an update based on a received communication and transitioning to a powered-off mode once the update is completed. If the power-on event is invalid and/or the source is not a valid source, the microcontroller 110 responds accordingly by transitioning to a powered-off mode.

In some variations, in response to being powered on, the microcontroller 510 determines if the power-on event is a valid power-on event by determining if the analyte monitoring device 110 is transitioned to a usable state. The usable state may be a state in which the battery is connected to the microcontroller 510. The usable state may be a state in which the analyte monitoring device 110 is ready to be applied to the user, is removed from an applicator device, or is applied to the user. In some variations, the usable state may be a pre-insertion environment in which the analyte monitoring device 110 is ready for application or a post-insertion environment in which the analyte monitoring device 110 is inserted into the skin surface of the user.

The microcontroller 510 may determine if the analyte monitoring device 110 is in a usable state based on data from one or more sources and/or sensors of the analyte monitoring device 110. For example, one or more sensors and associated data from the one or more sensors may be used to determine a change in the environment of the analyte monitoring device 110. In one implementation, light data from the ambient light sensor 508 may be used. For example, the analyte monitoring device 110 may be maintained in a darkened environment until the user is ready to apply and use the analyte monitoring device 110. When the analyte monitoring device 110 is removed from the darkened environment or when the darkened environment is altered and is exposed to at least some light, such as when a cap, packaging, or a protective covering is removed, light is detected, and this light may serve as an indication that the user has transitioned the analyte monitoring device 110 to a usable state. The microcontroller 510, in the event of being powered-on, may query the ambient light sensor 508, receive a light data measurement, and compare the light data measurement to a light threshold value determined to be indicative of the analyte monitoring device 110 transitioned to a usable state (e.g., removed from the darkened environment or the darkened environment altered sufficiently to indicate the user is preparing to apply the analyte monitoring device 110). If the light data measurement meets or exceeds the light threshold value, the microcontroller 510 may begin a start-up sequence. The start-up sequence may include the microcontroller 510 entering an idle mode, remaining in the idle mode for a predetermined period of time, and entering an operational mode. The predetermined period of time may be a time sufficient to ensure that the analyte monitoring device 110 has been applied to the user. In some variations, the start-up sequence may include transitioning the microcontroller 510 directly to the operational mode. In this variation in which light is used to determine the transition to the usable state, the transition, resulting from the removal from the darkened environment or the change to the darkened environment, causes the photo detect circuit 610 to generate a signal to the power connect circuit 620 to close the switch thereby establishing a connection between the battery 460 and the microcontroller 510.

In an alternative variation, magnetic field data may be used to indicate if the analyte monitoring device 110 is in a usable state. In a variation, a magnet is secured or positioned in an applicator device or packaging of the analyte monitoring device 110, which includes a magnetic switch, such as a digital magnetic switch (e.g., a tunneling magnetoresistance (TMR) switch). The magnet and the magnetic switch are arranged and positioned such that when the analyte monitoring device 110 is contained in the applicator device or the packaging, the magnet and the magnetic switch are aligned. When the analyte monitoring device 110 is removed from the applicator device or the packaging (e.g., transitioned to a usable state), the magnetic switch, no longer in the presence of a magnetic field due to the removal of the analyte monitoring device 110 from the applicator device or the packaging, sends an input signal (e.g., a power-on signal) to the microcontroller 510. The microcontroller 510 uses the signal from the magnetic switch to confirm a valid power-on event and begins a start-up sequence. The start-up sequence may include the microcontroller 510 entering an idle mode followed by entering an operational mode after a predetermined period of time or in response to verifying that the power-on signal came from the magnetic switch. In some variations, the start-up sequence may include transitioning the microcontroller 510 directly to the operational mode without an idle mode.

In a variation, a multi-axis magnetic switch may be incorporated in the analyte monitoring device 110, and the applicator device or the packaging may include a plurality of (e.g., at least two) magnets aligned with the multi-axis magnetic switch of the analyte monitoring device 110. The plurality of magnets are oriented such that each magnet produces a magnetic field in a direction distinct from the other magnetic fields. This implementation requires that magnetic fields in multiple directions need to be removed before the magnetic switch is triggered.

In another variation, accelerometer data from the kinetic sensor 512 may be used to indicate if the analyte monitoring device 110 is in a usable state. An acceleration threshold value, determined to be indicative of the analyte monitoring device 110 being deployed from an applicator device, may be stored and is used to determine if the analyte monitoring device is transitioned to a usable state (e.g., removed from the applicator device and inserted into the skin surface of the user). The microcontroller 510 may be powered in a low-power state while monitoring data from the kinetic sensor 512. In response to a determination that acceleration data from the kinetic sensor 512 meets or exceeds the acceleration threshold value, the microcontroller 510 uses the signal from the kinetic sensor 512 to confirm a valid power-on event and begins a start-up sequence. The start-up sequence may include the microcontroller 510 entering an idle mode followed by entering an operational mode after a predetermined period of time. In some variations, the start-up sequence may include transitioning the microcontroller 510 directly to the operational mode without an idle mode.

In another variation, capacitance data from a capacitive sensor may be used to indicate if the analyte monitoring device 110 is in a usable state. In a variation, a target is secured or positioned in an applicator device or packaging of the analyte monitoring device 110, which includes a capacitive sensor that generates an electrostatic field. The target and the capacitive sensor are arranged and positioned such that when the analyte monitoring device 110 is contained in the applicator device or the packaging, the target and the capacitive sensor are aligned. When the analyte monitoring device 110 is removed from the applicator device or the packaging (e.g., transitioned to a usable state), the capacitive sensor sends an input signal (e.g., a power-on signal) to the microcontroller 510. In another implementation, when the analyte monitoring device 110 is applied to the user, a capacitive sensor detects skin (which is the target in this implementation). Upon the detection of skin, the capacitive sensor signals the microcontroller.

The microcontroller 510 uses the signal from the capacitive sensor to confirm a valid power-on event and begins a start-up sequence. The start-up sequence may include the microcontroller 510 entering an idle mode followed by entering an operational mode after a predetermined period of time or in response to verifying that the power-on signal came from the capacitive sensor. In some variations, the start-up sequence may include transitioning the microcontroller 510 directly to the operational mode without an idle mode.

More than one source or sensor may provide data to be used in the determination of if a power-on event is a valid power-on event by determining if the analyte monitoring device 110 is transitioned to a usable state. For example, light data, magnetic field data, accelerometer data, and capacitance data may be used in various combinations to determine if the analyte monitoring device 110 is in a usable state. One or more additional sources of data may be used as a check or a confirmation of a first source.

As described above, a valid power-on event may also include an intentional positioning of the analyte monitoring device 110 in a communication field. If the analyte monitoring device 110 is intentionally positioned in a communication field, the determination or confirmation of this intentional positioning allows the microcontroller 110 to respond by performing an update based on a received communication over the communication field.

In a variation, if the analyte monitoring device 110 is not transitioned to the usable state, the microcontroller 510 then determines if the analyte monitoring device 110 is intentionally positioned in the communication field. The intentional positioning of the analyte monitoring device 110 within the communication field is defined as a valid power-on event as it serves as an indication that a remote device is generating a communication field to transmit an update to be applied to the analyte monitoring device 110. The intentional positioning is determined based on a detection of the communication field followed by a receipt within a predetermined period of time of an over-the-air transmission from a remote device. The communication field may be detected by measuring a voltage generated by the energy harvesting module 640. If the energy harvesting module 640 generates a signal (e.g., a voltage level) that is detected by the microcontroller 510, this serves as an indication of a detected communication field. After detecting the communication field, the microcontroller 510 waits a predetermined period of time to receive an over-the-air transmission from the remote device. If the predetermined period of time elapses without the over-the-air transmission, the detected communication field is considered to be unintentional and/or spurious (e.g., not intended for the analyte monitoring device 110). If the over-the air transmission is received within the predetermined period of time, the power-on event is considered to be a valid power-on event, and the analyte monitoring device 110 transitions to a reconfiguration mode.

In the reconfiguration mode, the microcontroller 510 applies reconfiguration parameters included in the over-the-air transmission from the remote device. For example, the remote device may be an NFC-enabled device configured to provide a firmware update to the analyte monitoring device 110. The NFC-enabled device is positioned in close proximity to the analyte monitoring device 110 and transmits the firmware update to be uploaded.

Following completion of the reconfiguration mode, the analyte monitoring device 110 is transitioned to a powered-off mode. The analyte monitoring device 110 will remain in the powered-off mode until a power-on event again occurs, at which point the analyte monitoring device 110 will determine if the power-on event is valid.

If the analyte monitoring device 110 is not transitioned to the usable state and is not intentionally positioned in the communication field (e.g., the power-on event is not a valid power-on event), the analyte monitoring device 110 is transitioned to a powered-off mode. In some variations, the transitioning to a powered-off mode in response to determining that a power-on event is not valid may include enabling a watchdog timer and attempting a shutdown. If the shutdown is successful, the analyte monitoring device 110 is in the powered-off mode. If the shutdown is not successful, the watchdog timer causes a reset to determine the cause of the microcontroller 510 being powered on.

In some variations, in response to being powered on, the microcontroller 510 determines the source of the power-on event and transitions the analyte monitoring device 110 to a mode of operation corresponding to the determined source of the power-on event. The source of the power-on event may be either a connection with the battery 460 or power received from the energy harvesting module 640. When the determined source of the power-on event is the connection with the battery 460, the corresponding mode of operation may be a start-up mode that includes a sequence from an idle mode to an operational mode. The analyte monitoring device 110 may transition from the idle mode to the operational mode after confirmation of an insertion event. The confirmation of the insertion event may be based on one or more of an elapsed time (e.g., waiting a predetermined period of time before moving from the idle mode to the operational mode), accelerometer data that confirms an acceleration threshold value is met (e.g., the analyte monitoring device 110 is applied to the user), an electrical current or resistance resulting from an applied bias potential, and a communication from an external device (e.g., a remote device may issue a command confirming the analyte monitoring device 110 is applied).

In some variations, when the determined source of the power-on event is the power received from the energy harvesting module 640, the corresponding mode of operation may be a reset mode. The reset mode may include receiving an over-the-air transmission, reconfiguring the microcontroller 510 according to reconfiguration parameters contained in the over-the-air transmission, and transitioning to a powered-off mode. The reset mode may include, if the communication field is not present or the over-the-air transmission is not received, enabling a watchdog timer and attempting a shutdown. If the shutdown is not successful, the reset mode further includes determining if the analyte monitoring device 110 is transitioned to a usable state.

In some variations, the power-on event may be the powering on of the microcontroller 510 or the receipt, by the microcontroller 510, of a power-on signal. In some variations, the microcontroller 510 may determine if the battery 460 is the source of the power-on event by a signal between the battery 460 and the microcontroller 510. In some variations, determining the source of the power-on event may include determining whether the analyte monitoring device 110 is transitioned to a usable state. The transition to the usable state may be based on non-analyte sensor data, such as light data, magnetic field data, accelerometer data, and capacitance data as described above.

Figure 8:
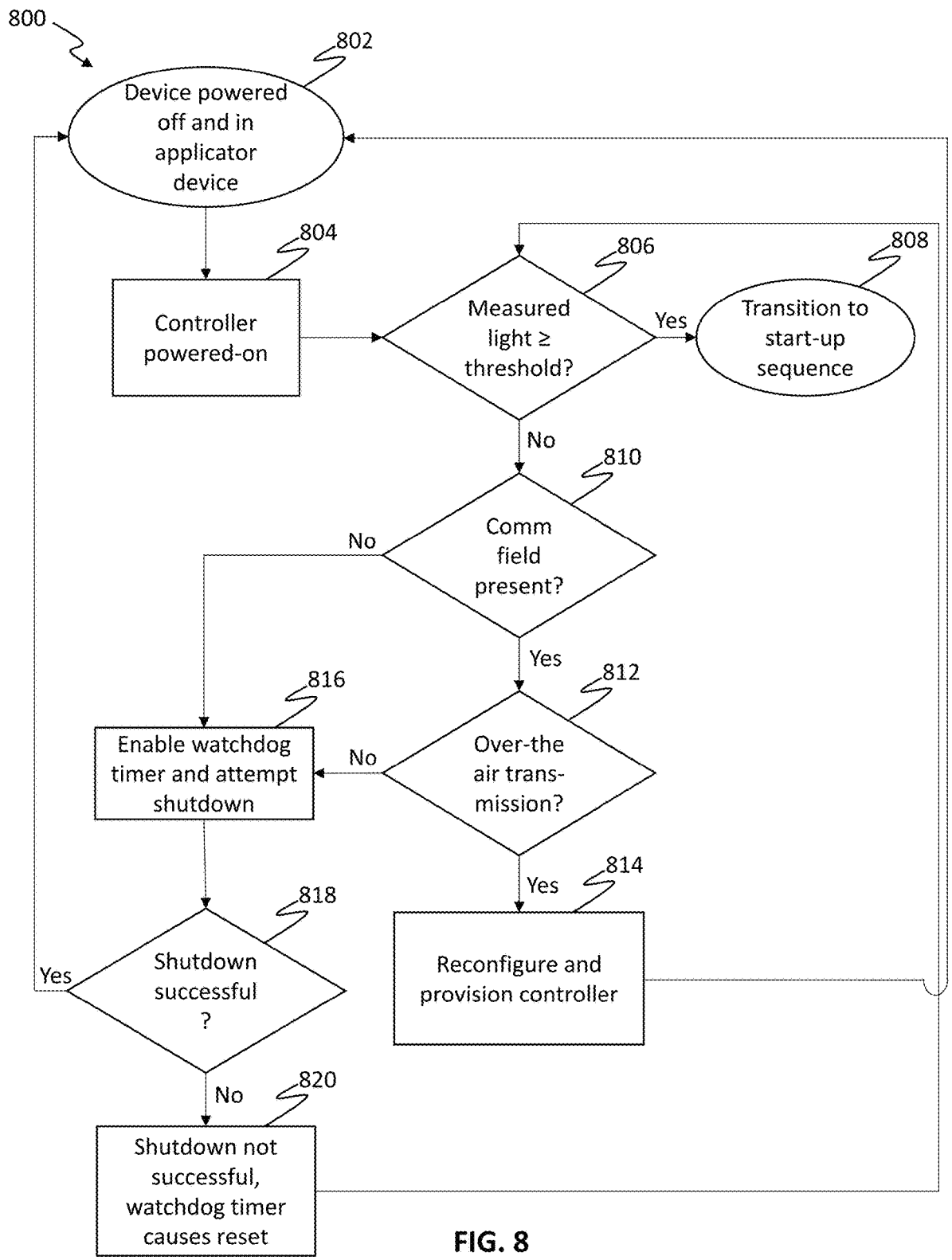
FIG. 8 depicts a flow chart of a power-up process of a sensor assembly in an analyte monitoring device.

FIG. 8 depicts a flow chart 800 of a power-up process of an analyte monitoring device. The power-up process begins at 802 with the analyte monitoring device 110 being powered off and contained in an applicator device.

At 804, the controller is powered on. The powering on begins a process in which the controller determines the source of a power-on event and transitions to a mode of operation corresponding to the determined source. In some variations, if the source is the battery or intentional communication field, the power-on event is considered to be a valid power-on event. In some variations, a power-on event is a valid power-on event if the analyte monitoring device 100 is transitioned to a usable state or if the analyte monitoring device is intentionally positioned in a communication field. In response to either of these valid power-on events, the controller responds by transitioning to a corresponding mode. If the source is an unintentional communication field (e.g., not a valid power-on event), the controller responds by attempting a shutdown within a time period defined by a watchdog timer. If the shutdown is not successful, the process of determining the source of the power-on is repeated.

At 806, the controller uses data from a sensor to determine if the power-on event is a result of the analyte monitoring device 110 being transitioned to a usable state in which the source of the power-on event is a connection with a battery. The usable state may be a state in which the analyte monitoring device 110 is ready to be applied to the user, is removed from an applicator device, or is applied to the user. In some variations, the usable state may be a pre-insertion environment in which the analyte monitoring device 110 is ready for application or a post-insertion environment in which the analyte monitoring device 110 is inserted into the skin surface of the user. In particular at 806, the measured light from an ambient light sensor is compared to a light threshold value. In other variations, alternate or additional data may be used to confirm the transition to the usable state and the connection with the battery.

In the event of an update, such as a firmware update, while the analyte monitoring device 110 remains within the applicator device or other packaging, the measured light is not greater than the light threshold value, and the process continues to 810.

At 810, a determination is made as to whether a communication field is present. If a communication field is detected, by, for example, a measured signal between the controller and the energy harvesting module, the process continues to 812.

At 812, the controller waits for an over-the-air transmission. Upon receipt of the over-the-air transmission, the controller receives reconfiguration parameters of the update. At 814, the controller is reconfigured with the update and is provisioned such that the analyte monitoring device 110 is updated and ready to be powered-off. The process then proceeds to 802, at which point the analyte monitoring device 110 is powered off.

In some situations, the controller may be in the presence of a spurious communication field unintended for the analyte monitoring device 110. In this situation, at 812, after having detected the communication field, the controller waits for the over-the-air transmission. If a predetermined period of time elapses without receiving the over-the-air transmission, the process proceeds to 816.

At 816, a watchdog timer is enabled and shutdown is attempted. The watchdog timer is enabled in the event shutdown is unsuccessful because the analyte monitoring device 110 is powered on and unable to shutdown. For example, the photo detect circuit 610 may have been triggered, causing the connection between the battery 460 and the controller.

At 818, if the controller cannot shutdown (e.g., the attempt to shutdown at 816 was not successful), the process continues to 820. At 820, the watchdog timer causes a reset, and the process continues to 806, at which point the process of comparing a measured light value to a light threshold value is repeated. If the shutdown was successful at 818, the process moves to 802, at which point the analyte monitoring device 110 is in the powered-off state.

In some situations, the controller may be powered on by a communication field that is unintended for the analyte monitoring device 110, but by the time the controller checks for the communication field, it is no longer present. In this situation, the process moves from 810 to 816 to enable the watchdog timer and attempt shutdown.

Figure 9A:
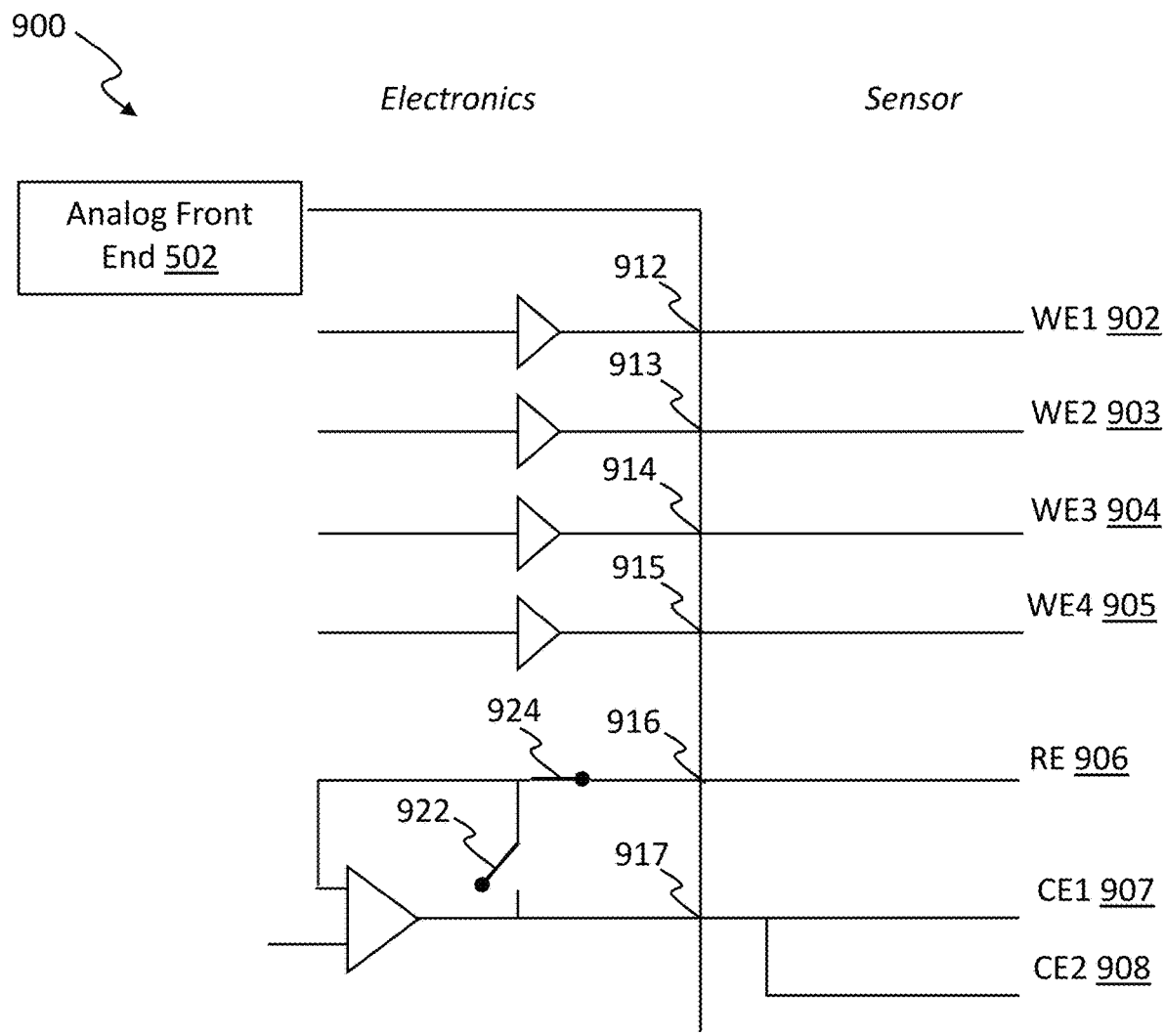
FIGS. 9A and 9B depict an illustrative schematics of microneedle insertion confirmation aspects in an analyte monitoring device.
Figure 9B:
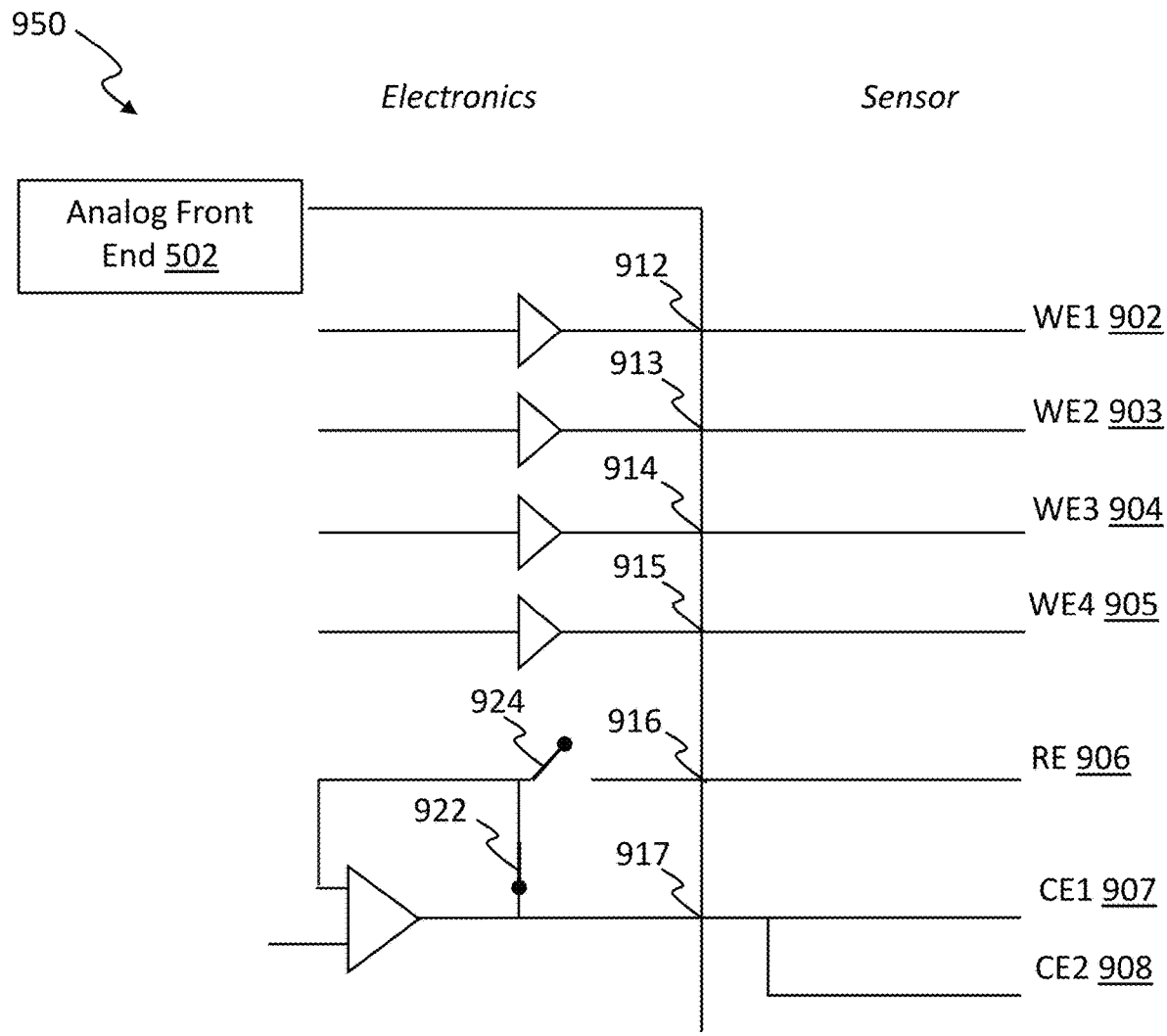

FIGS. 9A and 9B depict illustrative schematics of aspects of an analyte monitoring device for microneedle insertion confirmation.

FIG. 9A depicts an illustrative schematic 900 indicating connection between electronics of an analyte monitoring device and a microneedle array comprised of a plurality of microneedles, each having an electrode positioned on the respective microneedle. The schematic 900 includes a representation of a microneedle array 140 with four working electrodes (a first working electrode needle 902, a second working electrode needle 903, a third working electrode needle 904, and a fourth working electrode needle 905), a reference electrode needle 906, and two counter electrodes (a first counter electrode needle 907 and a second counter electrode needle 908). In some variations, alternate configurations of electrodes are used in the microneedle array 140. For example, some configurations may include fewer or additional working electrodes and counter electrodes. Some configurations may include additional reference electrodes. Details of example configurations of the microneedle array 140 are provided with reference to FIGS. 18A-18J, and other configurations may be used.

In the configuration in the schematic 900, the two counter electrode needles, the first counter electrode needle 907 and the second counter electrode needle 908, are shorted together. In this configurations, the two counter electrode needles function as one counter electrode. In a variation, the microneedle array may include only one counter electrode needle. In some variations, more than two counter electrode needles may be incorporated and shorted together.

Also shown in the schematic 900 are inputs of the analog front end 502 corresponding to the needles of the microneedle array; a first working input 912, a second working input 913, a third working input 914, a fourth working input 915, a reference input 916, and a counter input 917. The counter input 917 corresponds to the shorted together first counter electrode needle 907 and the second counter electrode needle 908. The electronics also includes two switches, a first switch 922 between the counter input 917 and the reference input 916 and a second switch 924 at the reference input 916. The first switch 922 and the second switch 924 are used to configure the analyte monitoring device 110 as a three-electrode system configured to implement the analyte sensing operations described herein (as shown by the schematic 900 of FIG. 9A) and as a two-electrode system, which is depicted by the schematic 950 of FIG. 9B, that may be used for microneedle insertion confirmation as further described herein.

As shown in FIG. 9A, when the first switch 922 is opened and the second switch 924 is closed, the reference input 916 and the counter input 917 are independent of one another. However, a combined counter electrode/reference electrode reference point may be formed by closing the first switch 922 and opening the second switch 924, as shown in FIG. 9B. The combined counter electrode/reference electrode reference point is connected to the counter input 917 of the analog front end and the reference input 916 of the analog front end, and it is this reference point that can be used for applying a bias potential at one or more of the working electrodes. In particular, the analog front end may apply a bias potential between the first working electrode needle 902 and the reference point and measure a resulting current and/or resistance at the first working electrode needle 902.

To confirm insertion of the microneedle array 140, the analog front end 502 applies a bias potential, which may be less than, approximately equal to, equal to, or greater than that of the sensing bias potential applied during analyte sensing. In some variations, the applied bias potential is a value known to not damage the sensing and/or analyte limiting membranes of the working electrode. In some variations, one or more bias potentials are applied. For example, a bias potential may be applied between each working electrode needle 902, 903, 904, and 905 and the reference point.

In some variations, the bias potentials are applied individually. In some variations, the bias potentials are applied sequentially such that one bias potential is applied at a time. Each resulting current and/or resistance is compared to a threshold. The application of the separate bias potentials may provide additional confirmation of the insertion of the microneedle array 140 by, for example, confirming that more than one of the electrodes are inserted at a sufficient depth for sensing.

The resulting current and/or resistance is compared to a predetermined threshold value that indicates a value or a range of values that are indicative of insertion. If the resulting current and/or resistance falls within the range, this serves as an indication that the microneedle array 140 is inserted to a sufficient depth. The analyte monitoring device 110 may be transitioned to an operational mode during which an operating bias potential is applied. If the resulting current is not within the range, the microneedle array 140 may not be at a sufficient depth for sensing of the analyte. An alert may be generated to notify the user. The user may attempt to re-insert the analyte monitoring device 110 and/or apply pressure to the analyte monitoring device 110 to attempt to achieve a sufficient insertion of the microneedle array 140. The alert and/or instructions to apply pressure may be provided on a user interface of the microneedle array and/or on an application (e.g., a mobile app) running on a connected remote device.

In a variation, the operating bias potential is applied to only the working electrode needles 902, 903, 904, or 905 with a resulting current and/or resistance from the applied bias potentials that meet the threshold or fall within the range of thresholds. It may be the case that not all of the working electrode needles are fully inserted at a sufficient depth for sensing, and this allows only those that are fully inserted at the sufficient depth to be used (e.g., the operating bias potential is applied to only those working electrode needles that are determined to be sufficiently inserted based on the resulting current and/or resistance).

In some variations, one or more dedicated electrode needles are used to confirm insertion and one or more others are used for sensing. For example, one of the working electrode needles 902, 903, 904, or 905 is used for applying the bias potential with reference to the reference point. If a current or resistance value resulting from the applied bias potential meets the threshold or falls within the range, the one or more of the other working electrode needles 902, 903, 904, or 905 may be used for sensing operations in which the operating bias potential is applied. In some variations, the one or more working electrode needles used for confirming insertion may include a conducting electrode. In some variations, the one or more working electrode needles used for confirming insertion may include a conducting electrode with one or more other layers disposed thereon as further described herein.

In some variations, prior to applying a first bias potential for insertion confirmation, the combined counter electrode/reference electrode reference point may be formed by closing the first switch 922 and opening the second switch 924. In transitioning the analyte monitoring device 110 to an operational mode, the first switch 922 is opened and the second switch 924 is closed.

In a variation, a confirmation of insertion of a predefined number of working electrode needles is needed to transition the analyte monitoring device 110 to the operation mode. In a variation, at least one working electrode needle needs to be inserted such that the current and/or resistance resulting from the applied bias potential falls meets the threshold or falls within the threshold range. In some variations, a majority (e.g., greater than 50%) or other predefined number of the working electrode needles designated for sensing need to be inserted as confirmed by the applied bias potential measurements. In a variation, a majority (e.g., greater than 50%) or other predefined number of the working electrode needles designated for confirming insertion need to be inserted (as confirmed by the applied bias potential measurements) for the analyte monitoring system 110 to transition to the operating mode.

Once the analyte monitoring device is inserted and warm-up and any calibration has completed, the analyte monitoring device may be ready for providing sensor measurements of a target analyte. The target analyte (and any requisite co-factor(s)) diffuses from the biological milieu, through the biocompatible and diffusion-limiting layers on the working electrode, and to the biorecognition layer including the biorecognition element. In the presence of a co-factor (if present), the biorecognition element may convert the target analyte to an electroactive product.

A bias potential may be applied between the working and reference electrodes of the analyte monitoring device, and an electrical current may flow from the counter electrode to maintain the fixed potential relationship between the working and reference electrodes. This causes the oxidation or reduction of the electroactive product, causing a current to flow between the working electrodes and counter electrodes. The current value is proportional to the rate of the redox reaction at the working electrode and, specifically, to the concentration of the analyte of interest according to the Cottrell relation as described in further detail above.

The electrical current may be converted to a voltage signal by a transimpedance amplifier and quantized to a digital bitstream by means of an analog-to-digital converter (ADC). Alternatively, the electrical current may be directly quantized to a digital bitstream by means of a current-mode ADC. The digital representation of the electrical current may be processed in the embedded microcontroller(s) in the analyte monitoring device and relayed to the wireless communication module for broadcast or transmission (e.g., to one or more peripheral devices). In some variations, the microcontroller may perform additional algorithmic treatment to the data to improve the signal fidelity, accuracy, and/or calibration, etc.

In some variations, the digital representation of the electrical current, or sensor signal, may be correlated to an analyte measurement (e.g., glucose measurement) by the analyte monitoring device. For example, the microcontroller may execute a programmed routine in firmware to interpret the digital signal and perform any relevant algorithms and/or other analysis. Keeping the analysis on-board the analyte monitoring device may, for example, enable the analyte monitoring device to broadcast analyte measurement(s) to multiple devices in parallel, while ensuring that each connected device has the same information. Thus, generally, the user's target analyte (e.g., glucose) values may be estimated and stored in the analyte monitoring device and communicated to one or more peripheral devices.

Data exchange can be initiated by either the mobile application or by the analyte monitoring device. For example, the analyte monitoring device may notify the mobile application of new analyte data as it becomes available. The frequency of updates may vary, for example, between about 5 seconds and about 5 minutes, and may depend on the type of data. Additionally or alternatively, the mobile application may request data from the analyte monitoring device (e.g., if the mobile application identifies gaps in the data it has collected, such as due to disconnections).

If the mobile application is not connected to the analyte monitoring device, the mobile application may not receive data from the sensor electronics. However, the electronics in the analyte monitoring device may store each actual and/or estimated analyte data point. When the mobile application is reconnected to the analyte monitoring device, it may request data that it has missed during the period of disconnection and the electronics on the analyte monitoring device may transmit that set of data as well (e.g., backfill).

Generally, the mobile application may be configured to provide display of real-time or near real-time analyte measurement data, such as on the display of the mobile computing device executing the mobile application. In some variations, the mobile application may communicate through a user interface regarding analysis of the analyte measurement, such as alerts, alarms, insights on trends, etc. such as to notify the user of analyte measurements requiring attention or follow-up action (e.g., high analyte values, low analyte values, high rates of change, analyte values outside of a pre-set range, etc.). In some variations, the mobile application may additionally or alternatively facilitate communication of the measurement data to the cloud for storage and/or archive for later retrieval.

In some variations, the analyte monitoring device may be applied manually. For example, a user may remove a protective film on the adhesive layer and manually press the device onto his or her skin on a desired wear site. As illustrated in FIG. 1, in some variations the analyte monitoring device may be applied to the skin using a suitable applicator 160. The applicator 160 may, for example, be configured to urge the analyte monitoring device 110 toward the skin of the user such that the microneedle array 140 of the analyte monitoring device 110 may be inserted into the skin (e.g., to the desired target depth).

As described above, the analyte monitoring device is applied to the skin of a user such that the microneedle array in the device penetrates the skin and the microneedle array's electrodes are positioned in the upper dermis for access to dermal interstitial fluid. For example, in some variations, the microneedle array may be geometrically configured to penetrate the outer layer of the skin, the stratum corneum, bore through the epidermis, and come to rest within the papillary or upper reticular dermis. The sensing region, confined to the electrode at the distal extent of each microneedle constituent of the array (as described above) may be configured to rest and remain seated in the papillary or upper reticular dermis following application to ensure adequate exposure to circulating dermal interstitial fluid (ISF) without the risk of bleeding or undue influence with nerve endings.

The analyte monitoring device may be applied in any suitable location, though in some variations it may be desirable to avoid anatomical areas of thick or calloused skin (e.g., palmar and plantar regions), or areas undergoing significant flexion (e.g., olecranon or patella). Suitable wear sites may include, for example, on the arm (e.g., upper arm, lower arm), shoulder (e.g., over the deltoid), back of hands, neck, face, scalp, torso (e.g., on the back such as in the thoracic region, lumbar region, sacral region, etc. or on the chest or abdomen), buttocks, legs (e.g., upper legs, lower legs, etc.), and/or top of feet, etc.

In some variations, information relating to analyte measurement data and/or the analyte monitoring device may be communicated via a user interface of the analyte monitoring device. In some variations, the user interface of the analyte monitoring device may be used to communicate information to a user in addition to, or as an alternative to, communicating such information via a peripheral device such as through a mobile application on a computing device. Accordingly, a user and/or those around the user may easily and intuitively view the analyte monitoring device itself for an assessment of analyte measurement data (e.g., analyte measurement status such as current and/or trending analyte measurement levels) and/or device status, without the need to view a separate device (e.g., peripheral device or other device remote from, and in communication with, the analyte monitoring device). Availability of such information directly on the analyte monitoring device itself may also enable a user and/or those around the user to more promptly be alerted of any concerns (e.g., analyte measurements that are above or below target range, and/or analyte measurements that are increasing or decreasing at an alarming rate), thereby enabling a user to take appropriate corrective action more quickly.

In some variations, a photodiode, phototransistor, photodetector, or other suitable ambient light sensor may be employed to measure the illumination level in the device's immediate environment. The ambient light measurement may, for example, be used to trigger an adjustment (e.g., dimming) of the brightness of the user interface (e.g., display, indicator light(s), etc.) to conserve battery charge in a power saving mode, to improve contrast under various illumination scenarios, and/or to reduce device visibility to other individuals. For example, the analyte monitoring device may enter the power saving mode in response to measurements from the ambient light sensor indicating general absence of ambient light (e.g., sufficient darkness for at least a predetermined period of time) such as when the device is placed under the clothing of a wearer or when the wearer is asleep in a dark environment. In these scenarios, the power saving mode may be practical because the indicator lights may have limited utility when concealed and out of view of the wearer (e.g., under clothing) or otherwise may be perceived as an annoyance (e.g., during slumber), etc. In response to measurements from the ambient light sensor indicating exposure to ambient light (e.g., sufficient brightness for at least a predetermined period of time), the analyte monitoring device may then exit the power saving mode and increase the brightness of the user interface accordingly.

In some variations, the mobile application may help a user manage the lifetimes and replacement of analyte monitoring devices. For example, the mobile application may terminate data display when the wear period of the analyte monitoring device has elapsed.

Additionally or alternatively, mobile application may provide configurable alerts to the user that the wear period is about to elapse, which permits users to apply a new analyte monitoring device when the current analyte monitoring device is still active but close to expiry. Additionally, the new analyte monitoring device can warm up (typically between about 30 minutes and about 2 hours) while the old unit is still delivering analyte measurements. The old analyte monitoring device can then be removed upon expiry. The new analyte monitoring device may then become the primary sensor delivering analyte measurements to the mobile application. This may provide for an uninterrupted coverage for analyte measurements. Additionally, the readings from the old analyte monitoring device may be used to calibrate or algorithmically improve the accuracy of the new analyte monitoring device.

In some variations, an analyte monitoring device may have a unique serial number contained within the microcontroller (e.g., located in the electronics system). This serial number may enable sensors to be tracked from manufacturing and throughout the use of the product. For example, sensor device history records including manufacturing and customer use may be transmitted and stored in the cloud database. This enables tracking and inferences to be made on various parameters such as sensor performance metrics and improvement for individual users as well as sensor lots, tracking defective sensor lots back from field data to manufacturing or supplier issues very rapidly, personalized health monitoring features for individual users, etc.

Through web portals, the cloud infrastructure may also allow users to view their real-time and historical glucose data/trends and share the said data with caregivers, their healthcare provider(s), support network, and/or other suitable persons.

The following provides a description of some example aspects of an analyte monitoring device that may be used with the concepts described herein. In particular, the following description includes details of exemplary microneedle arrays, microneedle structures, and electrodes that may be used with the system components of the analyte monitoring device described herein.

Figure 10A:
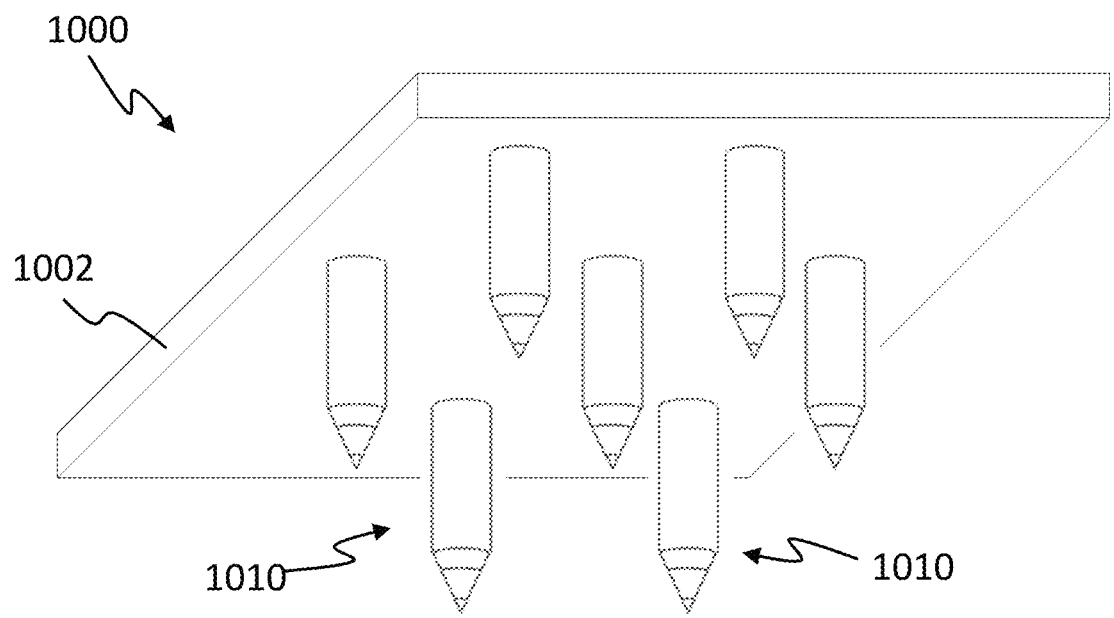
FIG. 10A depicts an illustrative schematic of a microneedle array.
Figure 10B:
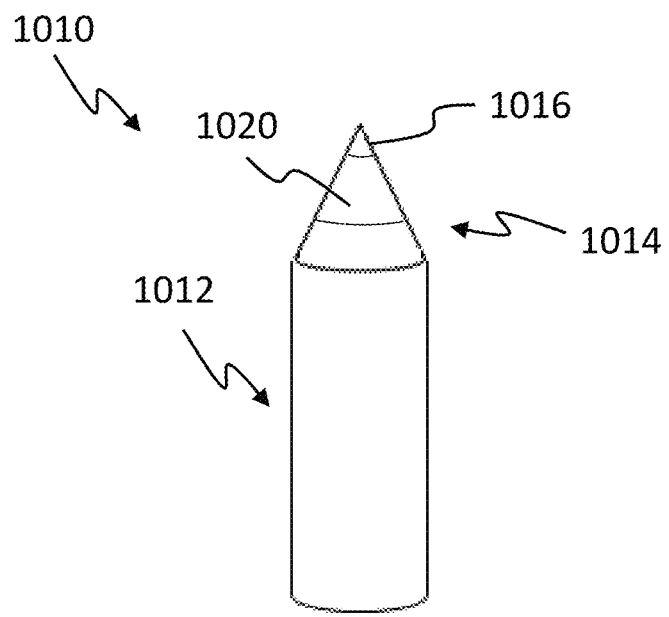
FIG. 10B depicts an illustrative schematic of a microneedle in the microneedle array depicted in FIG. 10A.

As shown in the schematic of FIG. 10A, in some variations, a microneedle array 1010 for use in sensing one or more analytes may include one or more microneedles 1010 projecting from a substrate surface 1002. The substrate surface 1002 may, for example, be generally planar and one or more microneedles 1010 may project orthogonally from the planar surface. Generally, as shown in FIG. 10B, a microneedle 1010 may include a body portion 1012 (e.g., shaft) and a tapered distal portion 1014 configured to puncture skin of a user. In some variations, the tapered distal portion 1014 may terminate in an insulated distal apex 1016. The microneedle 1010 may further include an electrode 1020 on a surface of the tapered distal portion. In some variations, electrode-based measurements may be performed at the interface of the electrode and interstitial fluid located within the body (e.g., on an outer surface of the overall microneedle). In some variations, the microneedle 1010 may have a solid core (e.g., solid body portion), though in some variations the microneedle 1010 may include one or more lumens, which may be used for drug delivery or sampling of the dermal interstitial fluid, for example. Other microneedle variations, such as those described below, may similarly either include a solid core or one or more lumens.

The microneedle array 1000 may be at least partially formed from a semiconductor (e.g., silicon) substrate and include various material layers applied and shaped using various suitable microelectromechanical systems (MEMS) manufacturing techniques (e.g., deposition and etching techniques), as further described below. The microneedle array may be reflow-soldered to a circuit board, similar to a typical integrated circuit. Furthermore, in some variations the microneedle array 1000 may include a three electrode setup including a working (sensing) electrode having an electrochemical sensing coating (including a biorecognition element such as an enzyme) that enables detection of a target analyte, a reference electrode, and a counter electrode. In other words, the microneedle array 1000 may include at least one microneedle 1010 that includes a working electrode, at least one microneedle 1010 including a reference electrode, and at least one microneedle 1010 including a counter electrode. Additional details of these types of electrodes are described in further detail below.

Figure 11:
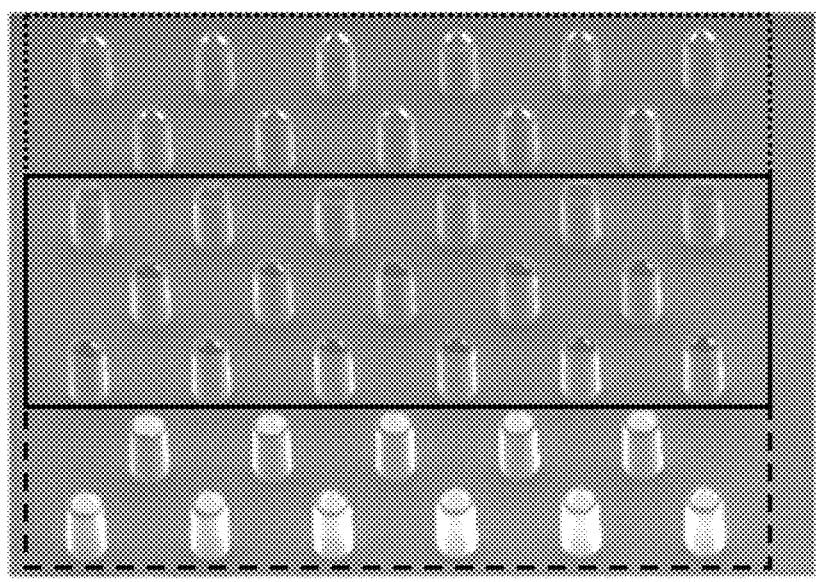
FIG. 11 depicts an illustrative schematic of a microneedle array used for sensing multiple analytes.

In some variations, the microneedle array 1000 may include a plurality of microneedles that are insulated such that the electrode on each microneedle in the plurality of microneedles is individually addressable and electrically isolated from every other electrode on the microneedle array. The resulting individual addressability of the microneedle array 1000 may enable greater control over each electrode's function, since each electrode may be separately probed. For example, the microneedle array 1000 may be used to provide multiple independent measurements of a given target analyte, which improves the device's sensing reliability and accuracy. Furthermore, in some variations the electrodes of multiple microneedles may be electrically connected to produce augmented signal levels. As another example, the same microneedle array 1000 may additionally or alternatively be interrogated to simultaneously measure multiple analytes to provide a more comprehensive assessment of physiological status. For example, as shown in the schematic of FIG. 11, a microneedle array may include a portion of microneedles to detect a first Analyte A, a second portion of microneedles to detect a second Analyte B, and a third portion of microneedles to detect a third Analyte C. It should be understood that the microneedle array may be configured to detect any suitable number of analytes (e.g., 1, 2, 3, 4, 5 or more, etc.). Suitable target analytes for detection may, for example, include glucose, ketones, lactate, and cortisol. For example, in some variations, ketones may be detected in a manner similar to that described in U.S. patent application Ser. No. 16/701,784, which is incorporated herein in its entirety by this reference. Thus, individual electrical addressability of the microneedle array 500 provides greater control and flexibility over the sensing function of the analyte monitoring device.

In some variations of microneedles (e.g., microneedles with a working electrode), the electrode 1020 may be located proximal to the insulated distal apex 1016 of the microneedle. In other words, in some variations the electrode 1020 does not cover the apex of the microneedle. Rather, the electrode 1020 may be offset from the apex or tip of the microneedle. The electrode 1020 being proximal to or offset from the insulated distal apex 1016 of the microneedle advantageously provides more accurate sensor measurements. For example, this arrangement prevents concentration of the electric field at the microneedle apex 1016 during manufacturing, thereby avoiding non-uniform electro-deposition of sensing chemistry on the electrode surface 1020 that would result in faulty sensing.

As another example, placing the electrode 1020 offset from the microneedle apex further improves sensing accuracy by reducing undesirable signal artefacts and/or erroneous sensor readings caused by stress upon microneedle insertion. The distal apex of the microneedle is the first region to penetrate into the skin, and thus experiences the most stress caused by the mechanical shear phenomena accompanying the tearing or cutting of the skin. If the electrode 1020 were placed on the apex or tip of the microneedle, this mechanical stress may delaminate the electrochemical sensing coating on the electrode surface when the microneedle is inserted, and/or cause a small yet interfering amount of tissue to be transported onto the active sensing portion of the electrode. Thus, placing the electrode 1020 sufficiently offset from the microneedle apex may improve sensing accuracy. For example, in some variations, a distal edge of the electrode 1020 may be located at least about 10 μm (e.g., between about 20 μm and about 30 μm) from the distal apex or tip of the microneedle, as measured along a longitudinal axis of the microneedle.

The body portion 1012 of the microneedle 1010 may further include an electrically conductive pathway extending between the electrode 1020 and a backside electrode or other electrical contact (e.g., arranged on a backside of the substrate of the microneedle array). The backside electrode may be soldered to a circuit board, enabling electrical communication with the electrode 1020 via the conductive pathway. For example, during use, the in-vivo sensing current (inside the dermis) measured at a working electrode is interrogated by the backside electrical contact, and the electrical connection between the backside electrical contact and the working electrode is facilitated by the conductive pathway. In some variations, this conductive pathway may be facilitated by a metal via running through the interior of the microneedle body portion (e.g., shaft) between the microneedle's proximal and distal ends. Alternatively, in some variations the conductive pathway may be provided by the entire body portion being formed of a conductive material (e.g., doped silicon). In some of these variations, the complete substrate on which the microneedle array 1000 is built upon may be electrically conductive, and each microneedle 1010 in the microneedle array 1000 may be electrically isolated from adjacent microneedles 1010 as described below. For example, in some variations, each microneedle 1010 in the microneedle array 1000 may be electrically isolated from adjacent microneedles 1010 with an insulative barrier including electrically insulative material (e.g., dielectric material such as silicon dioxide) that surrounds the conductive pathway extending between the electrode 1020 and backside electrical contact. For example, body portion 1012 may include an insulative material that forms a sheath around the conductive pathway, thereby preventing electrical communication between the conductive pathway and the substrate. Other example variations of structures enabling electrical isolation among microneedles are described in further detail below.

Such electrical isolation among microneedles in the microneedle array permits the sensors to be individually addressable. This individually addressability advantageously enables independent and parallelized measurement among the sensors, as well as dynamic reconfiguration of sensor assignment (e.g., to different analytes). In some variations, the electrodes in the microneedle array can be configured to provide redundant analyte measurements, which is an advantage over conventional analyte monitoring devices. For example, redundancy can improve performance by improving accuracy (e.g., averaging multiple analyte measurement values for the same analyte which reduces the effect of extreme high or low sensor signals on the determination of analyte levels) and/or improving reliability of the device by reducing the likelihood of total failure.

In some variations, as described in further detail below with respective different variations of the microneedle, the microneedle array may be formed at least in part with suitable semiconductor and/or MEMS fabrication techniques and/or mechanical cutting or dicing. Such processes may, for example, be advantageous for enabling large-scale, cost-efficient manufacturing of microneedle arrays. For example, in some variations, the microneedle array may be formed at least in part using techniques described in U.S. patent application Ser. No. 15/913,709, which is incorporated herein in its entirety by this reference.

Described herein are multiple example variations of microneedle structure incorporating one or more of the above-described microneedle features for a microneedle array in an analyte monitoring device.

Figure 12A:
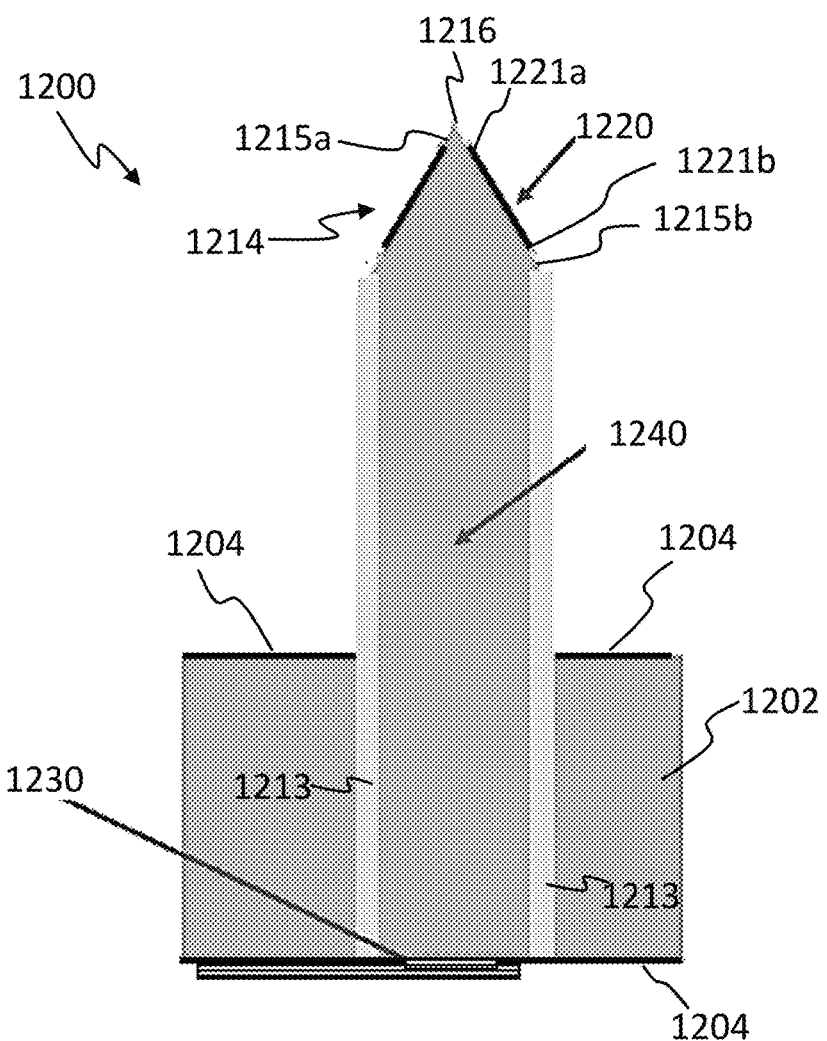
FIG. 12A depicts a cross-sectional side view of a columnar microneedle having a tapered distal end.
Figure 12B:
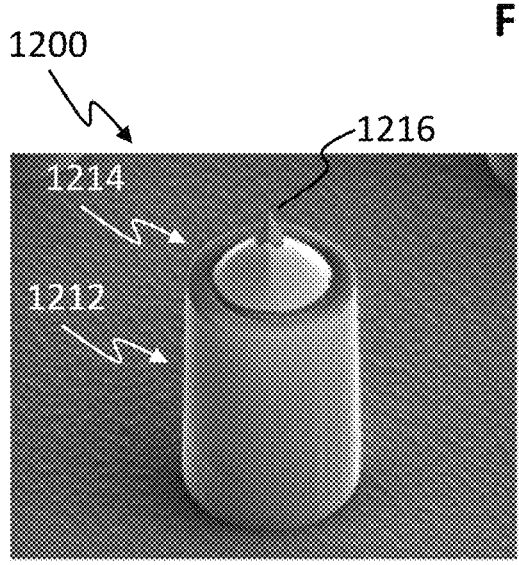
FIGS. 12B and 12C are images depicting perspective and detailed views, respectively, of an embodiment of the microneedle shown in FIG. 12A.
Figure 12C:
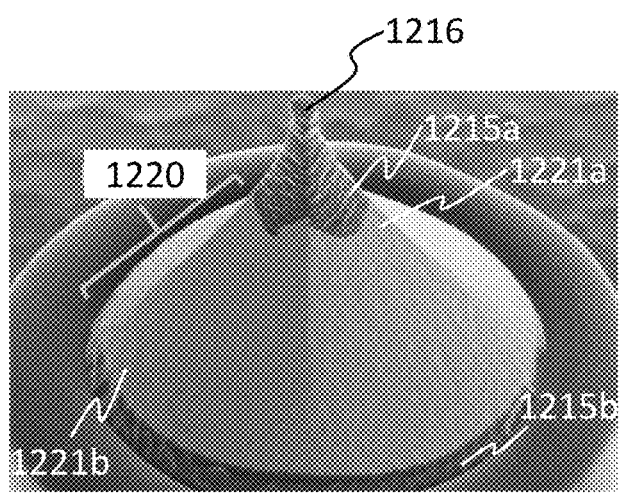

In some variations, a microneedle may have a generally columnar body portion and a tapered distal portion with an electrode. For example, FIGS. 12A-12C illustrate an example variation of a microneedle 1200 extending from a substrate 1202. FIG. 12A is a side cross-sectional view of a schematic of microneedle 1200, while FIG. 12B is a perspective view of the microneedle 1200 and FIG. 12C is a detailed perspective view of a distal portion of the microneedle 1200. As shown in FIGS. 12B and 12C, the microneedle 1200 may include a columnar body portion 1212, a tapered distal portion 1214 terminating in an insulated distal apex 1216, and an annular electrode 1220. The annular electrode 1220 includes a conductive material (e.g., Pt, Ir, Au, Ti, Cr, Ni, combinations thereof, etc.) arranged on the tapered distal portion 1214, such as, for example, on a segment thereof, and comprises a distal edge 1221a and a proximal edge 1221b. As shown in FIG. 12A, the annular electrode 1220 may be proximal to (offset or spaced apart from) the distal apex 1216. The annular electrode 1220 may be electrically isolated from the distal apex 1216 by a distal insulating surface 1215a including an insulating material (e.g., SiO2). For example, the distal edge 1221a of the annular electrode 1220 may be proximate to a proximal edge of the distal insulating surface 1215a of the insulated distal apex 1216. In some variations, the distal edge 1221a of the annular electrode 1220 may be proximal to (e.g., just proximal to, adjacent, abutting) a proximal edge of the distal apex 1216 (a proximal edge of the distal insulating surface 1215a), while in other variations, the distal edge 1221a of the annular electrode 1220 may be distal to (e.g., just distal to, adjacent) the proximal edge of the insulated distal apex 1216 (proximal edge of the distal insulating surface 1215a), but may remain proximal to the apex itself. Accordingly, in some variations, the annular electrode 1220 may overlie a portion of the distal insulating surface 1215a, but may remain proximal to (and offset from) the insulated distal apex itself.

Also as shown in FIG. 12A, the proximal edge 1221b of the annular electrode 1220 may be distal to, and in some variations, offset or spaced apart from, the columnar body portion 1212. In some variations, the proximal edge 1221b of the annular electrode 1220 may also be electrically isolated from the columnar body portion 1212 by a second distal insulating surface 1215b comprising an insulating material (e.g., SiO2) at a proximal end or region of the tapered distal portion 1214. For example, the proximal edge 1221b of the annular electrode 1220 may be proximate to a distal edge of the second distal insulating surface 1215b. In some variations, the proximal edge 1221b of the annular electrode 1220 may be proximal to (e.g., just proximal to, adjacent, abutting) a distal edge the second distal insulating surface 1215b, while in other variations, the proximal edge 1221b of the annular electrode 1220 may be distal to (e.g., just distal to, adjacent) the distal edge of the second distal insulating surface 1215b, but may remain proximal to the columnar body portion 1212. Accordingly, in some variations, the annular electrode 1220 may overlie a portion of the second distal insulating surface 1215b but may remain proximal to (and offset from) the columnar body portion 1212. As shown in FIG. 12A and in some other variations, the annular electrode 1220 may be on only a segment of the surface of the tapered distal portion 1214, and may or may not extend to the columnar boy portion 1212.

The electrode 1220 may be in electrical communication with a conductive core 1240 (e.g., conductive pathway) passing along the body portion 1212 to a backside electrical contact 1230 (e.g., made of Ni/Au alloy) or other electrical pad in or on the substrate 1202. For example, the body portion 1212 may include a conductive core material (e.g., highly doped silicon). As shown in FIG. 12A, in some variations, an insulating moat 1213 including an insulating material (e.g., SiO2) may be arranged around (e.g., around the perimeter) of the body portion 1212 and extend at least partially through the substrate 1202. Accordingly, the insulating moat 1213 may, for example, help prevent electrical contact between the conductive core 1240 and the surrounding substrate 1202. The insulating moat 1213 may further extend over the surface of the body portion 1212. Upper and/or lower surfaces of the substrate 1202 may also include a layer of substrate insulation 1204 (e.g., SiO2). Accordingly, the insulation provided by the insulating moat 1213 and/or substrate insulation 1204 may contribute at least in part to the electrical isolation of the microneedle 1200 that enables individual addressability of the microneedle 1200 within a microneedle array. Furthermore, in some variations the insulating moat 1213 extending over the surface of the body portion 1212 may function to increase the mechanical strength of the microneedle 1200 structure.

The microneedle 1200 may be formed at least in part by suitable MEMS fabrication techniques such as plasma etching, also called dry etching. For example, in some variations, the insulating moat 1213 around the body portion 1212 of the microneedle may be made by first forming a trench in a silicon substrate by deep reactive ion etching (DRIE) from the backside of the substrate, then filling that trench with a sandwich structure of SiO2/polycrystalline silicon (poly-Si)/SiO2 by low pressure chemical vapor deposition (LPCVD) or other suitable process. In other words, the insulating moat 1213 may passivate the surface of the body portion 1212 of the microneedle, and continue as a buried feature in the substrate 1202 near the proximal portion of the microneedle. By including largely compounds of silicon, the insulating moat 1213 may provide good fill and adhesion to the adjoining silicon walls (e.g., of the conductive core 1240, substrate 1202, etc.). The sandwich structure of the insulating moat 1213 may further help provide excellent matching of coefficient of thermal expansion (CTE) with the adjacent silicon, thereby advantageously reducing faults, cracks, and/or other thermally-induced weaknesses in the insulating structure 1213.

The tapered distal portion may be fashioned out by an isotropic dry etch from the frontside of the substrate, and the body portion 1212 of the microneedle 1200 may be formed from DRIE. The frontside metal electrode 1220 may be deposited and patterned on the distal portion by specialized lithography (e.g., electron-beam evaporation) that permits metal deposition in the desired annular region for the electrode 1220 without coating the distal apex 1216. Furthermore, the backside electrical contact 1230 of Ni/Au may be deposited by suitable MEMS manufacturing techniques (e.g., sputtering).

Figure 13:
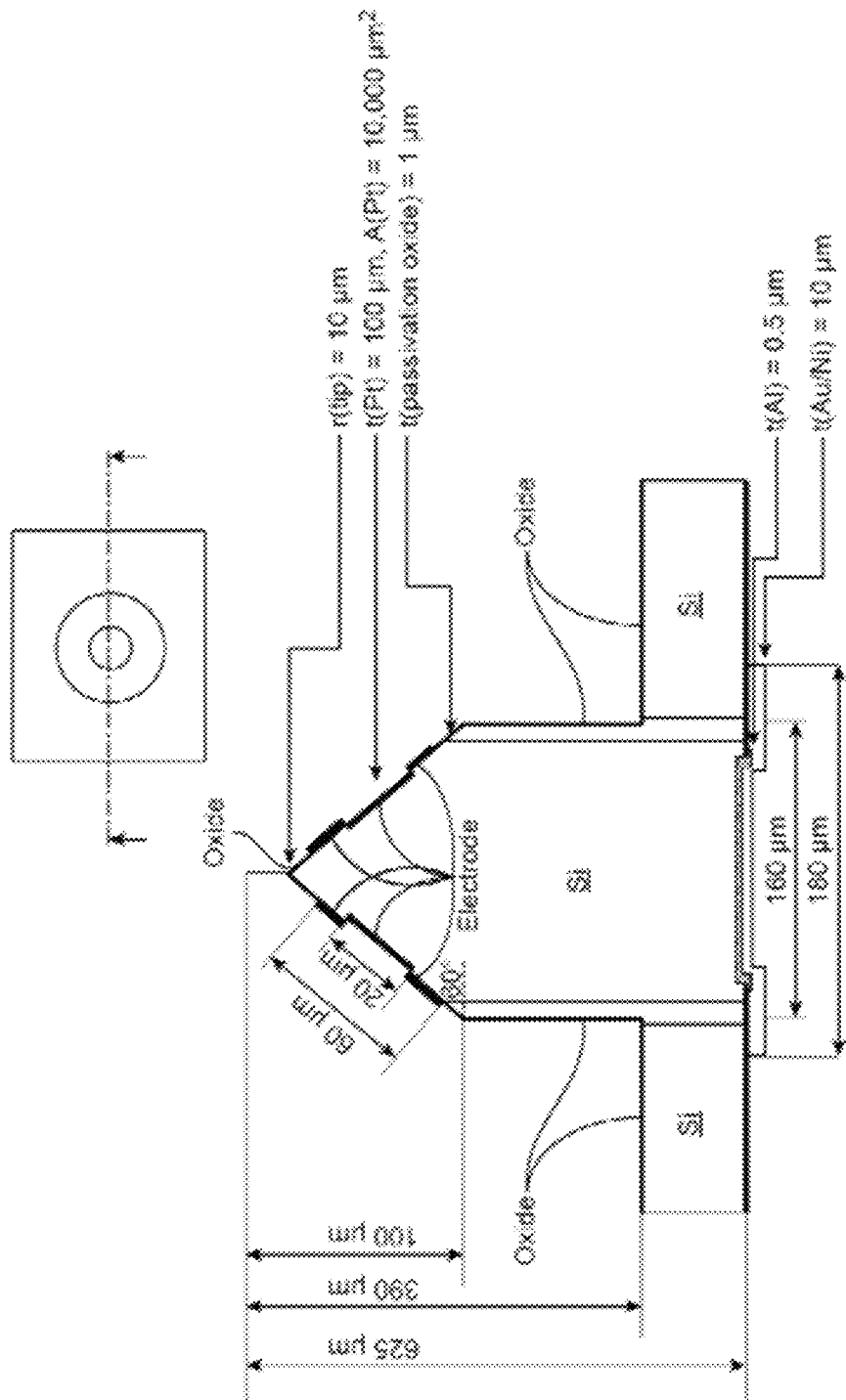
FIG. 13 depicts an illustrative schematic of a columnar microneedle having a tapered distal end.

The microneedle 1200 may have any suitable dimensions. By way of illustration, the microneedle 1200 may, in some variations, have a height of between about 300 µm and about 500 µm. In some variations, the tapered distal portion 1214 may have a tip angle between about 60 degrees and about 80 degrees, and an apex diameter of between about 1 µm and about 15 µm. In some variations, the surface area of the annular electrode 1220 may include between about 9,000 µm$^2$ and about 11,000 µm$^2$, or about 10,000 µm$^2$. FIG. 13 illustrates various dimensions of an example variation of a columnar microneedle with a tapered distal portion and annular electrode, similar to microneedle 1200 described above. As with the microneedle 1200 described above, the columnar microneedle of FIG. 13 comprises a columnar body portion, a tapered distal portion terminating in an insulated distal apex, a contact trench formed within the tapered distal portion, and an annular electrode (denoted by "Pt" in FIG. 13) that is arranged on the tapered distal portion and overlays the contact trench. The annular electrode may comprise a conductive material (e.g., Pt, Ir, Au, Ti, Cr, Ni, combinations thereof, etc.). In some variations, the contact trench may have a width of about 1 µm, about 2 µm, about 3 µm, about 4 µm, about 5 µm, about 10 µm, about 15 µm, about 20 µm, about 25 µm, about 30 µm, about 35 µm, about 40 µm, about 45 µm, about 50 µm, or, as shown in FIG. 13, about 20 µm. The annular electrode may comprise a distal edge and a proximal edge, and in some variations, a distance between the distal edge and the proximal edge of the annular electrode may be about 20 µm, about 30 µm, about 40 µm about 50 µm, about 60 µm, about 70 µm, about 80 µm, about 90 µm, about 100 µm, or, as shown in FIG. 13, about 60 µm. In some variations, and as shown in FIG. 13 by the dimensional callouts 60 µm and 20 µm, the annular electrode may overlie the contact trench and, in some instances, a portion of the insulating surfaces (denoted by "Oxide" in FIG. 13) of the tapered distal portion.

Figure 14A:
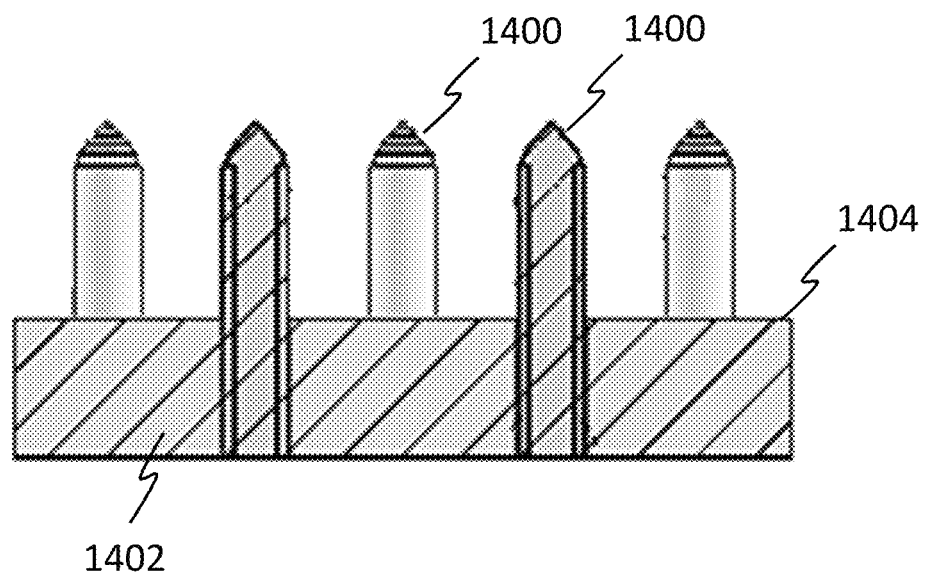
FIGS. 14A and 14B depict illustrative schematics of a microneedle array and a microneedle, respectively.
Figure 14B:
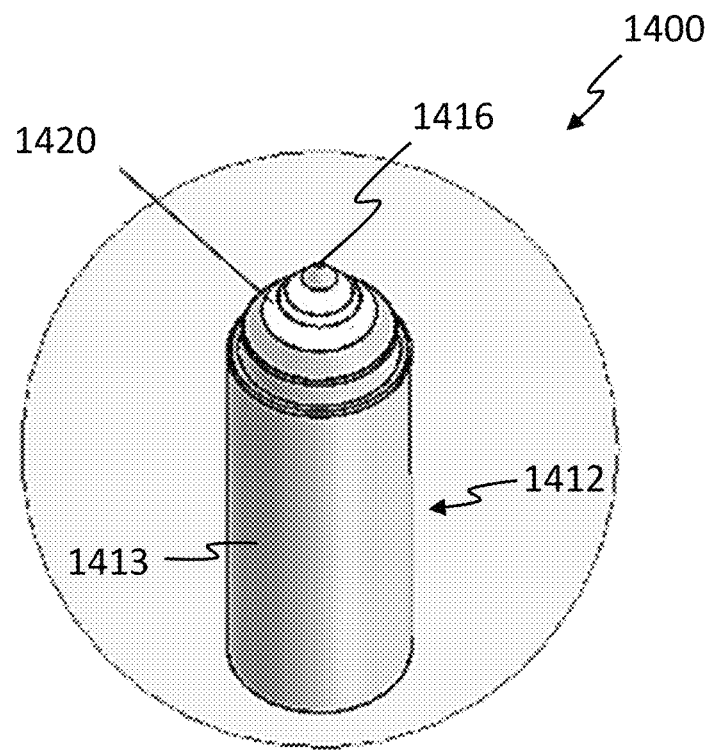
Figure 14C:
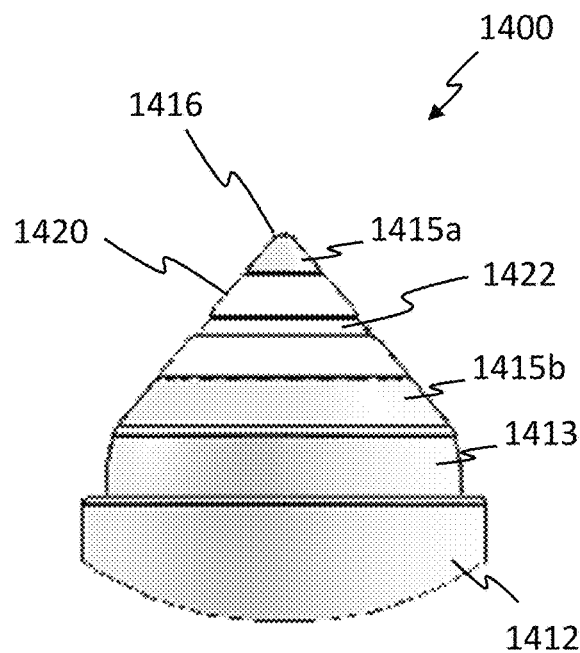
FIGS. 14C-14F depict detailed partial views of an illustrative variation of a microneedle.
Figure 14D:
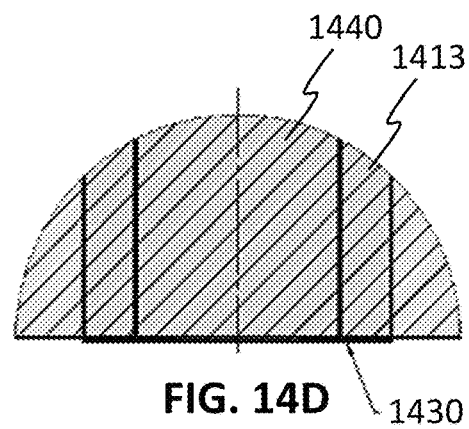
Figure 14E:
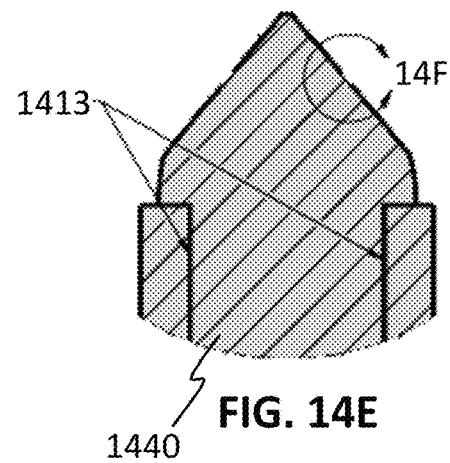
Figure 14F:
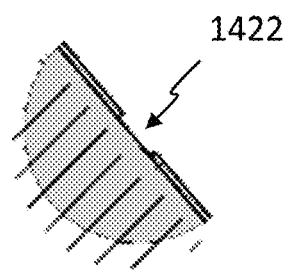

FIGS. 14A-14F illustrate another example variation of a microneedle 1400 having a generally columnar body portion. The microneedle 1400 may be similar to microneedle 1000 as described above, except as described below. For example, as shown in FIG. 14B, like the microneedle 1200, the microneedle 1400 may include a columnar body portion 1412, and a tapered distal portion arranged on a cylinder 1413 and terminating in an insulated distal apex 1416. The cylinder 1413 may be insulated and have a smaller diameter than the columnar body portion 1412. The microneedle 1400 may further include an annular electrode 1420 that includes a conductive material and is arranged on the tapered distal portion at a location proximal to (or offset or spaced apart from) the distal apex 1416. Other elements of microneedle 1400 as shown in FIGS. 14A-14F have numbering similar to corresponding elements of microneedle 1000.

However, the electrode 1420 on the microneedle 1400 may include a tip contact trench 1422. This contact trench may be configured to help establish ohmic contact between the electrode 1420 and the underlying conductive core 1440 of the microneedle. In some variations, the shape of the tip contact trench 1422 may include an annular recess formed in the surface of the conductive core 1440 (e.g., into the body portion of the microneedle, or otherwise in contact with a conductive pathway in the body portion) such that when the electrode 1420 material is deposited onto the conductive core 1440, the electrode 1420 with the tip contact trench 1422 may have a stepped profile when viewed from the side. The tip contact trench 1422 may advantageously help provide a margin of error to ensure contact between the electrode 1420 and the underlying conductive core 1440. Any of the other microneedle variations described herein may also have a similar tip contact trench to help ensure contact between the electrode (which may be, for example, a working electrode, reference electrode, counter electrode, etc.) with a conductive pathway within the microneedle.

Figure 15A:
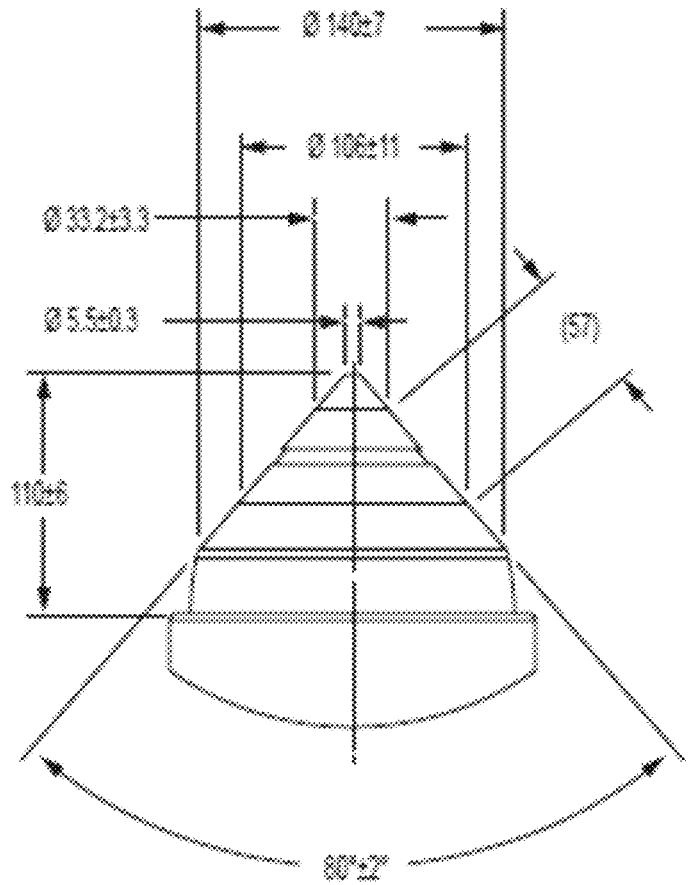
FIGS. 15A and 15B depict an illustrative variation of a microneedle.
Figure 15B:
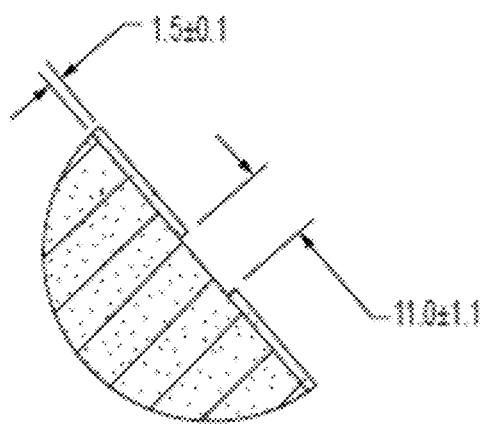

FIGS. 15A and 15B illustrate additional various dimensions of an example variation of a columnar microneedle with a tapered distal portion and annular electrode, similar to microneedle 1400 described above. For example, the variation of the microneedle shown in FIGS. 15A and 15B may have a tapered distal portion generally having a taper angle of about 80 degrees (or between about 78 degrees and about 82 degrees, or between about 75 degrees and about 85 degrees), and a cone diameter of about 140 µm (or between about 133 µm and about 147 µm, or between about 130 µm and about 150 µm). The cone of the tapered distal portion may be arranged on a cylinder such that the overall combined height of the cone and cylinder is about 110 µm (or between about 99 µm and about 116 µm, or between about 95 µm and about 120 µm). The annular electrode on the tapered distal portion may have an outer or base diameter of about 106 µm (or between about 95 µm and about 117 µm, or between about 90 µm and about 120 µm), and an inner diameter of about 33.2 µm (or between about 30 µm and about 36 µm, or between about 25 µm and about 40 µm). The length of the annular electrode, as measured along the slope of the tapered distal portion, may be about 57 µm (or between about 55 µm and about 65 µm), and the overall surface area of the electrode may be about 12,700 µm$^2$ (or between about 12,500 µm$^2$ and about 12,900 µm$^2$, or between about 12,000 µm$^2$ and about 13,000 µm$^2$). As shown in FIG. 15B, the electrode may furthermore have a tip contact trench extending around a central region of the cone of the tapered distal portion, where the contact may have a width of about 11 µm (or between about 5 µm and about 50 µm, between about 10 µm and about 12 µm, or between about 8 µm and about 14 µm) as measured along the slope of the tapered distal portion, and a trench depth of about 1.5 µm (or between about 0.1 µm and about 5 µm, or between about 0.5 µm and about 1.5 µm, or between about 1.4 µm and about 1.6 µm, or between about 1 µm and about 2 µm). The microneedle has an insulated distal apex having a diameter of about 5.5 µm (or between about 5.3 µm and about 5.8 µm, or between about 5 µm and about 6 µm).

Details of example variations of microneedle array configurations are described in further detail below.

Multiple microneedles (e.g., any of the microneedle variations described herein, each of which may have a working electrode, counter electrode, or reference electrode as described above) may be arranged in a microneedle array. Considerations of how to configure the microneedles include factors such as desired insertion force for penetrating skin with the microneedle array, optimization of electrode signal levels and other performance aspects, manufacturing costs and complexity, etc.

For example, the microneedle array may include multiple microneedles that are spaced apart at a predefined pitch (distance between the center of one microneedle to the center of its nearest neighboring microneedle). In some variations, the microneedles may be spaced apart with a sufficient pitch so as to distribute force (e.g., avoid a "bed of nails" effect) that is applied to the skin of the user to cause the microneedle array to penetrate the skin. As pitch increases, force required to insert the microneedle array tends to decrease and depth of penetration tends to increase. However, it has been found that pitch only begins to affect insertion force at low values (e.g., less than about 150 µm). Accordingly, in some variations the microneedles in a microneedle array may have a pitch of at least 200 µm, at least 300 µm, at least 400 µm, at least 500 µm, at least 600 µm, at least 700 µm, or at least 750 µm. For example, the pitch may be between about 200 µm and about 800 µm, between about 300 µm and about 700 µm, or between about 400 µm and about 600 µm. In some variations, the microneedles may be arranged in a periodic grid, and the pitch may be uniform in all directions and across all regions of the microneedle array. Alternatively, the pitch may be different as measured along different axes (e.g., X, Y directions) and/or some regions of the microneedle array may include a smaller pitch while other may include a larger pitch.

Furthermore, for more consistent penetration, microneedles may be spaced equidistant from one another (e.g., same pitch in all directions). To that end, in some variations, the microneedles in a microneedle array may be arranged in a hexagonal configuration as shown in FIGS. 16A-16C, 17A-17B, and 18A-18J. Alternatively, the microneedles in a microneedle array may arranged in a rectangular array (e.g., square array), or in another suitable symmetrical manner.

Another consideration for determining configuration of a microneedle array is overall signal level provided by the microneedles. Generally, signal level at each microneedle is invariant of the total number of microneedle elements in an array. However, signal levels can be enhanced by electrically interconnecting multiple microneedles together in an array. For example, an array with a large number of electrically connected microneedles is expected to produce a greater signal intensity (and hence increased accuracy) than one with fewer microneedles. However, a higher number of microneedles on a die will increase die cost (given a constant pitch) and will also require greater force and/or velocity to insert into skin. In contrast, a lower number of microneedles on a die may reduce die cost and enable insertion into the skin with reduced application force and/or velocity. Furthermore, in some variations a lower number of microneedles on a die may reduce the overall footprint area of the die, which may lead to less unwanted localized edema and/or erythema. Accordingly, in some variations, a balance among these factors may be achieved with a microneedle array including 37 microneedles as shown in FIGS. 17A-17B or a microneedle array including seven microneedles as shown in FIGS. 16A-16D. However, in other variations there may be fewer microneedles in an array (e.g., between about 5 and about 35, between about 5 and about 30, between about 5 and about 25, between about 5 and about 20, between about 5 and about 15, between about 5 and about 100, between about 10 and about 30, between about 15 and about 25, etc.) or more microneedles in an array (e.g., more than 37, more than 40, more than 45, etc.).

Additionally, as described in further detail below, in some variations only a subset of the microneedles in a microneedle array may be active during operation of the analyte monitoring device. For example, a portion of the microneedles in a microneedle array may be inactive (e.g., no signals read from electrodes of inactive microneedles). In some variations, a portion of the microneedles in a microneedle array may be activated at a certain time during operation and remain active for the remainder of the operating lifetime of the device. Furthermore, in some variations, a portion of the microneedles in a microneedle array may additionally or alternatively be deactivated at a certain time during operation and remain inactive for the remainder of the operating lifetime of the device.

In considering characteristics of a die for a microneedle array, die size is a function of the number of microneedles in the microneedle array and the pitch of the microneedles. Manufacturing costs are also a consideration, as a smaller die size will contribute to lower cost since the number of dies that can be formed from a single wafer of a given area will increase. Furthermore, a smaller die size will also be less susceptible to brittle fracture due to the relative fragility of the substrate.

Furthermore, in some variations, microneedles at the periphery of the microneedle array (e.g., near the edge or boundary of the die, near the edge or boundary of the housing, near the edge or boundary of an adhesive layer on the housing, along the outer border of the microneedle array, etc.) may be found to have better performance (e.g., sensitivity) due to better penetration compared to microneedles in the center of the microneedle array or die. Accordingly, in some variations, working electrodes may be arranged largely or entirely on microneedles located at the periphery of the microneedle array, to obtain more accurate and/or precise analyte measurements.

FIGS. 17A and 17B depict an illustrative schematic of 37 microneedles arranged in an example variation of a microneedle array 1700. The 37 microneedles may, for example, be arranged in a hexagonal array with an inter-needle center-to-center pitch of about 750 μm (or between about 700 μm and about 800 μm, or between about 725 μm and about 775 μm) between the center of each microneedle and the center of its immediate neighbor in any direction. FIG. 17A depicts an illustrative schematic of an example variation of a die including the microneedle arrangement. Example dimensions of the die (e.g., about 4.4 mm by about 5.0 mm) and the microneedle array 1700 are shown in FIG. 17B.

Figure 16A:
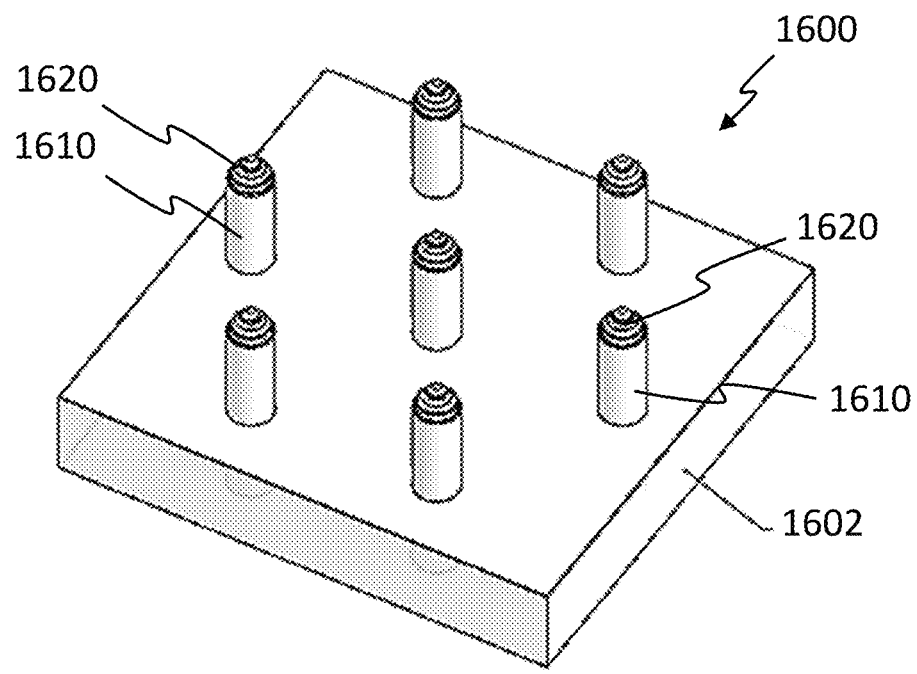
FIGS. 16A and 16B depict illustrative schematics of a microneedle array configuration.
Figure 16B:
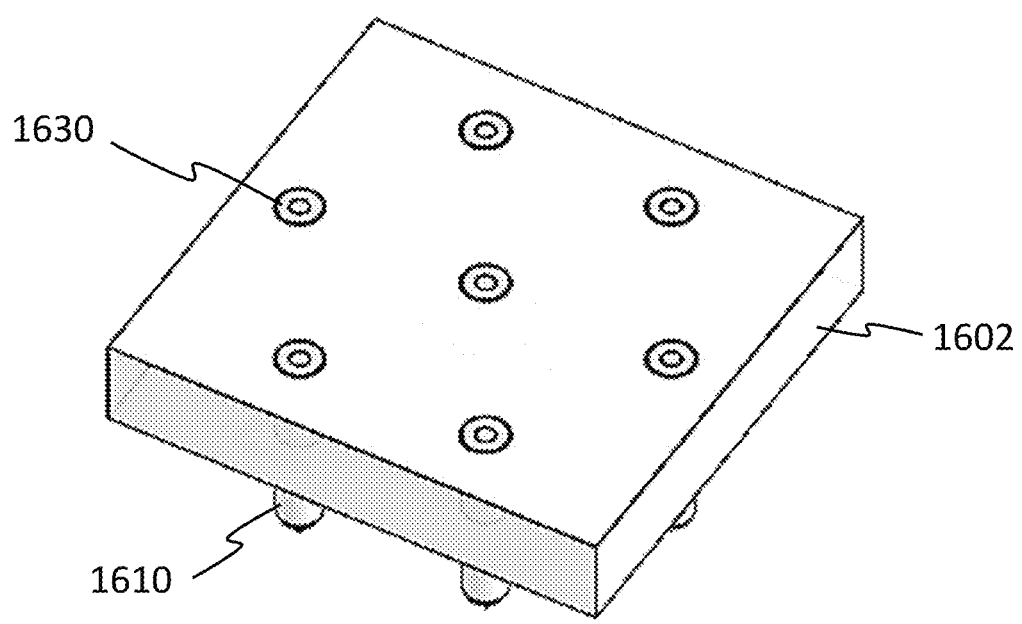
Figure 16C:
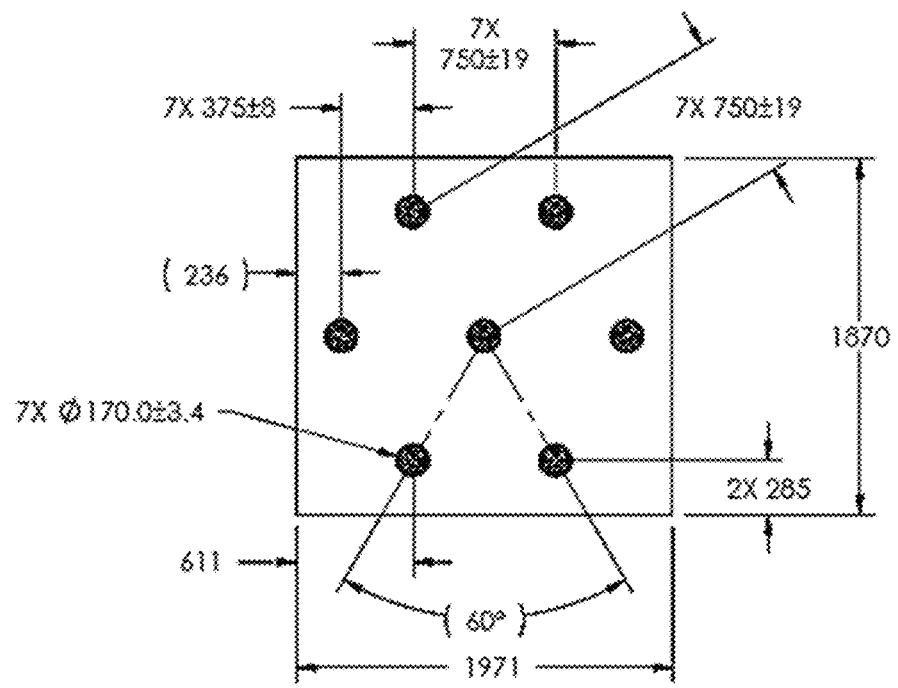
FIGS. 16C and 16D depict illustrative schematics of a microneedle array configuration.
Figure 16D:
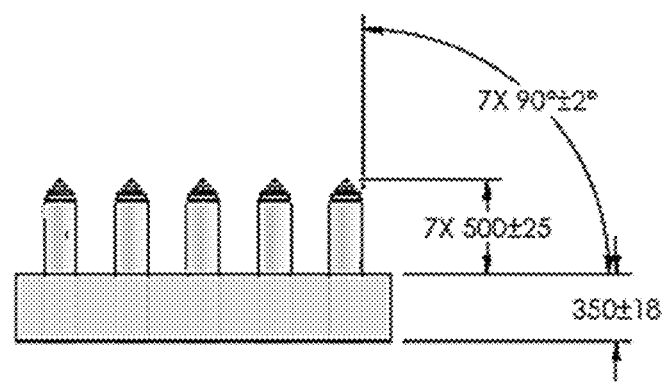
Figure 17A:
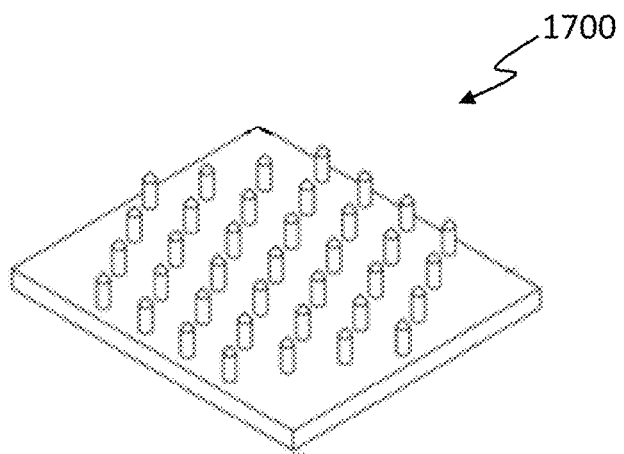
FIGS. 17A and 17B depict perspective and orthogonal views, respectively, of an illustrative variation of a die including a microneedle array.
Figure 17B:
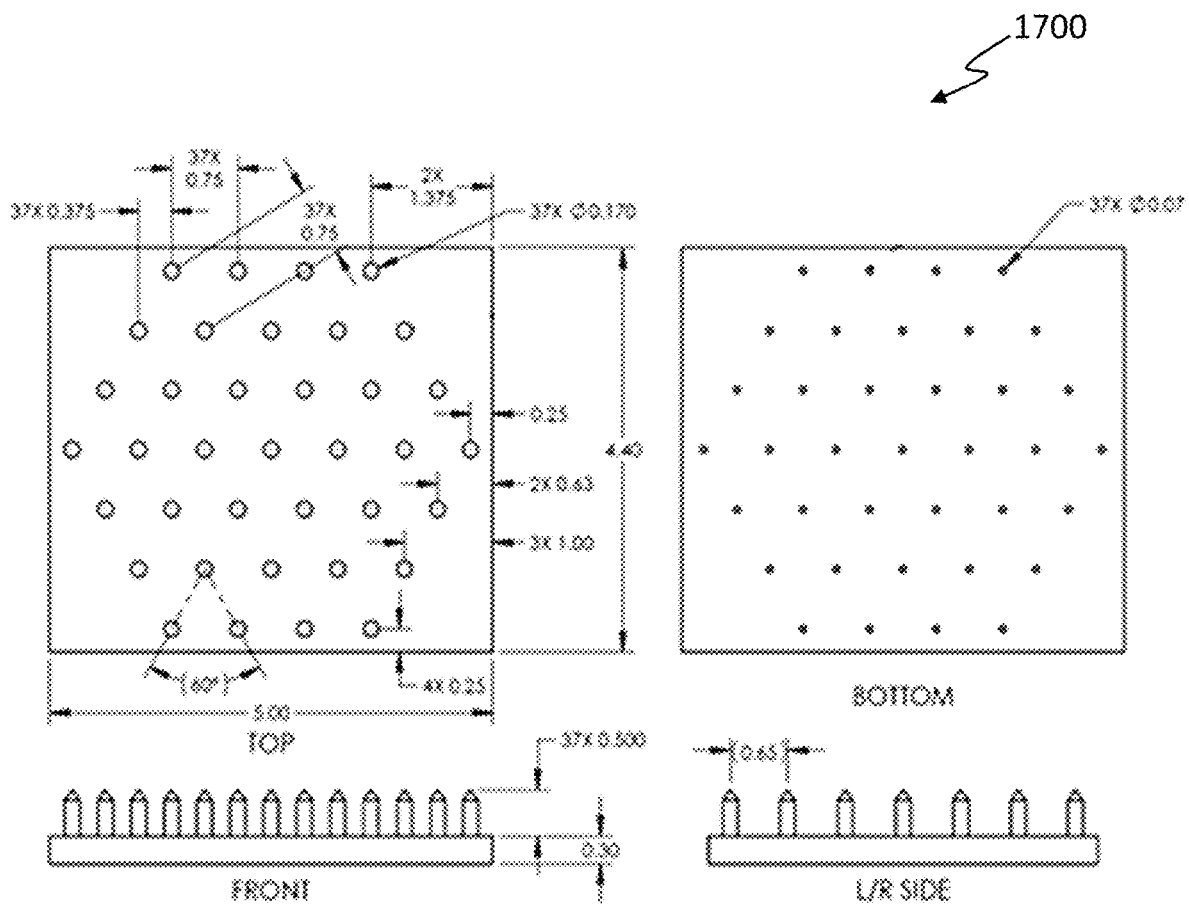

FIGS. 16A and 16B depict perspective views of an illustrative schematic of seven microneedles 1610 arranged in an example variation of a microneedle array 1600. The seven microneedles 1610 are arranged in a hexagonal array on a substrate 1602. As shown in FIG. 16A, the electrodes 1620 are arranged on distal portions of the microneedles 1610 extending from a first surface of the substrate 1602. As shown in FIG. 16B, proximal portions of the microneedles 1610 are conductively connected to respective backside electrical contacts 1630 on a second surface of the substrate 1602 opposite the first surface of the substrate 1602. FIGS. 16C and 16D depict plan and side views of an illustrative schematic of a microneedle array similar to microneedle array 1600. As shown in FIGS. 16C and 16D, the seven microneedles are arranged in a hexagonal array with an inter-needle center-to-center pitch of about 750 μm between the center of each microneedle and the center of its immediate neighbor in any direction. In other variations the inter-needle center-to-center pitch may be, for example, between about 700 μm and about 800 μm, or between about 725 μm and about 775 μm. The microneedles may have an approximate outer shaft diameter of about 170 μm (or between about 150 μm and about 190 μm, or between about 125 μm and about 200 μm) and a height of about 500 μm (or between about 475 μm and about 525 μm, or between about 450 μm and about 550 μm).

Furthermore, the microneedle arrays described herein may have a high degree of configurability concerning where the working electrode(s), counter electrode(s), and reference electrode(s) are located within the microneedle array. This configurability may be facilitated by the electronics system.

Figure 18A:
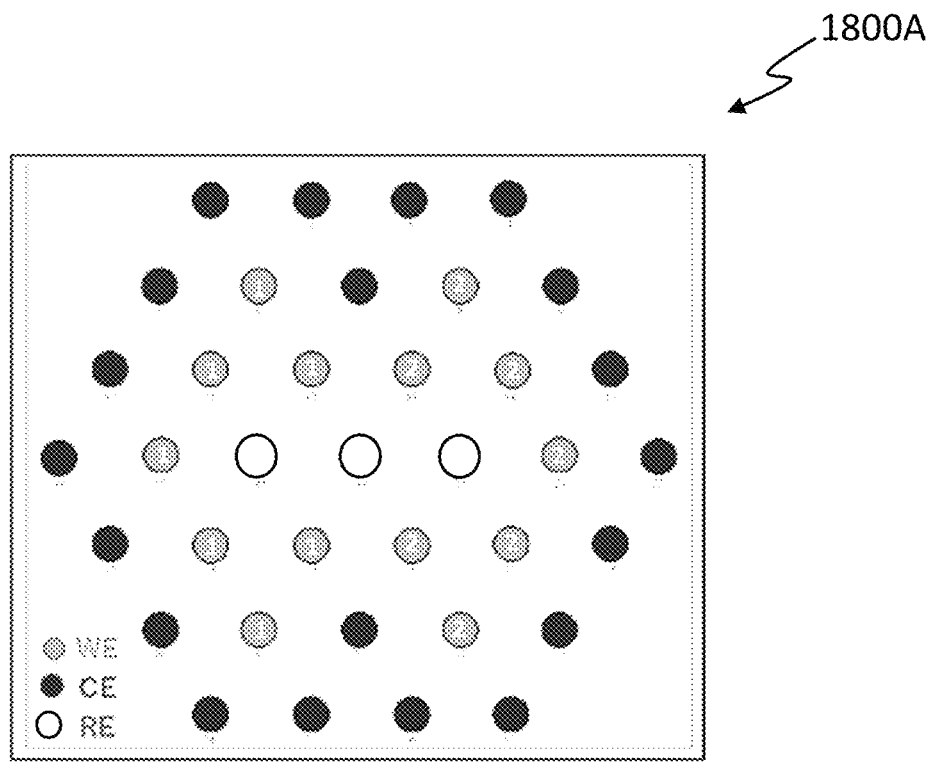
FIGS. 18A-18J depict illustrative schematics of different variations of microneedle array configurations.

In some variations, a microneedle array may include electrodes distributed in two or more groups in a symmetrical or non-symmetrical manner in the microneedle array, with each group featuring the same or differing number of electrode constituents depending on requirements for signal sensitivity and/or redundancy. For example, electrodes of the same type (e.g., working electrodes) may be distributed in a bilaterally or radially symmetrical manner in the microneedle array. For example, FIG. 18A depicts a variation of a microneedle array 1800A including two symmetrical groups of seven working electrodes (WE), with the two working electrode groups labeled "1" and "2". In this variation, the two working electrode groups are distributed in a bilaterally symmetrical manner within the microneedle array. The working electrodes are generally arranged between a central region of three reference electrodes (RE) and an outer perimeter region of twenty counter electrodes (CE). In some variations, each of the two working electrode groups may include seven working electrodes that are electrically connected amongst themselves (e.g., to enhance sensor signal). Alternatively, only a portion of one or both of the working electrode groups may include multiple electrodes that are electrically connected amongst themselves. As yet another alternative, the working electrode groups may include working electrodes that are standalone and not electrically connected to other working electrodes. Furthermore, in some variations the working electrode groups may be distributed in the microneedle array in a non-symmetrical or random configuration.

Figure 18B:
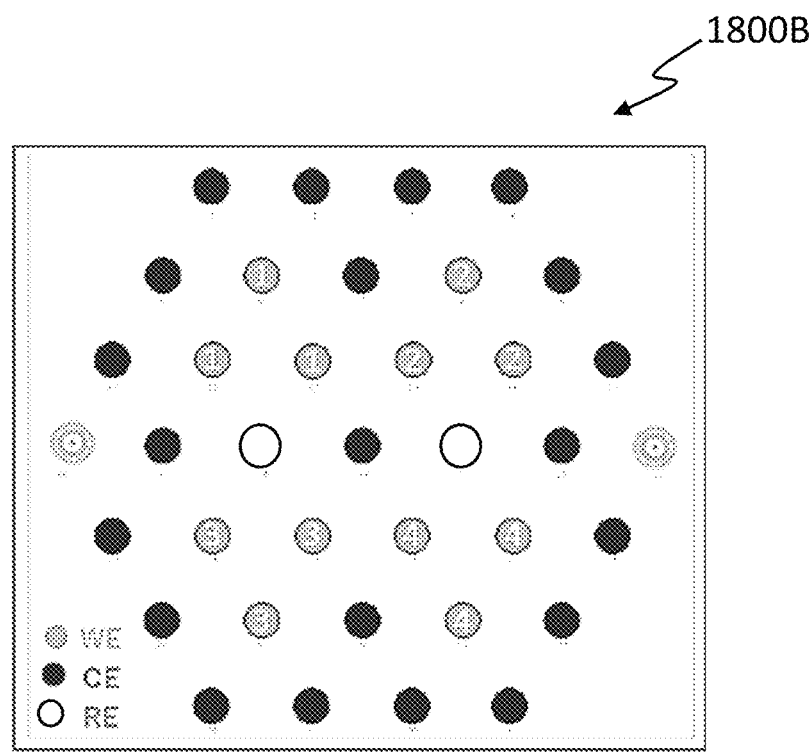

As another example, FIG. 18B depicts a variation of a microneedle array 1800B including four symmetrical groups of three working electrodes (WE), with the four working electrode groups labeled "1", "2", "3", and "4." In this variation, the four working electrode groups are distributed in a radially symmetrical manner in the microneedle array. Each working electrode group is adjacent to one of two reference electrode (RE) constituents in the microneedle array and arranged in a symmetrical manner. The microneedle array also includes counter electrodes (CE) arranged around the perimeter of the microneedle array, except for two electrodes on vertices of the hexagon that are inactive or may be used for other features or modes of operation.

Figure 18C:
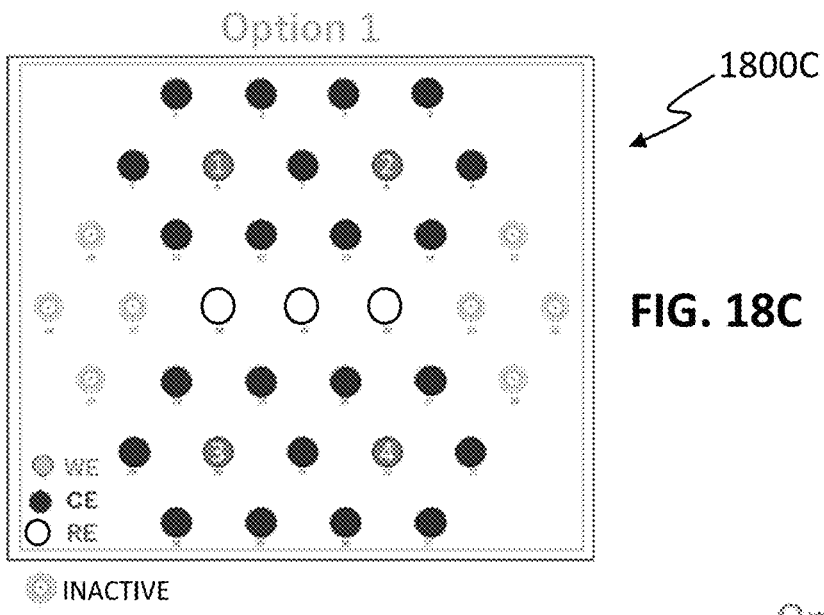

In some variations, only a portion of microneedle array may include active electrodes. For example, FIG. 18C depicts a variation of a microneedle array 1800C with 37 microneedles and a reduced number of active electrodes, including four working electrodes (labeled "1", "2", "3", and "4") in a bilaterally symmetrical arrangement, twenty-two counter electrodes, and three reference electrodes. The remaining eight electrodes in the microneedle array are inactive. In the microneedle array shown in FIG. 18C, each of the working electrodes is surrounded by a group of counter electrodes. Two groups of such clusters of working electrodes and counter electrodes are separated by a row of the three reference electrodes.

Figure 18D:
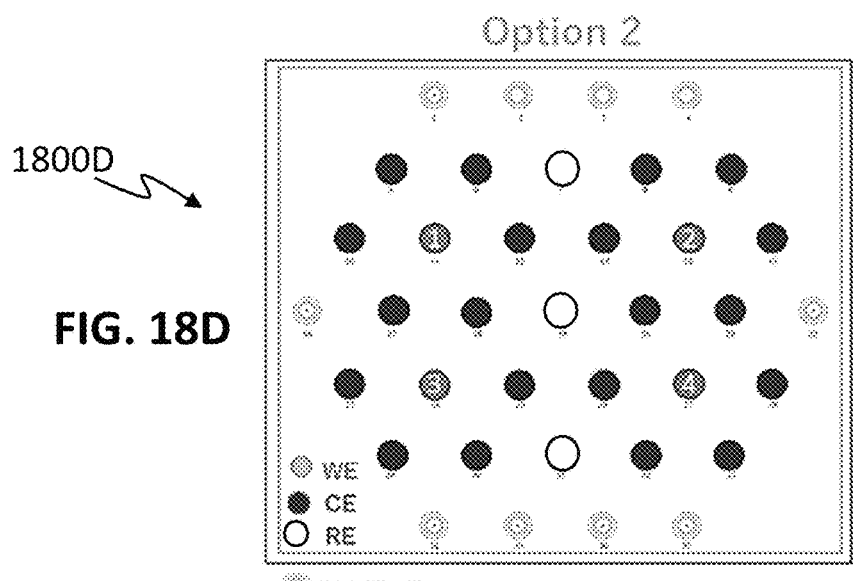

As another example, FIG. 18D depicts a variation of a microneedle array 1800D with 37 microneedles and a reduced number of active electrodes, including four working electrodes (labeled "1", "2", "3", and "4") in a bilaterally symmetrical arrangement, twenty counter electrodes, and three reference electrodes, where the remaining ten electrodes in the microneedle array are inactive.

Figure 18E:
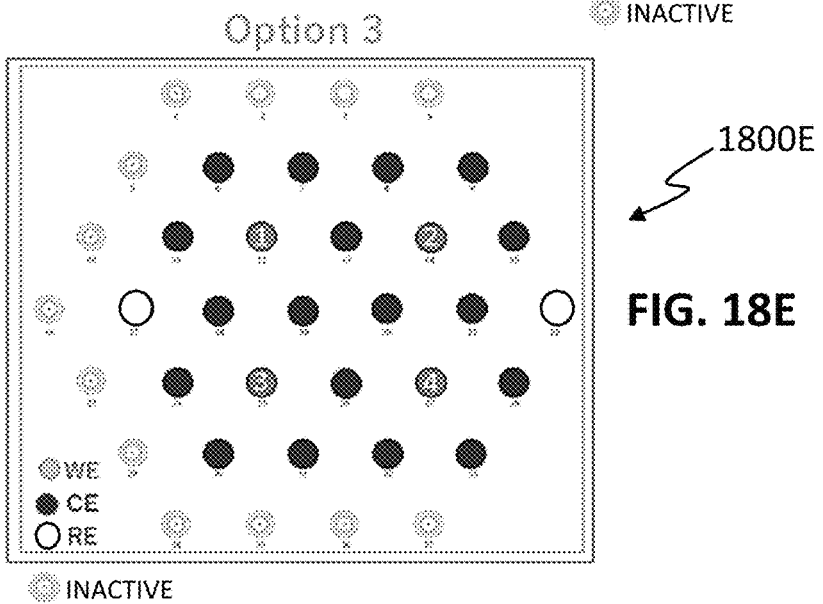

As another example, FIG. 18E depicts a variation of a microneedle array 1800E with 37 microneedles and a reduced number of active electrodes, including four working electrodes (labeled "1", "2", "3", and "4"), eighteen counter electrodes, and two reference electrodes. The remaining thirteen electrodes in the microneedle array are inactive. The inactive electrodes are along a partial perimeter of the overall microneedle array, thereby reducing the effective size and shape of the active microneedle arrangement to a smaller hexagonal array. Within the active microneedle arrangement, the four working electrodes are generally in a radially symmetrical arrangement, and each of the working electrodes is surrounded by a group of counter electrodes.

Figure 18F:
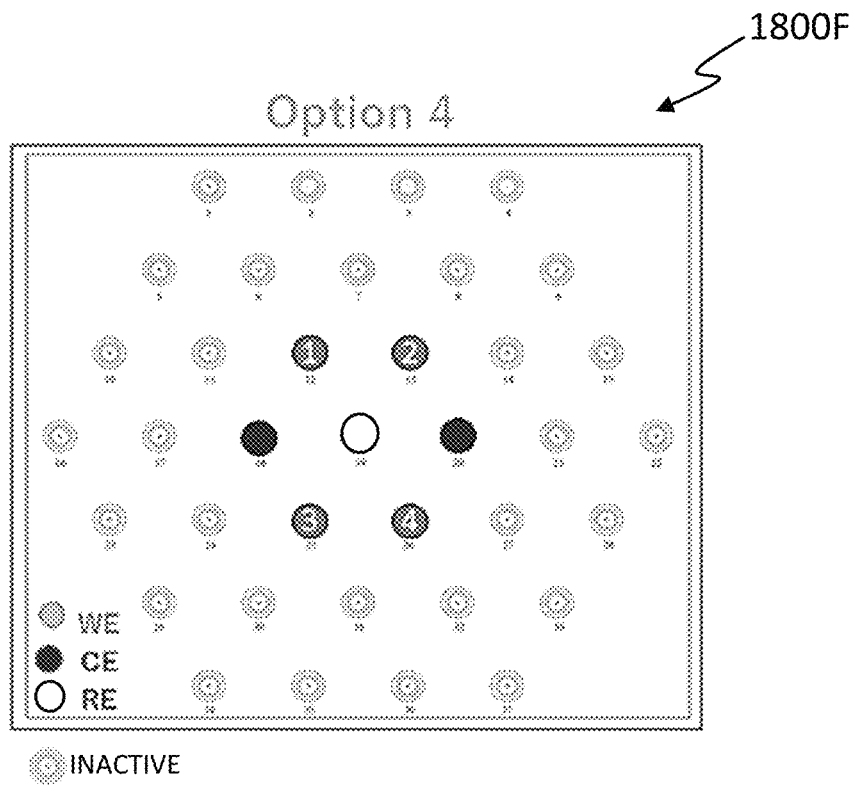

FIG. 18F depicts another example variation of a microneedle array 1800F with 37 microneedles and a reduced number of active electrodes, including four working electrodes (labeled "1", "2", "3", and "4"), two counter electrodes, and one reference electrode. The remaining thirty electrodes in the microneedle array are inactive. The inactive electrodes are arranged in two layers around the perimeter of the overall microneedle array, thereby reducing the effective size and shape of the active microneedle arrangement to a smaller hexagonal array centered around the reference electrode. Within the active microneedle arrangement, the four working electrodes are in a bilaterally symmetrical arrangement and the counter electrodes are equidistant from the central reference electrode.

Figure 18G:
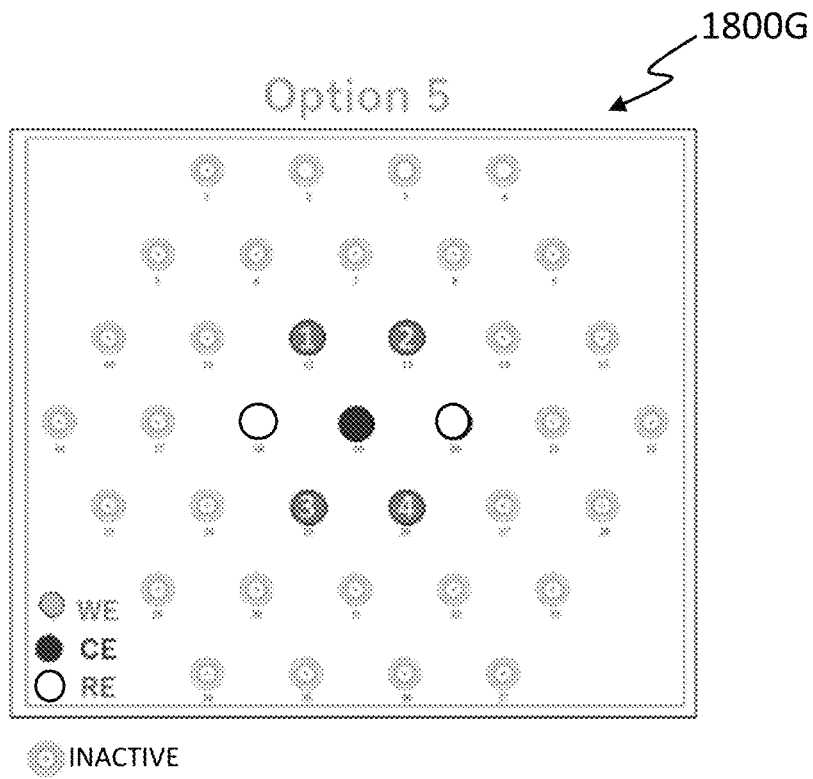

FIG. 18G depicts another example variation of a microneedle array 1800G with 37 microneedles and a reduced number of active electrodes. The active electrodes in microneedle array 1800G are arranged in a similar manner as that in microneedle array 1800F shown in FIG. 18F, except that the microneedle array 1800G includes one counter electrode and two reference electrodes, and the smaller hexagonal array of active microneedles is centered around the counter electrode. Within the active microneedle arrangement, the four working electrodes are in a bilaterally symmetrical arrangement and the reference electrodes are equidistant from the central counter electrode.

Figure 18H:
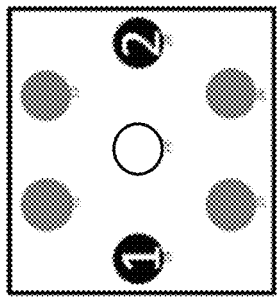

FIG. 18H depicts another example variation of a microneedle array 1800H with seven microneedles. The microneedle arrangement contains two microneedles assigned as independent working electrodes (1 and 2), a counter electrode contingent comprised of 4 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

Figure 18I:
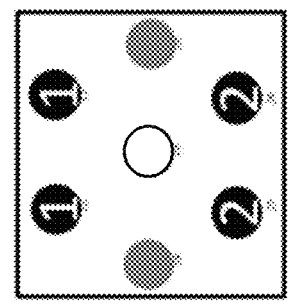

FIG. 18I depicts another example variation of a microneedle array 1800I with seven microneedles. The microneedle arrangement contains four microneedles assigned as two independent groupings (1 and 2) of two working electrodes each, a counter electrode contingent comprised of 2 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

Figure 18J:
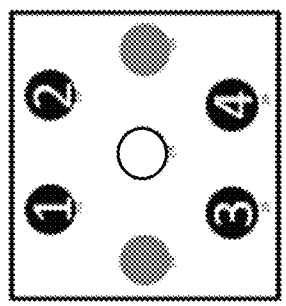

FIG. 18J depicts another example variation of a microneedle array 1800J with seven microneedles. The microneedle arrangement contains four microneedles assigned as independent working electrodes (1, 2, 3, and 4), a counter electrode contingent comprised of 2 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

While FIGS. 18A-18J illustrate example variations of microneedle array configurations, it should be understood that these figures are not limiting and other microneedle configurations (including different numbers and/or distributions of working electrodes, counter electrodes, and reference electrodes, and different numbers and/or distributions of active electrodes and inactive electrodes, etc.) may be suitable in other variations of microneedle arrays.

As described above, each microneedle in the microneedle array may include an electrode. In some variations, multiple distinct types of electrodes may be included among the microneedles in the microneedle array. For example, in some variations the microneedle array may function as an electrochemical cell operable in an electrolytic manner with three types of electrodes. In other words, the microneedle array may include at least one working electrode, at least one counter electrode, and at least one reference electrode. Thus, the microneedle array may include three distinct electrode types, though one or more of each electrode type may form a complete system (e.g., the system might include multiple distinct working electrodes). Furthermore, multiple distinct microneedles may be electrically joined to form an effective electrode type (e.g., a single working electrode may be formed from two or more connected microneedles with working electrode sites). Each of these electrode types may include a metallization layer and may include one or more coatings or layers over the metallization layer that help facilitate the function of that electrode.

Generally, the working electrode is the electrode at which oxidation and/or reduction reaction of interest occurs for detection of an analyte of interest. The counter electrode functions to source (provide) or sink (accumulate) the electrons, via an electrical current, that are required to sustain the electrochemical reaction at the working electrode. The reference electrode functions to provide a reference potential for the system; that is, the electrical potential at which the working electrode is biased is referenced to the reference electrode. A fixed, time-varying, or at least controlled potential relationship is established between the working and reference electrodes, and within practical limits no current is sourced from or sinked to the reference electrode. Additionally, to implement such a three-electrode system, the analyte monitoring device may include a suitable potentiostat or electrochemical analog front end to maintain a fixed potential relationship between the working electrode and reference electrode contingents within the electrochemical system (via an electronic feedback mechanism), while permitting the counter electrode to dynamically swing to potentials required to sustain the redox reaction of interest.

As described above, the working electrode is the electrode at which the oxidation and/or reduction reaction of interest occurs. In some variations, sensing may be performed at the interface of the working electrode and interstitial fluid located within the body (e.g., on an outer surface of the overall microneedle). In some variations, a working electrode may include an electrode material and a biorecognition layer in which a biorecognition element (e.g., enzyme) is immobilized on the working electrode to facilitate selective analyte quantification. In some variations, the biorecognition layer may also function as an interference-blocking layer and may help prevent endogenous and/or exogenous species from directly oxidizing (or reducing) at the electrode. In some variations, the biorecognition layer and the interference-blocking layer may be separate and distinct layers. In some variations, in addition to the biorecognition layer and/or the combined biorecognition and interference-blocking layer, an electrode protecting layer may be provided for additional protection of the electrode.

A redox current detected at the working electrode may be correlated to a detected concentration of an analyte of interest. This is because assuming a steady-state, diffusion-limited system, the redox current detected at the working electrode follows the Cottrell relation below:

$$i(t) = \frac{nFA\sqrt{D}\,C}{\sqrt{\pi t}}$$

where n is the stoichiometric number of electrons mitigating a redox reaction, F is Faraday's constant, A is electrode surface area, D is the diffusion coefficient of the analyte of interest, C is the concentration of the analyte of interest, and t is the duration of time that the system is biased with an electrical potential. Thus, the detected current at the working electrode scales linearly with the analyte concentration.

Moreover, because the detected current is a direct function of electrode surface area A, the surface area of the electrode may be increased to enhance the sensitivity (e.g., amperes per molar of analyte) of the sensor. For example, multiple singular working electrodes may be grouped into arrays of two or more constituents to increase total effective sensing surface area. To obtain redundancy, multiple working electrodes may be operated as parallelized sensors to obtain a plurality of independent measures of the concentration of an analyte of interest. The working electrode can either be operated as the anode (such that an analyte is oxidized at its surface), or as the cathode (such that an analyte is reduced at its surface).

Figure 19A:
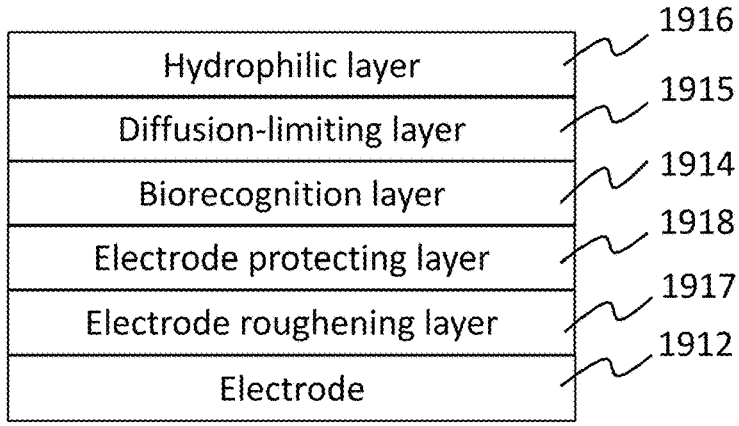
FIGS. 19A-19C depict illustrative schematics of layered structures of a working electrode, a counter electrode, and a reference electrode, respectively.

FIG. 19A depicts a schematic of an exemplary set of layers for a working electrode 1910. For example, as described above, in some variations the working electrode 1910 may include an electrode material 1912 and a biorecognition layer 1914 including a biorecognition element. The electrode material 1912 functions to encourage the electrocatalytic detection of an analyte or the product of the reaction of the analyte and the biorecognition element. The electrode material 1912 also provides ohmic contact and routes an electrical signal from the electrocatalytic reaction to processing circuitry. In some variations, the electrode material 1912 may include platinum. However, the electrode material 1912 may alternatively include, for example, palladium, iridium, rhodium, gold, ruthenium, titanium, nickel, carbon, doped diamond, or other suitable catalytic and inert material.

In some variations, the electrode material 1912 may be coated with a highly porous electrocatalytic layer and/or electrode roughening layer 1917, which may augment the electrode surface area for enhanced sensitivity. The electrode roughening layer 1917 may enable the electrocatalytic oxidation or reduction of the product of the biorecognition reaction facilitated by the biorecognition layer 1914. However, in some variations, the electrode roughening layer 1917 may be omitted. The electrode may enable the electrocatalytic oxidation or reduction of the product of the biorecognition reaction if the electrode roughening layer 1917 is not present.

The biorecognition layer 1914 may be arranged over the electrode material 1912 (or the electrode roughing layer 1917 if present) and functions to immobilize and stabilize the biorecognition element which facilitates selective analyte quantification for extended time periods. In some variations, the biorecognition element may include an enzyme, such as an oxidase. As an exemplary variation for use in a glucose monitoring system, the biorecognition element may include glucose oxidase, which converts glucose, in the presence of oxygen, to an electroactive product (i.e., hydrogen peroxide) that can be detected at the electrode surface. Specifically, the redox equation associated with this exemplary variation is Glucose+Oxygen à Hydrogen Peroxide+ Gluconolactone (mediated by glucose oxidase); Hydrogen Peroxide à Water+Oxygen (mediated by applying an oxidizing potential at the working electrode).

However, in other variations, the biorecognition element may additionally or alternatively comprise another suitable oxidase or oxidoreductase enzyme such as lactate oxidase, alcohol oxidase, beta-hydroxybutyrate dehydrogenase, tyrosinase, catalase, ascorbate oxidase, cholesterol oxidase, choline oxidase, pyruvate oxidase, urate oxidase, urease, and/or xanthine oxidase.

In some variations, the biorecognition element may be cross-linked with an amine-condensing carbonyl chemical species that may help stabilize the biorecognition element within the biorecognition layer 1914.

In some variations, the working electrode may further include a diffusion-limiting layer 1915 arranged over the biorecognition layer 1914. The diffusion-limiting layer 1915 may function to limit the flux of the analyte of interest in order to reduce the sensitivity of the sensor to endogenous oxygen fluctuations. For example, the diffusion-limiting layer 1915 may attenuate the concentration of the analyte of interest so that it becomes the limiting reactant to an aerobic enzyme. However, in some variation (e.g., if the biorecognition element is not aerobic), the diffusion-limiting layer 1915 may be omitted.

The working electrode may further include, in some variations, a hydrophilic layer 1916 or biocompatibility layer that provides for a biocompatible interface to, for example, reduce the foreign body response. The hydrophilic layer may be added through, for example, plasma polymerization techniques or grafting techniques. In some variations the hydrophilic layer 1916 may be omitted (e.g., if the diffusion-limiting layer expresses hydrophilic moieties to serve this purpose.

In some variations, an electrode protecting layer 1918 may be arranged over the electrode roughening layer 1917. The biorecognition layer 1914 is arranged over the electrode protecting layer 1918. The diffusion-limiting layer 1915 may function to limit the flux of the analyte of interest to reduce the sensitivity of the sensor to endogenous oxygen fluctuations. The optional hydrophilic layer 1916 is arranged over the diffusion-limiting layer 1915 to provide the biocompatible interface to reduce the foreign body response.

In some variations, the electrode protecting layer 1918 may be arranged over the electrode material 1912. The biorecognition layer 1914, which may include interference rejection components, may be arranged over the electrode protecting layer 1918. The diffusion-limiting layer 1915 may be arranged over the biorecognition layer 1914.

As described above, the counter electrode is the electrode that is sourcing or sinking electrons (via an electrical current) required to sustain the electrochemical reaction at the working electrode. The number of counter electrode constituents can be augmented in the form of a counter electrode array to enhance surface area such that the current-carrying capacity of the counter electrode does not limit the redox reaction of the working electrode. It thus may be desirable to have an excess of counter electrode area versus the working electrode area to circumvent the current-carrying capacity limitation. If the working electrode is operated as an anode, the counter electrode will serve as the cathode and vice versa. Similarly, if an oxidation reaction occurs at the working electrode, a reduction reaction occurs at the counter electrode and vice versa. Unlike the working or reference electrodes, the counter electrode is permitted to dynamically swing to electrical potentials required to sustain the redox reaction of interest on the working electrode.

Figure 19B:
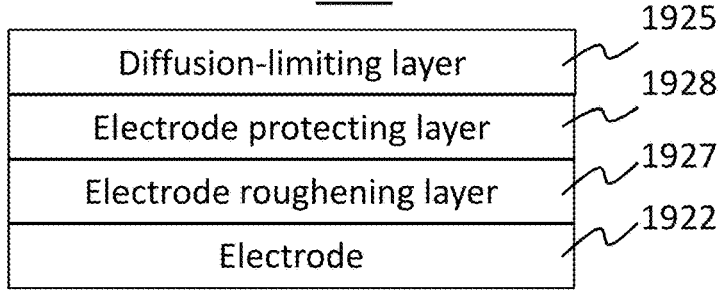

As shown in FIG. 19B, a counter electrode 1920 may include an electrode material 1922, similar to electrode material 1912. For example, like the electrode material 1912, the electrode material 1922 in the counter electrode 1920 may include a noble metal such as gold, platinum, palladium, iridium, carbon, doped diamond, and/or other suitable catalytic and inert material.

In some variations, the counter electrode 1920 may have few or no additional layers over the electrode material 1922. However, in some variations the counter electrode 1920 may benefit from increased surface area to increase the amount of current it can support. For example, the counter electrode material 1922 may be textured or otherwise roughened in such a way to augment the surface area of the electrode material 1922 for enhanced current sourcing or sinking ability. The counter electrode 1920 may include an electrode roughening layer 1927. The electrode roughening layer may include, for example, platinum black, which may augment electrode surface as described above with respect to some variations of the working electrode. However, in some variations of the counter electrode, the electrode roughening layer 1927 may be omitted.

In some variations, the counter electrode 1920 may include a diffusion-limiting layer 1925 (e.g., arranged over the electrode). The diffusion-limiting layer 1925 may, for example, be similar to the diffusion-limiting layer 1915 described above with respect to FIG. 19A. In some variations in which the diffusion-limiting layer 1925 is included, the counter electrode 1920 may further include a hydrophilic layer that provides for a biocompatible interface to, for example, reduce the foreign body response. The hydrophilic layer may be arranged over the diffusion-limiting layer 1925.

In some variations, the counter electrode 1920 may include an electrode protecting layer 1928, such as that described with reference to the working electrode. The electrode protecting layer 1928 may be arranged over the electrode material 1922 or, in variations with the electrode roughening layer 1927, the electrode protecting layer 1928, if provided, is arranged over the electrode roughening layer. In some variations, the diffusion-limiting layer 1925 may be arranged over the electrode protecting layer 1928. In some variations, a hydrophilic layer may be arranged over the diffusion-limiting layer 1925.

As described above, the reference electrode functions to provide a reference potential for the system; that is, the electrical potential at which the working electrode is biased is referenced to the reference electrode. A fixed or at least controlled potential relationship may be established between the working and reference electrodes, and within practical limits no current is sourced from or sinked to the reference electrode.

Figure 19C:
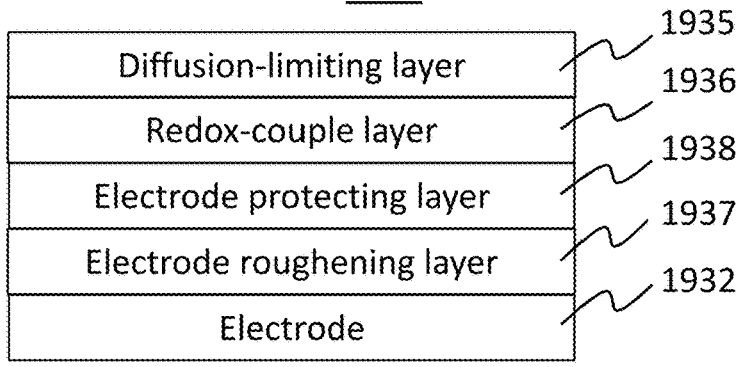

As shown in FIG. 19C, a reference electrode 1930 may include an electrode material 1932, similar to electrode material 1912. In some variations, like the electrode material 1912, the electrode material 1932 in the reference electrode 1930 may include a metal salt or metal oxide, which serves as a stable redox coupled with a well-known electrode potential. For example, the metal salt may, for example, include silver-silver chloride (Ag/AgCl) and the metal oxide may include iridium oxide (IrOx/$Ir_2O_3$/$IrO_2$). In other variations, noble and inert metal surfaces may function as quasi-reference electrodes and include gold, platinum, palladium, iridium, carbon, doped diamond, and/or other suitable catalytic and inert material. Furthermore, in some variations the reference electrode 1930 may be textured or otherwise roughened in such a way to enhance adhesion with any subsequent layers. Such subsequent layers on the electrode material 1932 may include an electrode roughening layer 1937. In some variations, the electrode roughening layer 1937 may be omitted.

The reference electrode 1930 may, in some variations, further include a redox-couple layer 1936, which main contain a surface-immobilized, solid-state redox couple with a stable thermodynamic potential. For example, the reference electrode may operate at a stable standard thermodynamic potential with respect to a standard hydrogen electrode (SHE). The high stability of the electrode potential may be attained by employing a redox system with constant (e.g., buffered or saturated) concentrations of each participant of the redox reaction. For example, the reference electrode may include saturated Ag/AgCl (E=+0.197V vs. SHE) or IrOx (E=+0.177 vs. SHE, pH=7.00) in the redox-couple layer 1936. Other examples of redox-couple layers 1936 may include a suitable conducting polymer with a dopant molecule such as that described in U.S. Patent Pub. No. 2019/0309433, which is incorporated in its entirety herein by this reference. In some variations, the reference electrode may be used as a half-cell to construct a complete electrochemical cell.

In some variations, the reference electrode 1930 may include a diffusion-limiting layer 1935 (e.g., arranged over the electrode 1932 and/or the redox-couple layer 1936). The diffusion-limiting layer 1935 may, for example, be similar to the diffusion-limiting layer 1915 described above with respect to FIG. 19A. In some variations in which the diffusion-limiting layer 1935 is included, the reference electrode 1930 may further include a hydrophilic layer that provides for a biocompatible interface to, for example, reduce the foreign body response. The hydrophilic layer may be arranged over the diffusion-limiting layer 1935.

In some variations, the reference electrode 1930 may include an electrode protecting layer 1938, such as that described with reference to the working electrode and/or the counter electrode. The electrode protecting layer 1938 may be arranged over the electrode material 1932 or, in variations with an electrode roughening layer 1937, the electrode protecting layer 1938, if provided, is arranged over the electrode roughening layer 1937.

In some variations, an electrode roughening layer 1937 is arranged over the electrode material 1932. An electrode protecting layer 1938 is arranged over the electrode roughening layer 1937, and the redox-couple layer 1936 is arranged over the electrode protecting layer 1938. In some variations, a diffusion-limiting layer 1935 is arranged over the redox couple layer 1936. In some variations, a hydrophilic layer may be arranged over the diffusion-limiting layer 1935.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

NUMBERED EMBODIMENTS OF THE INVENTION

Notwithstanding the appended claims, the disclosure sets forth the following numbered embodiments:
(1) A method of operating an analyte monitoring device configured to be inserted into skin of a user, the method comprising determining, by a controller of the analyte (1) monitoring device, a source of a power-on event, the source of the power-on event being a connection with a battery or power received from an energy harvesting module, and transitioning the analyte monitoring device to a mode of operation corresponding to the determined source of the power-on event, wherein when the determined source of the power-on event is the connection with the battery, the corresponding mode of operation comprises a start-up mode, and when the source of the power-on event is the power received from the energy harvesting module, the corresponding mode of operation comprises a reset mode.

(2) The method of (1), wherein the power-on event is the controller being powered on or a receipt, by the controller, of a power-on signal.

(3) The method of either (1) or (2), wherein the determining comprises determining whether the battery is connected to the controller based on a signal between the battery and the controller.

(4) The method of any one of (1) to (3), wherein the determining comprises determining whether the analyte monitoring device is transitioned to a usable state.

(5) The method of (4), wherein determining that the analyte monitoring device is in the usable state is based on data from one or more non-analyte sensors of the analyte monitoring device, the data comprising one or more of light data, magnetic field data, accelerometer data, and capacitance data.

(6) The method of (5), wherein the light data comprises ambient light data received from an ambient light sensor of the analyte monitoring device.

(7) The method of (6), wherein the transition of the analyte monitoring device to the usable state causes a phototransistor of the analyte monitoring device to generate a signal to a power connect circuit of the analyte monitoring device, the signal closing a switch of the power connect circuit to couple the battery to the controller.

(8) The method of (7), wherein closing the switch of the power connect circuit further couples the battery to an analog front end of the analyte monitoring device, the analog front end being configured to convert analog current measurements obtained by a microneedle array of the analyte monitoring device to digital values, the digital values being indicative of an analyte concentration.

(9) The method of either (4) or (5), further comprising, when it is determined that the analyte monitoring device is not in the usable state, determining whether the analyte monitoring device is positioned in a communication field.

(10) The method of (9), wherein determining that the analyte monitoring device is in the communication field is based on detecting the communication field based on a signal between the energy harvesting module and the controller.

(11) The method of (10), further comprising waiting a predetermined period of time to receive an over-the air transmission from a remote device.

(12) The method of (11), further comprising, responsive to receiving the over-the-air transmission, applying reconfiguration parameters and entering a powered-off state.

(13) The method of either (11) or (12), further comprising, responsive to not receiving the over-the-air transmission, entering a powered-off state.

(14) The method of any one of (11) to (13), further comprising responsive to not receiving the over-the-air transmission, enabling a timer and attempting to shutdown, and when it is determined that shutdown is not successful within a time limit of the timer, determining whether the analyte monitoring device is transitioned to a usable state, or when it is determined that shutdown is successful within the time limit of the timer, entering a powered-off state.

(15) The method of either (9) or (10), further comprising, responsive to determining that the analyte monitoring device is not positioned in the communication field, entering a powered-off state.

(16) The method of any of (9), (10), and (15), further comprising, responsive to determining that the analyte monitoring device is not positioned in the communication field enabling a timer and attempting to shutdown, and when it is determined that shutdown is not successful within a time limit of the timer, determining whether the analyte monitoring device is transitioned to a usable state, or when it is determined that shutdown is successful within the time limit of the timer, entering a powered-off state.

(17) The method of any one of (1) to (4), wherein the start-up mode comprises a sequence from an idle mode to an operational mode.

(18) The method of (17), further comprising, responsive to a confirmation of an insertion event, transitioning the analyte monitoring device from the idle mode to the operational mode.

(19) The method of (18), wherein the confirmation of the insertion event is based on one or more of an elapsed time, accelerometer data, an electrical current resulting from an applied bias potential, and a communication from an external device.

(20) An analyte monitoring device, comprising a microneedle array configured to be inserted into skin of a user and obtain analog current measurements, a battery, an energy harvesting module, and a controller configured to determine a source of a power-on event, the source of the power-on event being a connection with the battery or power received from the energy harvesting module, and transition the analyte monitoring device to a mode of operation corresponding to the determined source of the power-on event, wherein when the determined source of the power-on event is the connection with the battery, the corresponding mode of operation comprises a start-up mode, and when the source of the power-on event is the power received from the energy harvesting module, the corresponding mode of operation comprises a reset mode.

(21) The analyte monitoring device of (20), wherein the power-on event is the controller being powered on or a receipt, by the controller, of a power-on signal.

(22) The analyte monitoring device of either (20) or (21), wherein the determining comprises determining whether the battery is connected to the controller based on a signal between the battery and the controller.

(23) The analyte monitoring device of any one of (20) to (22), wherein the determining comprises determining whether the analyte monitoring device is transitioned to a usable state.

(24) The analyte monitoring device of (23), wherein determining that the analyte monitoring device is in the usable state is based on data from one or more non-analyte sensors of the analyte monitoring device, the data comprising one or more of light data, magnetic field data, accelerometer data, and capacitance data.

(25) The method of (24), wherein the light data comprises ambient light data received from an ambient light sensor of the analyte monitoring device.

(26) The analyte monitoring device of either (24) or (25), wherein the transition of the analyte monitoring device to the usable state causes a phototransistor of the analyte monitoring device to generate a signal to a power connect circuit of the analyte monitoring device, the signal closing a switch of the power connect circuit to couple the battery to the controller.

(27) The analyte monitoring device of (26), wherein closing the switch of the power connect circuit further couples the battery to an analog front end of the analyte monitoring device, the analog front end being configured to convert analog current measurements obtained by a microneedle array of the analyte monitoring device to digital values, the digital values being indicative of an analyte concentration.

(28) The analyte monitoring device of either (23) or (24), wherein the controller is further configured to, when it is determined that the analyte monitoring device is not in the usable state, determine whether the analyte monitoring device is positioned in a communication field.

(29) The analyte monitoring device of (28), wherein determining that the analyte monitoring device is in the communication field is based on detecting the communication field based on a signal between the energy harvesting module and the controller.

(30) The analyte monitoring device of (29), wherein the controller is further configured to wait a predetermined period of time to receive an over-the air transmission from a remote device.

(31) The analyte monitoring device of (30), wherein the controller is further configured to, responsive to receiving the over-the-air transmission, apply reconfiguration parameters and enter a powered-off state.

(32) The analyte monitoring device of either (30) or (31), wherein the controller is further configured to, responsive to not receiving the over-the-air transmission, enter a powered-off state.

(33) The analyte monitoring device of any one of (30) to (32), wherein the controller is further configured to responsive to not receiving the over-the-air transmission, enable a timer and attempt to shutdown, and when it is determined that shutdown is not successful within a time limit of the timer, determining whether the analyte monitoring device is transitioned to a usable state, or when it is determined that shutdown is successful within the time limit of the timer, entering a powered-off state.

(34) The analyte monitoring device of either (28) or (29), wherein the controller is further configured to, responsive to determining that the analyte monitoring device is not positioned in the communication field, enter a powered-off state.

(35) The analyte monitoring device of any one of (28), (29), and (34), wherein the controller is further configured to, responsive to determining that the analyte monitoring device is not positioned in the communication field enabling a timer and attempting to shutdown, and when it is determined that shutdown is not successful within a time limit of the timer, determining whether the analyte monitoring device is transitioned to a usable state, or when it is determined that shutdown is successful within the time limit of the timer, entering a powered-off state.

(36) The analyte monitoring device of any one of claim (20), (21), (22), and (23), wherein the start-up mode comprises a sequence from an idle mode to an operational mode.

(37) The analyte monitoring device of (36), further comprising, responsive to a confirmation of an insertion event, transitioning the analyte monitoring device from the idle mode to the operational mode.

(38) The analyte monitoring device of (37), wherein the confirmation of the insertion event is based on one or more of an elapsed time, accelerometer data, an electrical current resulting from an applied bias potential, and a communication from an external device.

(39) A method of operating an analyte monitoring device configured to be inserted into skin of a user, the method comprising determining, by a controller of the analyte monitoring device, that a power-on event is a valid power-on event, wherein the valid power-on event comprises a transition of the analyte monitoring device to a usable state or an intentional positioning of the analyte monitoring device in a communication field, and after determining the power-on event is the valid power-on event, transitioning the analyte monitoring device to a mode corresponding to the respective valid power-on event.

(40) The method of (39), wherein the power-on event is the controller being powered on or a receipt, by the controller, of a power-on signal.

(41) The method of either (39) or (40), wherein the usable state is a pre-insertion state in which the analyte monitoring device is ready for application to the skin of the user or a post-insertion state in which the analyte monitoring device is inserted into the skin of the user.

(42) The method of any one of (39) to (41), wherein the determining that the power-on event comprises a valid power-on event comprises determining whether the analyte monitoring device is transitioned to the usable state, and responsive to a determination that the analyte monitoring device is not transitioned to the usable state, determining that the analyte monitoring device is intentionally positioned in the communication field.

(43) The method of any one of (39) to (42), wherein the determining comprises determining if the analyte monitoring device is in the usable state, the usable state being a pre-insertion state or a post-insertion state.

(44) The method of (43), wherein determining that the analyte monitoring device is in the usable state is based on data from one or more non-analyte sensors of the analyte monitoring device, the data comprising one or more of light data, magnetic field data, accelerometer data, and capacitance data.

(45) The method of (44), wherein the light data comprises ambient light data received from an ambient light sensor of the analyte monitoring device.

(46) The method of (45), wherein the transition of the analyte monitoring device to the usable state causes a phototransistor of the analyte monitoring device to generate a signal to a power connect circuit of the analyte monitoring device, the signal closing a switch of the power connect circuit to couple a power source to the controller.

(47) The method of (46), wherein closing the switch of the power connect circuit further couples the power source to an analog front end of the analyte monitoring device, the analog front end being configured to convert analog current measurements obtained by a microneedle array of the analyte monitoring device to digital values, the digital values being indicative of an analyte concentration.
(48) The method of any one of (39) to (43), wherein the mode corresponding to the transition of the analyte monitoring device to the usable state comprises an idle mode.
(49) The method of (48), further comprising, responsive to a confirmation of an insertion event, transitioning the analyte monitoring device from the idle mode to an operational mode.
(50) The method of (49), wherein the confirmation of the insertion event is based on one or more of an elapsed time, accelerometer data, an electrical current resulting from an applied bias potential, and a communication from an external device.
(51) The method of any one of (39) to (43) and (48), further comprising, responsive to determining that the analyte monitoring device is not in the usable state, determining if the analyte monitoring device is intentionally positioned in the communication field.
(52) The method of (51), wherein determining that the analyte monitoring device is intentionally positioned in the communication field comprises detecting the communication field and receiving an over-the-air transmission from a remote device within a predetermined period of time.
(53) The method of (52), wherein the over-the-air transmission comprises reconfiguration parameters for the controller.
(54) The method of any one of (39) to (43), (48), and (51), wherein the mode corresponding to the intentional positioning of the analyte monitoring device in the communication field comprises a reconfiguration mode.
(55) The method of (54), further comprising transitioning the analyte monitoring device to a powered-off mode responsive to completion of the reconfiguration mode.
(56) An analyte monitoring device, comprising a microneedle array configured to be inserted into skin of a user and obtain analog current measurements, and a controller configured to determine that a power-on event is a valid power-on event, wherein the valid power-on event comprises a transition of the analyte monitoring device to a usable state or an intentional positioning of the analyte monitoring device in a communication field, and after determining the power-on event is the valid power-on event, transition the analyte monitoring device to a mode corresponding to the respective valid power-on event.
(57) The analyte monitoring device of (56), wherein the power-on event is the controller being powered on or a receipt, by the controller, of a power-on signal.
(58) The analyte monitoring device of either (56) or (57), wherein the usable state is a pre-insertion state in which the analyte monitoring device is ready for application to the skin of the user or a post-insertion state in which the analyte monitoring device is inserted into the skin of the user.
(59) The analyte monitoring device of any one of (56) to (58), wherein the determining that the power-on event comprises a valid power-on event comprises determining whether the analyte monitoring device is transitioned to the usable state, and responsive to a determination that the analyte monitoring device is not transitioned to the usable state, determining that the analyte monitoring device is intentionally positioned in the communication field.
(60) The analyte monitoring device of any one of (56) to (59), wherein the determining comprises determining if the analyte monitoring device is in the usable state, the usable state being a pre-insertion state or a post-insertion state.
(61) The analyte monitoring device of (60), wherein determining that the analyte monitoring device is in the usable state is based on data from one or more non-analyte sensors of the analyte monitoring device, the data comprising one or more of light data, magnetic field data, accelerometer data, and capacitance data.
(62) The analyte monitoring device of (61), wherein the light data comprises ambient light data received from an ambient light sensor of the analyte monitoring device.
(63) The analyte monitoring device of (62), wherein the transition of the analyte monitoring device to the usable state causes a phototransistor of the analyte monitoring device to generate a signal to a power connect circuit of the analyte monitoring device, the signal closing a switch of the power connect circuit to couple a power source to the controller.
(64) The analyte monitoring device of (63), wherein closing the switch of the power connect circuit further couples the power source to an analog front end of the analyte monitoring device, the analog front end being configured to convert analog current measurements obtained by a microneedle array of the analyte monitoring device to digital values, the digital values being indicative of an analyte concentration.
(65) The analyte monitoring device of any one of (56) to (60), wherein the mode corresponding to the transition of the analyte monitoring device to the usable state comprises an idle mode.
(66) The analyte monitoring device of (65), wherein the controller is further configured to, responsive to a confirmation of an insertion event, transition the analyte monitoring device from the idle mode to an operational mode.
(67) The analyte monitoring device of (66), wherein the confirmation of the insertion event is based on one or more of an elapsed time, accelerometer data, an electrical current resulting from an applied bias potential, and a communication from an external device.
(68) The analyte monitoring device of any one of (56) to (60) and (65), wherein the controller is further configured to, responsive to determining that the analyte monitoring device is not in the usable state, determine if the analyte monitoring device is intentionally positioned in the communication field.
(69) The analyte monitoring device of (68), wherein determining that the analyte monitoring device is intentionally positioned in the communication field comprises detecting the communication field and receiving an over-the-air transmission from a remote device within a predetermined period of time.
(70) The analyte monitoring device of (69), wherein the over-the-air transmission comprises reconfiguration parameters for the controller.
(71) The analyte monitoring device of any one of (56) to (60), (65), and (68), wherein the mode corresponding to the intentional positioning of the analyte monitoring device in the communication field comprises a reconfiguration mode.

(72) The analyte monitoring device of (71), wherein the controller is further configured to transition the analyte monitoring device to a powered-off mode responsive to completion of the reconfiguration mode.

(73) A method of operating an analyte monitoring device configured to be inserted into skin of a user, the method comprising determining, by a controller of the analyte monitoring device, that a power-on event is a valid power-on event by identifying if the analyte monitoring device is in a usable state, and responsive to determining the power-on event is the valid power-on event, transitioning the analyte monitoring device to an idle mode.

(74) The method of (73), wherein the identifying comprises identifying if the analyte monitoring device is in one of a pre-insertion state in which the analyte monitoring device is ready for application to the skin of the user or a post-insertion state in which the analyte monitoring device is inserted into the skin of the user.

(75) The method of (74), wherein the identifying if the analyte monitoring device is in one of the pre-insertion state or the post-insertion state comprises obtaining data from one or more non-analyte sensors of the analyte monitoring device, the data comprising one or more of light data, magnetic field data, accelerometer data, and capacitance data.

(76) The method of (75), wherein the light data comprises ambient light data received from an ambient light sensor of the analyte monitoring device.

(77) The method of (76), wherein the transition of the analyte monitoring device to the usable state causes a phototransistor of the analyte monitoring device to generate a signal to a power connect circuit of the analyte monitoring device, the signal closing a switch of the power connect circuit to couple the power source to the controller.

(78) The method of (77), wherein closing the switch of the power connect circuit further couples the power source to an analog front end of the analyte monitoring device, the analog front end being configured to convert analog current measurements obtained by a microneedle array of the analyte monitoring device to digital values, the digital values being indicative of an analyte concentration.

(79) The method of either (73) or (74), further comprising, responsive to a confirmation of an insertion event, transitioning the analyte monitoring device from the idle mode to an operational mode.

(80) The method of (79), wherein the confirmation of the insertion event is based on one or more of an elapsed time, accelerometer data, an electrical current resulting from an applied bias potential, and a communication from an external device.

(81) An analyte monitoring device, comprising a microneedle array configured to be inserted into skin of a user and obtain analog current measurements, and a controller configured to determine that a power-on event is a valid power-on event by identifying if the analyte monitoring device is in a usable state, and responsive to determining the power-on event is the valid power-on event, transition the analyte monitoring device to an idle mode.

(82) The analyte monitoring device of (81), wherein the identifying comprises identifying if the analyte monitoring device is in one of a pre-insertion state in which the analyte monitoring device is ready for application to the skin of the user or a post-insertion state in which the analyte monitoring device is inserted into the skin of the user.

(83) The analyte monitoring device of (82), wherein the identifying if the analyte monitoring device is in one of the pre-insertion state or the post-insertion state comprises obtaining data from one or more non-analyte sensors of the analyte monitoring device, the data comprising one or more of light data, magnetic field data, accelerometer data, and capacitance data.

(84) The analyte monitoring device of (83), wherein the light data comprises ambient light data received from an ambient light sensor of the analyte monitoring device.

(85) The analyte monitoring device of (84), wherein the transition of the analyte monitoring device to the usable state causes a phototransistor of the analyte monitoring device to generate a signal to a power connect circuit of the analyte monitoring device, the signal closing a switch of the power connect circuit to couple the power source to the controller.

(86) The analyte monitoring device of (85), wherein closing the switch of the power connect circuit further couples the power source to an analog front end of the analyte monitoring device, the analog front end being configured to convert analog current measurements obtained by a microneedle array of the analyte monitoring device to digital values, the digital values being indicative of an analyte concentration.

(87) The analyte monitoring device of either (81) or (82), wherein the controller is further configured to, responsive to a confirmation of an insertion event, transition the analyte monitoring device from the idle mode to an operational mode.

(88) The analyte monitoring device of (87), wherein the confirmation of the insertion event is based on one or more of an elapsed time, accelerometer data, an electrical current resulting from an applied bias potential, and a communication from an external device.

(89) A sensor assembly of an analyte monitoring device, comprising a microneedle array configured to obtain analog current measurements, and an electronics assembly, comprising a power source, an analog front end configured to convert the analog current measurements to digital values, the digital values being indicative of a concentration of an analyte, a controller configured to process the digital values, a power connect circuit comprising a switch configured to couple the power source to the controller and to the analog front end, and a photo detect circuit configured to generate, responsive to a triggering event, a signal to the power connect circuit to close the switch, thereby establishing a connection between the power source and the controller and between the power source and the analog front end, wherein a connection between the photo detect circuit and the power connect circuit is established upon a connection between the microneedle array and the electronics assembly.

(90) The sensor assembly of (89), wherein the electronics assembly further comprises a first printed circuit board to which the power source, the analog front end, the controller, the power connect circuit, and the photo detect circuit are coupled, and wherein the microneedle array is coupled to a second printed circuit board.

(91) The sensor assembly of (90), wherein the photo detect circuit comprises a signal line routed between the first circuit board and the second circuit board, wherein the connection between the microneedle array and the electronics assembly closes the signal line of the photo detect circuit.

(92) The sensor assembly of either (89) or (90), wherein the photo detect circuit comprises a phototransistor, and wherein the triggering event comprises exposure to environmental light.

(93) The sensor assembly of any one of (89), (90), and (92), wherein the electronics assembly further comprises a boost circuit coupled between the power connect circuit and the analog front end, the boost circuit configured to boost the voltage to the analog front end.

(94) The sensor assembly of (93), wherein the electronics assembly further comprises at least one light emitting diode, wherein the at least one light emitting diode is coupled to the boost circuit, and wherein the boost circuit is configured to boost the voltage to the at least one light emitting diode.

(95) The sensor assembly of (94), wherein the electronics assembly further comprises a peripheral power switch, the peripheral power switch being configured to control power delivery to an ambient light sensor, and wherein the controller controls a brightness of the at least one light emitting diode based on a level of light detected by the ambient light sensor.

(96) The sensor assembly of (95), wherein the peripheral power switch is further configured to control power delivery to one or more of a kinetic sensor and an output device.

(97) The sensor assembly of any one of (89), (90), (92), and (93), wherein the microneedle array comprises at least one microneedle, the at least one microneedle comprising a tapered distal portion having an insulated distal apex, and an electrode on a surface of the tapered distal portion, wherein the electrode is located proximal to the insulated distal apex.

(98) The sensor assembly of (97), wherein the electrode is a working electrode configured to sense the analyte, wherein the at least one microneedle comprises a biorecognition layer arranged over the working electrode, and wherein the biorecognition layer comprises a biorecognition element.

(99) A method of operating an analyte monitoring device configured to be inserted into skin of a user, the method comprising applying by an analog front end of the analyte monitoring device a first bias potential, the first bias potential applied between a first working electrode and a reference point, measuring a first resulting current at the first working electrode, applying, by the analog front end, a second bias potential, the second bias potential applied between a second working electrode and the reference point, measuring a second resulting current at the second working electrode, and responsive to a determination that at least one of the first resulting current and the second resulting current is within a predetermined threshold, transitioning the analyte monitoring device to an operational mode during which an operating bias potential is applied, wherein the analyte monitoring device comprises a microneedle array comprising at least two working electrodes, a reference electrode, and a counter electrode, each positioned on respective microneedles of the microneedle array.

(100) The method of (99), wherein the reference point comprises a combined counter electrode/reference electrode reference point, wherein the combined counter electrode/reference electrode reference point is connected to a counter input of the analog front end and a reference input of the analog front end.

(101) The method of (100), further comprising, prior to applying the first bias potential, forming the combined counter electrode/reference electrode reference point by closing a first switch between the counter input and the reference input and opening a second switch at the reference input.

(102) The method of (101), the transitioning comprising opening the first switch and closing the second switch.

(103) The method of either (99) or (100), further comprising in the operational mode, applying the operating bias potential to the first working electrode if the first resulting current is within the predetermined threshold, and applying the operating bias potential to the second working electrode if the second resulting current is within the predetermined threshold.

(104) The method of any one of (99), (100), and (103), wherein the analyte monitoring device further comprises a second counter electrode, the second counter electrode positioned on a respective microneedle of the microneedle array.

(105) The method of (104), wherein the counter electrode and the second counter electrode are shorted together and connected to a counter input of the analog front end.

(106) The method of any one of (99), (100), (103), and (104), wherein the first bias potential is one of less than or equal to the operating bias potential, wherein the second bias potential is one of less than or equal to the operating bias potential.

(107) A method of operating an analyte monitoring device configured to be inserted into skin of a user, the method comprising applying by an analog front end of the analyte monitoring device a first bias potential, the first bias potential applied between a first working electrode and a reference point, measuring a first resulting current at the first working electrode, responsive to a determination that the first resulting current is within a predetermined threshold, transitioning the analyte monitoring device to an operational mode during which an operating bias potential is applied, and in the operational mode, applying the operating bias potential to at least a second working electrode, wherein the analyte monitoring device comprises a microneedle array comprising at least two working electrodes, a reference electrode, and a counter electrode, each positioned on respective microneedles of the microneedle array.

(108) The method of (107), wherein the reference point comprises a combined counter electrode/reference electrode reference point, wherein the combined counter electrode/reference electrode reference point is connected to a counter input of the analog front end and a reference input of the analog front end.

(109) The method of (108), further comprising, prior to applying the first bias potential, forming the combined counter electrode/reference electrode reference point by closing a first switch between the counter input and the reference input and opening a second switch at the reference input.

(110) The method of (109), the transitioning comprising opening the first switch and closing the second switch.

(111) The method of either (107) or (108), wherein the analyte monitoring device further comprises a second counter electrode, the second counter electrode positioned on a respective microneedle of the microneedle array.

(112) The method of (111), wherein the counter electrode and the second counter electrode are shorted together and connected to a counter input of the analog front end.

(113) The method of any one of (107), (108), and (111), wherein the first bias potential is one of less than or equal to the operating bias potential.

The invention claimed is:

1. A method of operating an analyte monitoring device comprising an analyte sensor configured to be inserted into skin of a user, the method comprising:
    determining, by a controller of the analyte monitoring device, whether a source of a power-on signal is a first power source;
    responsive to determining that the source of the power-on signal is not the first power source, determining whether the source of the power-on signal is a second power source; and
    transitioning the analyte monitoring device to a powered-off mode of operation when the source of the power-on signal is determined to be the second power source,
    wherein the first power source is a battery and the second power source is an antenna.

2. The method of claim 1, wherein determining whether the source of the power-on signal is the first power source comprises determining whether the battery is connected to the controller based on a signal between the battery and the controller.

3. The method of claim 1, wherein determining whether the source of the power-on signal is the first power source comprises evaluating data from one or more non-analyte sensors of the analyte monitoring device, the data comprising one or more of light data, magnetic field data, accelerometer data, and capacitance data.

4. The method of claim 3, wherein the light data comprises ambient light data received from an ambient light sensor of the analyte monitoring device.

5. The method of claim 4, wherein the evaluating comprises comparing the ambient light data to an ambient light threshold, and wherein it is determined that the source of the power-on signal is not the first power source when the comparing indicates the ambient light data does not satisfy the ambient light threshold.

6. The method of claim 1, wherein determining whether the source of the power-on signal is the second power source n comprises evaluating a signal between the antenna and the controller.

7. The method of claim 6, wherein the evaluating comprises waiting a predetermined period of time to receive an over-the-air transmission from a remote device.

8. The method of claim 7 further comprising, responsive to receiving the over-the-air transmission, applying reconfiguration parameters based on the over-the-air transmission.

9. The method of claim 1, wherein determining whether the source of the power-on signal is the first power source comprises evaluating a signal from a phototransistor associated with the battery.

10. An analyte monitoring device, comprising:
    an analyte sensor configured to be inserted into skin of a user;
    a battery;
    an antenna; and
    a controller configured to:
        determine whether a source of a power-on signal is the battery;
        responsive to determining that the source of the power-on signal is not the battery, determine whether the source of the power-on signal is the antenna; and
        transition the analyte monitoring device to a powered-off mode of operation when the source of the power-on signal is determined to be the antenna.

11. The analyte monitoring device of claim 10, wherein the controller is further configured to determine whether the source of the power-on signal is the battery based on a signal between the battery and the controller.

12. The analyte monitoring device of claim 10, wherein the controller is further configured to determine whether the source of the power-on signal is the battery based on data from one or more non-analyte sensors of the analyte monitoring device, the data comprising one or more of light data, magnetic field data, accelerometer data, and capacitance data.

13. The analyte monitoring device of claim 12, wherein the light data comprises ambient light data received from an ambient light sensor of the analyte monitoring device.

14. The analyte monitoring device of claim 13, wherein the controller is further configured to compare the ambient light data to an ambient light threshold and, when the ambient light data does not satisfy the ambient light threshold, determine whether the analyte monitoring device is positioned in a communication field.

15. The analyte monitoring device of claim 14, wherein the controller is further configured to determine that the analyte monitoring device is in the communication field based on a signal between the antenna and the controller.

16. The analyte monitoring device of claim 15, wherein the controller is further configured to wait a predetermined period of time to receive an over-the-air transmission from a remote device.

17. The analyte monitoring device of claim 16, wherein the controller is further configured to, responsive to receiving the over-the-air transmission, apply reconfiguration parameters based on the over-the-air transmission.

18. A method of operating an analyte monitoring device comprising an analyte sensor configured to be inserted into skin of a user, the method comprising:
    determining, by a controller of the analyte monitoring device, a source of a power-on signal, the source of the power-on signal being associated with power received from an antenna; and
    after determining the source of the power-on signal is associated with power received from the antenna, transitioning the analyte monitoring device to a powered-off mode.

19. The method of claim 18, wherein determining whether the source of the power-on signal is associated with power received from the antenna comprises evaluating a signal between the antenna and the controller.

20. The method of claim 19, wherein evaluating comprises waiting a predetermined period of time to receive an over-the-air transmission from a remote device.

21. The method of claim 20 further comprising, responsive to receiving the over-the-air transmission, applying reconfiguration parameters based on the over-the-air transmission.

* * * * *